(12) United States Patent
Yaver et al.

(10) Patent No.: US 8,383,383 B2
(45) Date of Patent: Feb. 26, 2013

(54) POLYPEPTIDES HAVING LIPASE ACTIVITY AND POLYNUCLEOTIDES ENCODING SAME

(75) Inventors: Debbie Yaver, Davis, CA (US); Suzanne Otani, Elk Grove, CA (US)

(73) Assignees: Novozymes A/S, Bagsvaerd (DK); Novozymes, Inc., Davis, CA (US)

( * ) Notice: Subject to any disclaimer, the term of this patent is extended or adjusted under 35 U.S.C. 154(b) by 0 days.

(21) Appl. No.: 13/599,199

(22) Filed: Aug. 30, 2012

(65) Prior Publication Data

US 2013/0025005 A1    Jan. 24, 2013

Related U.S. Application Data

(62) Division of application No. 13/440,642, filed on Apr. 5, 2012, now Pat. No. 8,268,589, which is a division of application No. 13/294,047, filed on Nov. 10, 2011, now Pat. No. 8,158,400, which is a division of application No. 13/114,258, filed on May 24, 2011, now Pat. No. 8,067,218, which is a division of application No. 12/944,557, filed on Nov. 11, 2010, now Pat. No. 7,955,830, which is a division of application No. 12/687,696, filed on Jan. 14, 2010, now Pat. No. 7,855,172, which is a division of application No. 11/255,553, filed on Oct. 21, 2005, now Pat. No. 7,662,602.

(60) Provisional application No. 60/643,338, filed on Jan. 12, 2005.

(51) Int. Cl.
*C12N 9/10* (2006.01)
*C12N 15/00* (2006.01)
*C12N 1/20* (2006.01)
*C07H 21/04* (2006.01)

(52) U.S. Cl. ............... 435/193; 435/252.3; 435/320.1; 536/23.2

(58) Field of Classification Search ............ 435/193, 435/252.3, 320.1; 532/23.2
See application file for complete search history.

(56) References Cited

U.S. PATENT DOCUMENTS

| 6,103,505 A | 8/2000 | Clausen et al. |
| 6,852,346 B2 | 2/2005 | Zargahi et al. |
| 2006/0281080 A1 | 12/2006 | Albang et al. |

FOREIGN PATENT DOCUMENTS

| WO | 03012071 A2 | 2/2003 |
| WO | 2004018660 A2 | 3/2004 |

OTHER PUBLICATIONS

El-Shahed 1998, Egypt J Microbiol, 23 (3), 537-547.
Galagan et al.,2003, Nature 422, 859-868.
Kundu et al., 1987, J Gen Microbiol 133, 149-153.
Mayordomo et al., 2000,J. Agric Food Chem 48, 105-109.
Mohawed et al., 1988, Egypt J Microbiol, 23 (2), 357-372.
Nierman et al., 2005, Nature 438, 1151-1156.
Database EMBL XP002374177, 2003.
Database GeneSeq XP002374178, 2004.

*Primary Examiner* — Maryam Monshipouri
(74) *Attorney, Agent, or Firm* — Robert L. Starnes

(57) ABSTRACT

The present invention relates to isolated polypeptides having lipase activity and isolated polynucleotides encoding the polypeptides. The invention also relates to nucleic acid constructs, vectors, and host cells comprising the polynucleotides as well as methods for producing and using the polypeptides.

18 Claims, 21 Drawing Sheets

```
         M  H  L  L  R  V  V  L  P  L  L  S  L  S  P  A  G  L  A  A
   1  ATGCATCTCCTCCGGGTTGTTCTGCCGCTTCTGTCCCTTTCACCCGCTGGCCTGGCAGCT
         P  A  S  P  A  A  P  T  V  T  I  A  S  P  A  A  T  I  V  G
  61  CCGGCCTCGCCAGCTGCGCCTACCGTCACGATCGCATCTCCCGCTGCCACCATTGTTGGG
         S  S  G  K  V  E  K  F  N  A  I  P  F  A  Q  P  P  T  G  P
 121  TCGTCCGGGAAGGTAGAGAAGTTCAACGCCATCCCCTTCGCCCAGCCACCCACGGGCCCC
         L  R  L  K  P  P  Q  P  I  Q  K  P  L  G  T  I  D  G  T  G
 181  CTGCGTCTGAAGCCTCCCCAGCCAATACAGAAGCCCCTGGGCACTATTGACGGCACGGGT
         S  A  K  S  C  P  Q  F  F  F  S  T  D  N  S  E  F  P  G  S
 241  AGCGCCAAGTCGTGTCCTCAGTTCTTTTTTTCGACGGACAACAGCGAGTTTCCGGGGTCC
         V  A  G  L  L  A  N  L  P  L  F  Q  T  V  T  N  A  G  E  D
 301  GTCGCCGGTCTCTTGGCCAACCTTCCCCTCTTCCAGACCGTGACAAATGCTGGAGAGGAT
         C  L  T  L  N  V  A  R  P  S  G  T  A  P  G  A  K  L  P  V
 361  TGCCTGACCCTGAATGTGGCGCGTCCGTCCGGCACAGCTCCAGGCGCGAAGCTGCCCGTC
         L  V  W  I  Y  G  G  G  F  E  L  G  A  T  A  T  Y  D  A  T
 421  CTCGTGTGGATCTACGGCGGCGGCTTCGAGCTGGGCGCCACGGCCACGTACGATGCGACC
         S  L  V  A  S  S  I  D  L  G  M  P  I  V  F  V  A  M  N  Y
 481  TCGCTAGTGGCAAGCTCGATCGACCTGGGTATGCCAATTGTCTTTGTCGCGATGAACTAT
         R  T  G  G  F  G  F  L  P  G  K  E  I  L  A  D  G  A  A  N
 541  CGAACGGGGGGATTTGGCTTCCTGCCGGGGAAGGAGATCCTGGCGGATGGGGCGGCCAAC
         L  G  L  L  D  Q  R  L  A  L  Q  W  V  A  D  N  I  A  A  F
 601  CTGGGGCTCTTGGACCAACGCCTGGCCCTGCAGTGGGTGGCGGACAACATTGCGGCCTTT
         G  G  D  P  D  K  V  T  I  W  G  E  S  A  G  S  I  S  V  F
 661  GGCGGCGACCCAGACAAGGTCACCATCTGGGGTGAGTCCGCGGGATCCATCTCGGTCTTC
         D  H  M  I  L  Y  D  G  D  N  T  Y  K  G  K  P  L  F  R  G
 721  GATCACATGATCCTGTATGATGGCGACAATACCTACAAAGGGAAGCCGCTGTTCCGGGGC
         G  I  M  N  S  G  S  V  I  P  A  D  P  V  D  G  V  K  G  Q
 781  GGCATCATGAACTCGGGTAGCGTGATCCCGGCGGATCCCGTAGACGGGGTCAAGGGGCAG
         Q  V  Y  D  A  V  V  D  Y  A  G  C  S  S  A  A  D  T  L  E
 841  CAGGTATATGATGCGGTTGTGGACTATGCCGGCTGCTCATCGGCCGCGGACACGCTGGAA
         C  L  R  G  L  D  Y  T  D  F  L  N  A  A  N  A  V  P  G  I
 901  TGTCTGCGCGGATTGGACTATACCGACTTTCTGAATGCGGCCAACGCGGTGCCAGGCATC
         L  S  Y  H  S  V  A  L  S  Y  L  P  R  P  D  G  K  A  I  T
 961  CTAAGCTACCATTCCGTGGCCCTGTCATACCTGCCTCGACCCGACGGCAAGGCGATCACG
         A  S  P  D  I  L  V  K  T  G  K  Y  A  A  V  P  I  I  I  G
1021  GCCAGCCCAGACATTTTGGTCAAAACCGGCAAATACGCCGCCGTGCCCATCATTATCGGC
         D  Q  E  D  E  G  T  L  F  A  L  F  Q  S  N  I  T  T  T  K
1081  GACCAGGAGGATGAAGGGACTTTATTCGCGCTCTTCCAGTCCAACATCACCACCACCAAA
         Q  V  V  D  Y  L  A  K  Y  Y  F  F  E  A  T  R  D  Q  L  E
1141  CAAGTGGTGGACTATCTGGCCAAGTATTACTTCTTTGAGGCGACGCGCGACCAGCTCGAG
         E  L  V  A  T  Y  P  D  V  T  T  D  G  S  P  F  R  T  G  I
1201  GAGCTGGTGGCGACGTATCCGGACGTCACCACCGACGGCTCACCCTTCCGCACGGGCATT
         F  N  N  W  Y  P  Q  F  K  R  L  A  A  L  L  G  D  L  T  F
1321  ACGCTGACGCGCCGAGCCTACCTCAAATACGTGACGGAGCTTCACCCCAGCCTGCCCTGC
         W  S  Y  L  S  S  Y  D  Y  G  T  P  I  M  G  T  F  H  G  S
1381  TGGTCATACCTGTCATCGTACGACTACGGGACGCCCATTATGGGCACCTTCCACGGCAGT
         D  I  L  Q  V  F  Y  G  I  L  P  N  Y  A  S  R  A  F  H  T
1441  GATATTCTGCAGGTGTTTTATGGCATTCTGCCCAATTACGCGTCGCGCGCGTTCCACACC
         Y  Y  F  S  F  V  Y  D  L  D  P  N  S  R  R  G  S  L  M  E
```

Fig. 2A

```
1501    TACTATTTCAGCTTCGTATACGATCTCGATCCGAACTCTCGCCGGGGTAGTCTTATGGAA
         W  P  R  W  N  D  D  Q  Q  L  M  Q  V  F  N  N  R  G  A  L
1561    TGGCCGCGGTGGAACGACGACCAGCAGCTGATGCAGGTCTTCAACAATCGGGGGCCTTG
         L  A  D  D  F  R  N  D  T  Y  N  F  I  L  E  N  V  D  S  F
1621    CTGGCCGATGATTTCCGCAATGACACGTACAACTTTATTCTGGAGAACGTGGATTCGTTC
         H  I  *
1681    CATATCTAG
```

Fig. 2B

```
      M  R  F  S  G  F  V  S  G  L  G  L  G  L  L  T  A  V  S  A
  1 ATGAGATTCTCTGGTTTCGTCTCTGGCCTCGGCCTTGGTCTCTTGACTGCTGTATCTGCC
      S  P  A  A  F  P  A  P  A  S  I  P  D  P  I  P  A  P  V  A
 61 AGTCCAGCTGCCTTTCCTGCTCCGGCCTCGATCCCTGACCCTATACCTGCACCTGTCGCA
      P  A  S  P  A  I  E  E  R  A  A  K  V  T  V  A  V  P  S  G
121 CCTGCTTCACCAGCTATTGAAGAACGAGCAGCCAAAGTCACAGTTGCTGTTCCTTCCGGT
      T  V  V  G  S  S  S  G  K  V  D  S  F  R  G  I  P  F  A  D
181 ACAGTCGTTGGATCTAGCTCTGGAAAGGTTGATTCCTTCAGAGGCATTCCTTTCGCCGAT
      P  P  T  G  S  L  R  L  R  P  P  K  R  L  S  K  S  L  G  T
241 CCACCAACTGGCTCTCTGCGCCTCAGACCTCCCAAGAGACTATCCAAGTCTCTAGGAACT
      F  D  A  S  G  L  S  A  A  A  C  P  Q  M  F  I  S  S  G  G
301 TTCGATGCCTCGGGTCTCAGTGCTGCAGCATGTCCTCAGATGTTCATCTCGAGTGGAGGT
      Q  S  V  I  T  E  F  L  S  D  F  L  A  V  P  F  L  T  P  I
361 CAAAGTGTTATCACAGAGTTCCTCTCTGACTTTCTGGCTGTCCCTTTCCTCACGCCCATC
      T  G  Q  E  D  C  L  T  I  T  V  Q  R  P  A  G  T  K  A  G
421 ACTGGCCAAGAGGACTGCCTCACCATAACAGTCCAGCGTCCTGCTGGTACCAAAGCTGGT
      D  K  L  P  V  L  F  W  I  F  G  G  G  F  E  L  G  S  S  A
481 GACAAGCTCCCCGTTCTCTTCTGGATCTTTGGCGGCGGCTTCGAATTAGGCTCAAGTGCT
      M  Y  D  G  T  S  L  L  S  T  A  I  D  Q  S  Q  P  F  I  Y
541 ATGTATGACGGCACAAGCCTCTTGTCTACTGCCATAGATCAAAGTCAGCCTTTTATCTAC
      V  A  V  N  Y  R  V  A  G  F  G  F  M  P  G  A  E  I  K  K
601 GTTGCTGTCAACTACCGAGTCGCCGGCTTCGGATTCATGCCCGGTGCTGAGATCAAGAAG
      D  G  S  S  N  L  G  L  L  D  Q  R  M  G  L  E  W  V  A  D
661 GACGGAAGCTCCAACCTGGGTCTGCTCGACCAGCGCATGGGTCTCGAGTGGGTGGCTGAC
      N  I  A  S  F  G  G  D  P  E  K  V  T  I  W  G  E  S  A  G
721 AATATTGCTTCCTTTGGTGGTGATCCTGAAAAGGTCACTATCTGGGGAGAGTCTGCTGGC
      S  I  S  V  L  D  Q  M  V  L  Y  G  G  D  A  S  Y  K  G  K
781 TCCATCTCCGTGCTTGATCAGATGGTTCTCTACGGTGGTGATGCCAGTTATAAGGGCAAG
      S  L  F  R  G  A  I  M  N  S  G  T  I  V  P  A  E  P  V  D
```

Fig. 8A

```
 841   TCTCTTTTCCGAGGTGCCATCATGAACTCTGGCACTATTGTCCCAGCTGAGCCTGTGGAT
        S   D   K   A   Q   S   I   Y   D   T   V   V   K   T   G   G   C   S   G   A
 901   AGTGACAAGGCACAGTCTATCTATGACACTGTTGTCAAGACTGGAGGCTGCTCTGGTGCT
        S   D   T   L   E   C   L   R   G   L   S   Y   D   K   F   L   N   A   A   N
 961   TCTGATACTCTGGAGTGTCTGCGTGGTCTGAGCTATGACAAGTTCCTGAACGCTGCAAAC
        S   V   P   G   L   L   S   Y   N   S   L   A   L   S   Y   L   P   R   P   D
1021   TCGGTCCCAGGATTGCTGTCGTACAACTCACTGGCTTTGTCCTATCTTCCTCGGCCAGAT
        G   K   V   L   P   K   S   P   D   V   L   V   A   T   G   Q   Y   H   A   V
1081   GGCAAGGTCCTACCCAAAAGCCCCGACGTGCTTGTTGCAACGGGACAATACCACGCAGTG
        P   M   I   T   G   C   Q   E   D   E   G   T   L   F   A   L   F   Q   P   N
1141   CCCATGATCACCGGATGCCAGGAGGACGAAGGAACCCTCTTTGCACTATTCCAACCCAAC
        V   T   T   T   S   R   L   V   E   Y   L   Q   N   L   Y   F   T   Q   A   T
1201   GTGACCACTACATCCAGATTGGTCGAATACTTGCAGAACCTGTACTTTACACAGGCCACA
        K   Q   Q   V   T   A   L   V   N   T   Y   P   T   T   L   S   T   G   S   P
1261   AAGCAACAGGTGACTGCTCTAGTAAACACATATCCCACCACCCTCAGCACAGGCAGTCCC
        Y   R   T   G   L   L   N   E   V   F   P   G   F   K   R   R   A   A   I   L
1321   TATCGAACAGGCCTGCTCAACGAGGTCTTTCCCGGTTTCAAGCGCCGTGCAGCCATTCTA
        G   D   L   V   V   S   L   T   R   R   I   F   L   Q   A   A   A   N   S   N
1381   GGCGATCTAGTCGTCTCCCTTACACGTCGCATCTTCCTCCAGGCCGCCGCCAACAGCAAC
        P   D   V   P   S   W   Y   L   A   S   Y   D   Y   G   T   P   I   L   G
1441   CCAGACGTTCCATCATGGTCATACCTCGCAAGCTACGATTACGGCACACCCATTCTGGGA
        T   F   H   G   S   D   L   L   Q   V   F   Y   G   L   L   P   N   N   A   M
1501   ACATTCCACGGGTCTGACCTTTTACAAGTCTTTTATGGTCTGTTGCCCAATAACGCTATG
        R   S   V   R   T   Y   Y   F   N   F   V   Y   N   L   D   P   N   K   G   V
1561   CGGAGTGTCCGAACGTACTACTTCAACTTTGTATACAACCTTGATCCCAACAAGGGCGTT
        T   K   Y   A   K   W   P   E   W   K   E   S   K   K   L   M   W   F   E   T
1621   ACCAAGTACGCCAAGTGGCCCGAGTGGAAGGAGAGCAAGAAGCTCATGTGGTTTGAGACG
        A   N   K   N   S   I   I   N   D   D   F   R   Q   D   S   Y   E   F   I   A
1681   GCGAATAAGAACAGCATTATAAACGATGACTTTAGACAGGATTCGTATGAGTTTATTGCG
        A   N   A   G   A   L   V   V   *
1741   GCGAATGCCGGTGCTTTGGTGGTATGA
```

Fig. 8B

```
        M  K  A  S  I  L  S  A  F  S  A  V  F  L  T  V  A  G  S  Q
  1   ATGAAAGCCTCCATTCTTTCGGCTTTCTCGGCCGTCTTTCTGACGGTAGCCGGTTCCCAG
        V  I  R  Q  Q  L  P  P  V  D  P  R  L  P  Q  L  D  L  S  R
 61   GTAATACGACAACAGCTGCCACCGGTGGACCCGCGGCTCCCACAACTGGATCTCTCTCGC
        F  E  V  P  I  D  L  R  E  P  E  D  G  L  K  L  E  A  R  K
121   TTCGAGGTTCCAATTGATCTGAGAGAACCAGAAGATGGCTTGAAGCTCGAGGCACGTAAG
        D  A  P  T  V  K  L  E  D  G  S  I  I  T  G  S  V  L  A  D
181   GATGCACCTACAGTAAAGCTGGAAGATGGGTCCATAATCACAGGCTCAGTTCTTGCCGAC
        V  E  S  F  K  G  I  P  F  A  E  P  P  L  G  D  L  R  M  R
241   GTCGAATCTTTTAAGGGCATCCCCTTTGCGGAACCCCCACTGGGTGACCTGCGCATGAGG
        P  P  V  R  L  E  K  P  L  G  K  F  D  A  S  M  R  I  S  P
301   CCACCCGTACGACTTGAAAAGCCGCTCGGCAAATTCGATGCCTCGATGCGCATTTCACCG
        Q  C  P  Q  M  F  F  S  S  S  T  G  R  M  L  T  Q  V  I  G
361   CAATGCCCACAGATGTTCTTCTCCTCCTCAACCGGCCGTATGTTGACGCAGGTCATTGGG
        N  L  L  N  K  G  L  F  Q  K  I  L  D  S  T  E  D  C  L  N
421   AATCTGCTCAACAAGGGGCTTTTCCAAAAGATCCTGGATTCTACCGAGGACTGCTTAAAC
        I  N  V  Q  R  P  K  G  V  K  A  G  D  K  L  P  V  L  F  W
481   ATCAACGTGCAAAGGCCTAAAGGTGTCAAGGCTGGTGACAAACTGCCCGTACTGTTCTGG
        I  F  G  G  G  F  E
541   ATTTTTGGCGGTGGTTTCGAGGTACGTCGTTCTCTAGTGTGATGTCATGTTCTAGGCAGG
601   CGCGCTTGTTGCGGAGCGCGGCTCCCGAGACGTTGCATATCCGTGCTACCTACCGTACCA
                                            L  G  S  N  A  M  Y  S  G  T
661   TGCCGCTAACAGTATACCTTTGTAAACAGCTTGGTAGCAATGCAATGTACTCTGGCACGC
        P  I  L  T  R  A  M  E  Q  G  Q  P  F  I  F  V  G  V  N  Y
721   CGATCCTTACGAGGGCAATGGAACAAGGCCAGCCCTTCATTTTCGTCGGGGTCAACTACC
        R  V  G  G  F  G  F  M  P  G  E  E  I  Q  A  E  G  S  G  N
781   GCGTAGGAGGCTTTGGCTTCATGCCAGGCGAGGAGATCCAGGCCGAGGGCTCTGGAAACG
        A  G  L  L  D  Q  R  M  G  M  E  W  V  A  D  N  I  E  A  F
841   CTGGGCTGCTGGACCAGCGCATGGGCATGGAATGGGTTGCCGACAATATCGAGGCTTTCG
        G  G  D  P  D  K  V  T  I  W  G  E  S  A  G  A  I  S  V  F
901   GTGGCGATCCCGACAAGGTCACCATCTGGGGCGAATCTGCCGGCGCCATCTCGGTATTTG
        D  Q  M  A  L  Y  D  G  N  A  T  Y  K  G  K  P  L  F  R  A
961   ACCAGATGGCCCTGTACGACGGCAACGCTACCTACAAAGGCAAGCCGCTCTTCCGCGCCG
        A  I  M  N  S  G  S  I  I  P  A  D  P  V  D  C  P  K  G  R
1021  CCATCATGAACTCTGGCAGCATTATCCCTGCTGATCCCGTCGATTGTCCCAAGGGCAGGG
        E  V  Y  N  Q  V  V  K  A  G  G  C  S  G  R  S  D  T  L  K
1081  AGGTTTACAACCAAGTCGTCAAAGCGGGTGGTTGCTCGGGTCGATCCGATACGCTGAAAT
        C  L  R  E  L  P  Y  E  K  F  L  K  A  A  N  A  P  P  G  L
1141  GTCTCCGCGAACTCCCCTACGAGAAGTTCCTTAAGGCAGCCAACGCGCCTCCTGGCCTCC
        L  S  Y  N  S  V  A  L  S  Y  L  P  R  P  D  G  K  V  L  R
1201  TGAGTTACAACTCGGTCGCGCTATCATACCTCCCCAGGCCCGACGGCAAAGTTCTCAGGG
        A  S  P  D  V  L  L  G  Q  R  Y  Y  P  V  P  M  I  I  G
1261  CCAGCCCTGACGTTCTACTGCTTGGGCAGAGATACTATCCCGTCCCCATGATTATCGGCG
        D  Q  E  D  E  G  S  I  F  A  L  F  Q  H  N  L  T  N  T  E
1321  ACCAGGAGGATGAGGGTAGCATTTTTGCCCTCTTCCAGCACAACCTCACCAACACTGAGA
        M  L  V  G  Y  L  K  E  I  F  F  P  A  T  D  I  Q  K  I  K
1381  TGCTCGTCGGCTATCTCAAAGAAATCTTCTTCCCAGCAACCGATATTCAAAAAATCAAGG
        D  L  V  K  S  Y  P  D  D  P  R  E  G  S  P  F  R  T  G  K
1441  ATCTGGTAAAATCATACCCCGACGACCCGCGCGAGGGCTCGCCCTTCCGCACCGGTAAAT
        L  N  Q  V  Y  P  Q  F  K  R  L  A  A  I  L  G  D  I  T  F
1501  TGAACCAGGTGTACCCTCAATTCAAGCGTCTCGCCGCCATCCTTGGTGACATCACCTTTA
        T  L  T  R  R  L  F  L  F  A  S  A  T  L  H  P  D  V  P  S
```

Fig. 12A

```
1561    CCCTGACGCGCCGGCTGTTCCTCTTCGCCTCGGCGACCCTGCACCCAGACGTCCCGTCGT
        W  S  Y  L  S  S  Y  D  Y  G  T  P  I  A  G  T  F  H  G  S
1621    GGTCCTACCTGTCCAGCTACGACTACGGCACCCCCATCGCGGGAACCTTTCACGGCAGCG
        D  L  L  Q  V  F  Y  G  I  L  P  N  Y  A  S  R  T  T  V  S
1681    ATCTCCTGCAGGTCTTTTACGGAATCCTGCCCAACTACGCCAGCAGGACCACCGTCTCGT
        Y  Y  T  N  F  L  Y  N  L  D  P  N  E  G  I  K  V  Q  H  W
1741    ACTACACAAACTTCCTGTACAACCTGGACCCCAACGAGGGCATCAAGGTCCAGCACTGGC
        P  K  W  M  E  N  Q  E  L  L  N  M  N  A  N  D  A  K  L  I
1801    CCAAGTGGATGGAGAACCAGGAGCTGCTGAACATGAATGCCAACGATGCCAAGTTGATCC
        P  D  N  F  R  N  E  S  Y  N  Y  L  L  A  N  F  L  S  F  Y
1861    CGGACAACTTTAGAAACGAGAGTTACAACTACCTGCTGGCCAACTTCCTCAGCTTTTACA
        I  *
1921    TTTAA
```

Fig. 12B

```
         M  R  Q  S  I  F  Q  S  L  M  L  A  A  G  A  S  A  A  V  L
   1  ATGCGTCAATCCATCTTCCAGTCACTGATGCTGGCCGCCGGCGCCTCGGCGGCCGTCCTG
         P  R  A  S  Q  G  P  T  V  Q  V  A  N  G  S  Y  Y  G  V  H
  61  CCCCGGGCCAGCCAAGGCCCGACCGTGCAGGTCGCCAACGGCTCCTACTATGGCGTGCAC
         N  S  F  Y  D  Q  D  L  F  L  G  M  P  Y  A  Q  P  P  V  G
 121  AACTCTTTTTACGACCAAGACCTGTTCCTCGGCATGCCCTACGCCCAGCCGCCCGTCGGC
         N  L  R  F  R  V  P  E  P  L  N  S  T  W  D  G  V  R  N  A
 181  AACCTCCGCTTCCGCGTTCCGGAGCCCCTGAACTCGACCTGGGACGGCGTGCGGAACGCG
         T  E  Y  G  Y  A  C  I  G  Y  G  S  D  Q  W  V  L  G  N  Y
 241  ACCGAGTACGGCTACGCGTGTATCGGCTACGGTTCGGACCAGTGGGTGCTGGGCAACTAT
         V  N  E  D  C  L  T  V  N  V  V  R  P  A  G  V  P  A  N  A
 301  GTCAACGAGGACTGCTTGACTGTCAACGTCGTCCGTCCCGCGGGCGTCCCGGCTAATGCC
         K  L  P  V  A  V  W  I  H  G  G  G  Y  F  M  G  S  G  S  D
 361  AAGCTCCCCGTTGCCGTCTGGATTCATGGCGGTGGTTACTTCATGGGCAGCGGCAGTGAT
         P  R  Y  N  T  S  F  L  V  K  E  S  V  E  M  G  T  P  M  V
 421  CCCAGGTACAACACCTCGTTCCTCGTCAAGGAGTCCGTGGAGATGGGCACCCCGATGGTG
         A  V  T  L  N  Y  R  L  S  A  W  G  F  I  F  G  K  E  V  Q
 481  GCCGTGACCCTCAACTACCGCCTGTCCGCCTGGGGCTTCATCTTCGGCAAGGAGGTGCAG
         A  A  G  Q  T  N  I  G  M  R  D  Q  R  L  A  L  H  W  I  Q
 541  GCGGCCGGCCAGACCAACATCGGCATGCGCGACCAGCGCCTGGCCCTGCACTGGATCCAG
         E  N  I  D  A  F  G  G  D  K  S  K  V  T  I  F  G  E  S  A
 601  GAGAACATCGACGCCTTTGGCGGCGACAAGAGCAAGGTGACCATCTTTGGCGAGTCGGCG
         G  G  N  S  V  G  T  Q  L  I  A  Y  G  G  R  D  D  G  L  F
 661  GGCGGCAACTCGGTCGGCACGCAGCTCATCGCTTACGGCGGACGCGACGACGGACTCTTC
         R  A  A  I  S  Q  S  G  A  P  S  G  L  G  R  M  T  T  P  E
 721  CGCGCCGCCATCTCCCAGTCCGGCGCGCCCTCGGGGCTGGGCCGCATGACCACGCCCGAG
         S  W  Q  P  A  Y  D  A  L  V  S  K  A  G  C  A  D  A  A  D
 781  TCGTGGCAGCCCGCCTACGACGCCCTGGTCAGCAAGGCCGGGTGCGCCGACGCCGCCGAC
         S  L  D  C  L  R  G  V  P  A  D  A  L  N  A  F  I  N  S  T
 841  TCGCTCGACTGCCTGCGCGGCGTCCCCGCCGACGCCCTCAACGCCTTTATCAACTCGACC
         D  V  L  A  G  P  A  R  P  V  I  D  G  D  L  L  T  E  V  G
 901  GACGTGCTCGCCGGCCCCGCGCGCCCCGTCATCGACGGCGACTTGCTGACCGAGGTCGGC
         T  T  S  L  R  A  G  R  F  V  H  V  P  Y  L  I  G  A  N  A
 961  ACCACCTCGCTCCGCGCCGGCCGCTTCGTCCACGTCCCCTACCTGATCGGCGCCAACGCC
         D  E  G  V  S  F  G  V  R  G  I  N  T  E  D  E  F  V  A  M
1021  GACGAGGGCGTGTCCTTTGGCGTCCGCGGCATCAACACCGAGGACGAGTTCGTCGCCATG
         V  Q  R  S  N  A  G  L  T  R  D  D  A  L  A  I  A  A  L  Y
1081  GTGCAGCGCAGCAACGCCGGGCTCACGCGCGACGACGCCCTCGCCATCGCGGCCCTCTAC
         P  D  D  P  D  Q  G  I  P  S  T  L  K  G  R  P  L  D  R  T
1141  CCCGACGACCCGGACCAGGGCATCCCCTCCACGCTCAAGGGCCGTCCTGGACCGGACCTG
         Q  P  L  L  G  S  M  W  K  R  S  A  A  Y  G  G  D  P  I  M
1201  CAGCCCCTGCTGGGCTCGATGTGGAAGCGCAGCGCGGCCTACGGCGGAGACCCCATCATG
         H  A  P  R  R  I  A  N  E  E  W  A  R  H  G  V  P  S  Y  S
1261  CACGCCCCCGCCGCATCGCGAACGAGGAGTGGGCCAGGCACGGCGTGCCGTCTTACAGC
         Y  H  F  D  V  L  T  N  G  I  P  D  Y  A  G  S  T  H  F  Q
1321  TACCACTTTGACGTTCTGACAAACGGCATTCCGGACTATGCTGGGTCGACCCACTTCCAG
         E  V  A  F  M  F  N  N  T  G  G  L  G  Y  G  N  A  V  S  V
1381  GAGGTTGCCTTCATGTTCAACAACACCGGCGGTCTGGGCTACGGCAACGCCGTGTCGGTG
         N  P  F  G  G  M  P  E  S  L  K  S  L  S  H  M  M  A  R  M
```

Fig. 14A

```
1441  AACCCGTTTGGCGGCATGCCCGAGTCCTTGAAGAGCTTGTCGCACATGATGGCGAGGATG
        W  I  S  F  V  V  N  L  D  P  N  H  I  G  I  G  R  W  I  P
1501  TGGATCAGCTTCGTGGTCAACCTGGACCCGAACCACATTGGTATTGGTAGGTGGATCCCT
        S  V  M  R  M  M  L  L  W  I  C  G  Y  *
1561  TCCGTCATGAGAATGATGTTGTTGTTATGGATTTGCGGGTACTAA
```

Fig. 14B

```
     M  K  G  F  S  N  A  L  L  A  T  S  L  A  L  L  G  R  V  S  A
    ATGAAGGGCTTTTCCAACGCTCTCCTCGCTACCTCCCTGGCCCTCCTTGGCCGGGTCTCTGCT
     A  P  A  E  P  P  T  Q  V  L  H  K  R  A  A  P  T  V  T  I  S
    GCCCCAGCTGAGCCCCCTACCCAGGTGTTGCACAAGCGAGCCGCCCCGACTGTCACCATTTCC
     T  G  T  I  V  G  A  N  G  I  L  T  E  A  F  N  G  I  P  Y  A
    ACCGGTACGATTGTGGGTGCTAACGGCATCCTCACTGAGGCCTTCAACGGAATCCCCTACGCC
     L  P  P  T  G  N  L  R  L  K  P  P  V  R  L  K  S  S  L  G  V
    CTTCCTCCGACCGGCAACCTTCGCCTCAAGCCTCCCGTGAGACTTAAGTCGTCTCTGGGTGTC
     F  D  A  S  G  I  G  P  A  C  P  Q  F  L  A  D  T  S  S  N  E
    TTTGATGCGTCTGGCATCGGCCCTGCTTGCCCCCAGTTCCTTGCTGACACCTCGTCGAACGAG
     F  L  P  Q  V  I  D  K  I  V  N  T  Q  L  F  K  T  I  L  N  V
    TTTCTGCCTCAGGTTATCGATAAGATCGTTAACACGCAGCTTTTCAAGACTATACTCAACGTC
     K  E  D  C  L  T  I  S  V  T  R  P  K  G  T  K  A  G  D  K  L
    AAGGAGGACTGCTTGACCATCTCGGTCACTCGTCCCAAGGGCACCAAGGCTGGTGATAAGCTC
     P  V  L  F  W  I  F  G  G  G  F  E
    CCCGTCCTTTTCTGGATCTTTGGTGGTGGTTTCGAAGTGAGAAATCCAGCTTATATACGCGAT
                                   L  G  S  A  S  M  Y  D  G  A  P  L
    GTAATGAACAAGTGCTAAAACTTCACAGCTCGGATCGGCGTCCATGTACGATGGCGCTCCCTA
     V  T  N  A  I  N  M  G  K  P  Y  V  V  Y  V  A  V  N  Y  R  V  G
    GTCACCAACGCTATCAACATGGGTAAGCCGTACGTCTACGTTGCCGTCAACTACCGTGTCGGT
     G  F  G  F  M  P  G  K  E  I  L  K  D  G  S  S  N  L  G  H  L
    GGCTTTGGTTTCATGCCCGGAAAGGAGATCCTTAAGGACGGCTCTTCCAACTGGGTCACCTT
     D  Q  R  M  G  L  Q  W  V  A  D  N  I  A  A  F  G  G  D  P  D
    GACCAGCGCATGGGCCTCCAGTGGGTTGCCGACAACATTGCTGCCTTCGGCGGTGACCCAGAC
     K  V  T  I  W  G  E  S  A  G  A  M  S  V  F  N  Q  M  S  L  Y
    AAGGTCACTATCTGGGGCGAGTCCGCCGGTGCCATGTCCGTTTTCAACCAGATGTCTCTCTAT
     D  G  D  N  T  Y  N  G  K  P  L  F  R  G  A  I  M  N  S  G  S
    GACGGTGACAACACGTACAACGGCAAGCCCCTTTTCCGTGGCGCCATCATGAACTCTGGTTCC
     I  V  P  A  G  P  V  D  C  P  K  G  Q  K  V  Y  D  T  V  V  K
    ATCGTCCCCGCCGGCCCCGTCGACTGCCCCAAGGGCCAGAAAGTCTACGACACCGTCGTCAAG
     N  A  G  C  S  G  A  A  D  T  L  A  C  L  R  A  L  P  Y  E  T
    AACGCCGGCTGCTCTGGTGCTGCTGACACCCTTGCTTGCCTGCGCGCTCTTCCCTACGAGACT
     F  L  K  A  A  N  S  V  P  G  I  L  S  Y  N  S  V  A  L  S  Y
    TTTCTCAAGGCCGCTAACTCCGTGCCTGGGATTCTGTCGTACAACTCCGTTGCTCTTTCTTAC
     L  P  R  P  D  G  K  A  L  T  Q  S  A  D  K  L  M  A  K  K
    CTCCCGCGACCCGATGGCAAGGCTTTGACTCAGAGCGCCGATAAGCTCATGCTCGCTAAGAAG
     Y  A  A  V  P  M  I  I  G  D  Q  E  D  E  G  T  L  F  S  L  F
    TACGCCGCCGTCCCCATGATCATCGGCGATCAAGAGGATGAGGGCACTCTCTTCTCCCTCTTC
     Q  S  N  I  T  T  T  S  K  L  V  S  Y  L  N  D  I  F  F  N  D
    CAGAGCAACATCACCACCACCAGCAAGCTGGTCAGCTACCTCAACGATATCTTCTTCAACGAC
     A  T  E  S  Q  I  K  S  L  V  S  T  Y  S  T  L  I  S  A  G  S
    GCCACCGAGTCGCAGATTAAGTCTCTCGTCTCGACCTACAGTACCCTTATCTCCGCCGGCTCG
     P  F  G  T  G  L  F  N  E  I  Y  P  G  F  K  R  L  A  A  I  L
    CCCTTTGGCACCGGCCTCTTCAACGAGATTTACCCCGGCTTCAAGCGCCTGGCCGCCATTCTT
     G  D  L  I  F  T  L  S  R  R  I  F  L  D  A  A  T  T  L  N  P
    GGCGATCTCATCTTCACCCTCAGCCGCCGCATCTTTCTCGACGCCGCCACCACTCTCAACCCC
     S  V  P  A  W  S  Y  L  A  S  Y  N  F  G  T  P  I  L  G  T  F
    TCGGTGCCCGCCTGGTCGTATCTTGCGTCTTACAACTTTGGCACACCCATCCTTGGAACCTTT
     H  A  S  D  I  L  Q  V  F  Y  G  I  L  P  N  Y  A  S  K  S  I
    CACGCCTCCGATATCCTGCAGGTGTTCTACGGCATCCTGCCCAACTACGCCAGCAAAAGCATC
```

Fig. 16A

```
Q   S   Y   Y   A   N   F   V   Y   N   L   D   P   N   D   A   S   G   G   T   S
CAGTCTTACTACGCCAACTTTGTTTACAACCTTGACCCCAACGACGCCTCCGGTGGCACTTCC
  S   K   S   K   V   S   Q   D   W   P   Q   W   Q   K   E   R   K   L   V   Q   F
TCTAAGAGCAAGGTCAGCCAGGATTGGCCGCAATGGCAGAAGGAGAGAAAGCTGGTCCAGTTC
  F   S   D   Y   A   G   Y   L   A   D   D   F   R   S   D   S   C   N   W   I   K
TTTTCGGACTATGCCGGATATCTTGCGGATGATTTCGCTCTGATTCGTGTAACTGGATTAAG
  A   N   L   D   A   L   H   I   *
GCTAATCTTGATGCTCTTCACATCTAA
```

Fig. 16B

```
SEQUENCE LISTING

<160> NUMBER OF SEQ ID NOS: 38

<210> SEQ ID NO 1
<211> LENGTH: 1689
<212> TYPE: DNA
<213> ORGANISM: Aspergillus fumigatus

<400> SEQUENCE: 1
atgcatctcc tccgggttgt tctgccgctt ctgtcccttt cacccgctgg cctggcagct      60
ccggcctcgc cagctgcgcc taccgtcacg atcgcatctc ccgctgccac cattgttggg     120
tcgtccggga aggtagagaa gttcaacgcc atcccctccg cccagccacc cacgggcccc     180
ctgcgtctga agcctcccca gccaatacag aagcccctgg gcactattga cggcacgggt     240
agcgccaagt cgtgtcctca gttcttttt tcgacggaca cagcgagtt tccggggtcc       300 gtcgccggtc tcttggccaa ccttcccctc ttccagaccg tgacaaatgc tggagaggat     360
tgcctgaccc tgaatgtggc gcgtccgtcc ggcacagctc caggcgcgaa gctgcccgtc     420
ctcgtgtgga tctacggcgg cggcttcgag ctgggcgcca cggccacgta cgatgcgacc     480
tcgctagtgg caagctcgat cgacctgggt atgccaattg tctttgtcgc gatgaactat     540
cgaacggggg gatttggctt cctgccgggg aaggagatcc tggcggatgg ggcggccaac     600
ctggggctct tggaccaacg cctggccctg cagtgggtgg cggacaacat tgcggccttt     660
ggcggcgacc cagacaaggt caccatctgg ggtgagtccg cgggatccat ctcggtcttc     720
gatcacatga tcctgtatga tggcgacaat acctacaaag ggaagccgct gttccgggc      780 ggcatcatga actcgggtag cgtgatcccg gcggatcccg tagacggggt caaggggcag     840
caggtatatg atgcggttgt ggactatgcc ggctgctcat cggccgcgga cacgctggaa     900
tgtctgcgcg gattggacta taccgacttt ctgaatgcgg ccaacgcggt gccaggcatc     960
ctaagctacc attccgtggc cctgtcatac ctgcctcgac ccgacggcaa ggcgatcacg    1020
gccagcccag acattttggt caaaaccggc aaatacgccg ccgtgcccat cattatcggc    1080
gaccaggagg atgaagggac tttattcgcg ctcttccagt ccaacatcac caccaccaaa    1140
caagtggtgg actatctggc caagtattac ttctttgagg cgacgcgcga ccagctcgag    1200
gagctggtgg cgacgtatcc ggacgtcacc accgacggct caccccttccg cacgggcatt    1260 ttcaacaact ggtatccgca gttcaaacgg ttggcagccc tgctgggcga tctcaccttc    1320
acgctgacgc gccgagccta cctcaaatac gtgacggagc ttcaccccag cctgccctgc    1380
tggtcatacc tgtcatcgta cgactacggg acgcccatta tgggcacctt ccacggcagt    1440
```

```
gatattctgc aggtgtttta tggcattctg cccaattacg cgtcgcgcgc gttccacacc      1500
tactatttca gcttcgtata cgatctcgat ccgaactctc gccggggtag tcttatggaa      1560
tggccgcggt ggaacgacga ccagcagctg atgcaggtct tcaacaatcg ggggccttg       1620 ctggccgatg atttccgcaa tgacacgtac aactttattc tggagaacgt ggattcgttc      1680
catatctag                                                              1689
```

<210> SEQ ID NO 2
<211> LENGTH: 562
<212> TYPE: PRT
<213> ORGANISM: Aspergillus fumigatus

<400> SEQUENCE: 2

```
Met His Leu Leu Arg Val Val Leu Pro Leu Ser Leu Ser Pro Ala
1               5                   10                  15

Gly Leu Ala Ala Pro Ala Ser Pro Ala Ala Pro Thr Val Thr Ile Ala
            20                  25                  30

Ser Pro Ala Ala Thr Ile Val Gly Ser Gly Lys Val Glu Lys Phe
        35                  40                  45

Asn Ala Ile Pro Phe Ala Gln Pro Pro Thr Gly Pro Leu Arg Leu Lys
    50                  55                  60

Pro Pro Gln Pro Ile Gln Lys Pro Leu Gly Thr Ile Asp Gly Thr
65                  70                  75                  80

Ser Ala Lys Ser Cys Pro Gln Phe Phe Phe Ser Thr Asp Asn Ser Glu
                85                  90                  95

Phe Pro Gly Ser Val Ala Gly Leu Leu Ala Asn Leu Pro Leu Phe Gln
            100                 105                 110

Thr Val Thr Asn Ala Gly Glu Asp Cys Leu Thr Leu Asn Val Ala Arg
        115                 120                 125

Pro Ser Gly Thr Ala Pro Gly Ala Lys Leu Pro Val Leu Val Trp Ile
    130                 135                 140

Tyr Gly Gly Gly Phe Glu Leu Gly Ala Thr Ala Thr Tyr Asp Ala Thr
145                 150                 155                 160

Ser Leu Val Ala Ser Ser Ile Asp Leu Gly Met Pro Ile Val Phe Val
                165                 170                 175

Ala Met Asn Tyr Arg Thr Gly Gly Phe Gly Phe Leu Pro Gly Lys Glu
            180                 185                 190

Ile Leu Ala Asp Gly Ala Ala Asn Leu Gly Leu Leu Asp Gln Arg Leu
        195                 200                 205

Ala Leu Gln Trp Val Ala Asp Asn Ile Ala Ala Phe Gly Gly Asp Pro
    210                 215                 220

Asp Lys Val Thr Ile Trp Gly Glu Ser Ala Gly Ser Ile Ser Val Phe
225                 230                 235                 240

Asp His Met Ile Leu Tyr Asp Gly Asp Asn Thr Tyr Lys Gly Lys Pro
                245                 250                 255

Leu Phe Arg Gly Gly Ile Met Asn Ser Gly Ser Val Ile Pro Ala Asp
            260                 265                 270

Pro Val Asp Gly Val Lys Gly Gln Gln Val Tyr Asp Ala Val Asp
        275                 280                 285

Tyr Ala Gly Cys Ser Ser Ala Ala Asp Thr Leu Glu Cys Leu Arg Gly
    290                 295                 300

Leu Asp Tyr Thr Asp Phe Leu Asn Ala Ala Asn Ala Val Pro Gly Ile
305                 310                 315                 320

Leu Ser Tyr His Ser Val Ala Leu Ser Tyr Leu Pro Arg Pro Asp Gly
```

```
                    325                 330                 335
Lys Ala Ile Thr Ala Ser Pro Asp Ile Leu Val Lys Thr Gly Lys Tyr
                340                 345                 350
Ala Ala Val Pro Ile Ile Gly Asp Gln Glu Asp Glu Gly Thr Leu
                355                 360                 365
Phe Ala Leu Phe Gln Ser Asn Ile Thr Thr Thr Lys Gln Val Val Asp
            370                 375                 380
Tyr Leu Ala Lys Tyr Tyr Phe Glu Ala Thr Arg Asp Gln Leu Glu
385                 390                 395                 400
Glu Leu Val Ala Thr Tyr Pro Asp Val Thr Thr Asp Gly Ser Pro Phe
                405                 410                 415
Arg Thr Gly Ile Phe Asn Asn Trp Tyr Pro Gln Phe Lys Arg Leu Ala
                420                 425                 430
Ala Leu Leu Gly Asp Leu Thr Phe Thr Leu Thr Arg Arg Ala Tyr Leu
            435                 440                 445
Lys Tyr Val Thr Glu Leu His Pro Ser Leu Pro Cys Trp Ser Tyr Leu
            450                 455                 460
Ser Ser Tyr Asp Tyr Gly Thr Pro Ile Met Gly Thr Phe His Gly Ser
465                 470                 475                 480
Asp Ile Leu Gln Val Phe Tyr Gly Ile Leu Pro Asn Tyr Ala Ser Arg
                485                 490                 495
Ala Phe His Thr Tyr Tyr Phe Ser Phe Val Tyr Asp Leu Asp Pro Asn
                500                 505                 510
Ser Arg Arg Gly Ser Leu Met Glu Trp Pro Arg Trp Asn Asp Asp Gln
            515                 520                 525
Gln Leu Met Gln Val Phe Asn Asn Arg Gly Ala Leu Leu Ala Asp Asp
            530                 535                 540
Phe Arg Asn Asp Thr Tyr Asn Phe Ile Leu Glu Asn Val Asp Ser Phe
545                 550                 555                 560
His Ile

<210> SEQ ID NO 3
<211> LENGTH: 1767
<212> TYPE: DNA
<213> ORGANISM: Fusarium graminearum

<400> SEQUENCE: 3
atgagattct ctggtttcgt ctctggcctc ggccttggtc tcttgactgc tgtatctgcc     60
agtccagctg cctttcctgc tccggcctcg atccctgacc ctatacctgc acctgtcgca    120
cctgcttcac cagctattga gaacgagca gccaaagtca cagttgctgt tccttccggt    180
acagtcgttg atctagctc tggaaaggtt gattccttca gaggcattcc tttcgccgat    240
ccaccaactg gctctctgcg cctcagacct cccaagagac tatccaagtc tctaggaact    300
ttcgatgcct cgggtctcag tgctgcagca tgtcctcaga tgttcatctc gagtggaggt    360
caaagtgtta tcacagagtt cctctctgac tttctggctg tcccttccct cacgcccatc    420
actggccaag aggactgcct caccataaca gtccagcgtc ctgctggtac caaagctggt    480
gacaagctcc ccgttctctt ctggatcttt ggcggcggct tcgaattagg ctcaagtgct    540
atgtatgacg gcacaagcct cttgtctact gccatagatc aaagtcagcc ttttatctac    600
gttgctgtca actaccgagt cgccggcttc ggattcatgc ccggtgctga gatcaagaag    660
gacggaagct ccaacctggg tctgctcgac cagcgcatgg gtctcgagtg ggtggctgac    720
aatattgctt cctttggtgg tgatcctgaa aaggtcacta tctggggaga gtctgctggc    780
```

-continued

```
tccatctccg tgcttgatca gatggttctc tacggtggtg atgccagtta agggcaag       840
tctcttttcc gaggtgccat catgaactct ggcactattg tcccagctga gcctgtggat      900
agtgacaagg cacagtctat ctatgacact gttgtcaaga ctggaggctg ctctggtgct      960
tctgatactc tggagtgtct gcgtggtctg agctatgaca agttcctgaa cgctgcaaac     1020
tcggtcccag gattgctgtc gtacaactca ctggctttgt cctatcttcc tcggccagat     1080
ggcaaggtcc tacccaaaag ccccgacgtg cttgttgcaa cgggacaata ccacgcagtg     1140
cccatgatca ccggatgcca ggaggacgaa ggaaccctct ttgcactatt ccaacccaac     1200
gtgaccacta catccagatt ggtcgaatac ttgcagaacc tgtactttac acaggccaca     1260
aagcaacagg tgactgctct agtaaacaca tatcccacca ccctcagcac aggcagtccc     1320
tatcgaacag gctgctcaa cgaggtcttt cccggtttca gcgccgtgc agccattcta       1380
ggcgatctag tcgtctccct tacacgtcgc atcttcctcc aggccgccgc caacagcaac     1440
ccagacgttc catcatggtc atacctcgca agctacgatt acggcacacc cattctggga    1500
acattccacg ggtctgacct tttacaagtc ttttatggtc tgttgcccaa taacgctatg    1560
cggagtgtcc gaacgtacta cttcaacttt gtatacaacc ttgatcccaa caagggcgtt    1620
accaagtacg ccaagtggcc cgagtggaag gagagcaaga agctcatgtg gtttgagacg    1680
gcgaataaga acagcattat aaacgatgac tttagacagg attcgtatga gtttattgcg    1740
gcgaatgccg gtgctttggt ggtatga                                         1767
```

<210> SEQ ID NO 4
<211> LENGTH: 588
<212> TYPE: PRT
<213> ORGANISM: Fusarium graminearum

<400> SEQUENCE: 4

```
Met Arg Phe Ser Gly Phe Val Ser Gly Leu Gly Leu Gly Leu Leu Thr
1               5                   10                  15

Ala Val Ser Ala Ser Pro Ala Ala Phe Pro Ala Pro Ala Ser Ile Pro
            20                  25                  30

Asp Pro Ile Pro Ala Pro Val Ala Pro Ala Ser Pro Ala Ile Glu Glu
        35                  40                  45

Arg Ala Ala Lys Val Thr Val Ala Val Pro Ser Gly Thr Val Val Gly
    50                  55                  60

Ser Ser Gly Lys Val Asp Ser Phe Arg Gly Ile Pro Phe Ala Asp
65                  70                  75                  80

Pro Pro Thr Gly Ser Leu Arg Leu Arg Pro Pro Lys Arg Leu Ser Lys
                85                  90                  95

Ser Leu Gly Thr Phe Asp Ala Ser Gly Leu Ser Ala Ala Ala Cys Pro
            100                 105                 110

Gln Met Phe Ile Ser Ser Gly Gly Gln Ser Val Ile Thr Glu Phe Leu
        115                 120                 125

Ser Asp Phe Leu Ala Val Pro Phe Leu Thr Pro Ile Thr Gly Gln Glu
    130                 135                 140

Asp Cys Leu Thr Ile Thr Val Gln Arg Pro Ala Gly Thr Lys Ala Gly
145                 150                 155                 160

Asp Lys Leu Pro Val Leu Phe Trp Ile Phe Gly Gly Phe Glu Leu
                165                 170                 175

Gly Ser Ser Ala Met Tyr Asp Gly Thr Ser Leu Leu Ser Thr Ala Ile
            180                 185                 190

Asp Gln Ser Gln Pro Phe Ile Tyr Val Ala Val Asn Tyr Arg Val Ala
        195                 200                 205
```

Gly Phe Gly Phe Met Pro Gly Ala Glu Ile Lys Lys Asp Gly Ser Ser
            210                 215                 220

Asn Leu Gly Leu Leu Asp Gln Arg Met Gly Leu Glu Trp Val Ala Asp
225                 230                 235                 240

Asn Ile Ala Ser Phe Gly Gly Asp Pro Glu Lys Val Thr Ile Trp Gly
                245                 250                 255

Glu Ser Ala Gly Ser Ile Ser Val Leu Asp Gln Met Val Leu Tyr Gly
            260                 265                 270

Gly Asp Ala Ser Tyr Lys Gly Lys Ser Leu Phe Arg Gly Ala Ile Met
        275                 280                 285

Asn Ser Gly Thr Ile Val Pro Ala Glu Pro Val Asp Ser Asp Lys Ala
290                 295                 300

Gln Ser Ile Tyr Asp Thr Val Lys Thr Gly Gly Cys Ser Gly Ala
305                 310                 315                 320

Ser Asp Thr Leu Glu Cys Leu Arg Gly Leu Ser Tyr Asp Lys Phe Leu
                325                 330                 335

Asn Ala Ala Asn Ser Val Pro Gly Leu Leu Ser Tyr Asn Ser Leu Ala
            340                 345                 350

Leu Ser Tyr Leu Pro Arg Pro Asp Gly Lys Val Leu Pro Lys Ser Pro
        355                 360                 365

Asp Val Leu Val Ala Thr Gly Gln Tyr His Ala Val Pro Met Ile Thr
370                 375                 380

Gly Cys Gln Glu Asp Glu Gly Thr Leu Phe Ala Leu Phe Gln Pro Asn
385                 390                 395                 400

Val Thr Thr Thr Ser Arg Leu Val Glu Tyr Leu Gln Asn Leu Tyr Phe
                405                 410                 415

Thr Gln Ala Thr Lys Gln Val Thr Ala Leu Val Asn Thr Tyr Pro
            420                 425                 430

Thr Thr Leu Ser Thr Gly Ser Pro Tyr Arg Thr Gly Leu Leu Asn Glu
        435                 440                 445

Val Phe Pro Gly Phe Lys Arg Arg Ala Ala Ile Leu Gly Asp Leu Val
450                 455                 460

Val Ser Leu Thr Arg Arg Ile Phe Leu Gln Ala Ala Asn Ser Asn
465                 470                 475                 480

Pro Asp Val Pro Ser Trp Ser Tyr Leu Ala Ser Tyr Asp Tyr Gly Thr
                485                 490                 495

Pro Ile Leu Gly Thr Phe His Gly Ser Asp Leu Leu Gln Val Phe Tyr
            500                 505                 510

Gly Leu Leu Pro Asn Asn Ala Met Arg Ser Val Arg Thr Tyr Tyr Phe
        515                 520                 525

Asn Phe Val Tyr Asn Leu Asp Pro Asn Lys Gly Val Thr Lys Tyr Ala
530                 535                 540

Lys Trp Pro Glu Trp Lys Glu Ser Lys Lys Leu Met Trp Phe Glu Thr
545                 550                 555                 560

Ala Asn Lys Asn Ser Ile Ile Asn Asp Asp Phe Arg Gln Asp Ser Tyr
                565                 570                 575

Glu Phe Ile Ala Ala Asn Ala Gly Ala Leu Val Val
            580                 585

<210> SEQ ID NO 5
<211> LENGTH: 1925
<212> TYPE: DNA
<213> ORGANISM: Magnaporthe grisea

<400> SEQUENCE: 5

-continued

```
atgaaagcct ccattctttc ggctttctcg gccgtctttc tgacggtagc cggttcccag      60
gtaatacgac aacagctgcc accggtggac ccgcggctcc cacaactgga tctctctcgc     120
ttcgaggttc caattgatct gagagaacca gaagatggct tgaagctcga ggcacgtaag     180
gatgcaccta cagtaaagct ggaagatggg tccataatca caggctcagt tcttgccgac     240
gtcgaatctt ttaagggcat cccctttgcg gaacccccac tgggtgacct gcgcatgagg     300
ccacccgtac gacttgaaaa gccgctcggc aaattcgatg cctcgatgcg catttcaccg     360
caatgcccac agatgttctt ctcctcctca accggccgta tgttgacgca ggtcattggg     420
aatctgctca acaaggggct tttccaaaag atcctggatt ctaccgagga ctgcttaaac     480
atcaacgtgc aaaggcctaa aggtgtcaag gctggtgaca aactgcccgt actgttctgg     540
atttttggcg gtggtttcga ggtacgtcgt tctctagtgt gatgtcatgt tctaggcagg     600
cgcgcttgtt gcggagcgcg gctcccgaga cgttgcatat ccgtgctacc taccgtacca     660
tgccgctaac agtatacctt tgtaaacagc ttggtagcaa tgcaatgtac tctggcacgc     720
cgatccttac gagggcaatg gaacaaggcc agcccttcat tttcgtcggg gtcaactacc     780
gcgtaggagg ctttggcttc atgccaggcg aggagatcca ggccgagggc tctggaaacg     840
ctgggctgct ggaccagcgc atgggcatgg aatgggttgc cgacaatatc gaggctttcg     900
gtggcgatcc cgacaaggtc accatctggg gcgaatctgc cggcgccatc tcggtatttg     960
accagatggc cctgtacgac ggcaacgcta cctacaaagg caagccgctc ttccgcgccg    1020
ccatcatgaa ctctggcagc attatccctg ctgatcccgt cgattgtccc aagggcaggg    1080
aggtttacaa ccaagtcgtc aaagcgggtg gttgctcggg tcgatccgat acgctgaaat    1140
gtctccgcga actcccctac gagaagttcc ttaaggcagc caacgcgcct cctggcctcc    1200
tgagttacaa ctcggtcgcg ctatcatacc tccccaggcc cgacggcaaa gttctcaggg    1260
ccagccctga cgttctactg cttgggcaga gatactatcc cgtccccatg attatcggcg    1320
accaggagga tgagggtagc atttttgccc tcttccagca caacctcacc aacactgaga    1380
tgctcgtcgg ctatctcaaa gaaatcttct tcccagcaac cgatattcaa aaaatcaagg    1440
atctggtaaa atcatacccc gacgacccgc gcgagggctc gcccttccgc accggtaaat    1500
tgaaccaggt gtaccctcaa ttcaagcgtc tcgccgccat ccttggtgac atcaccttta    1560
ccctgacgcg ccggctgttc ctcttcgcct cggcgaccct gcacccagac gtcccgtcgt    1620
ggtcctacct gtccagctac gactacggca cccccatcgc gggaaccttt cacggcagcg    1680
atctcctgca ggtcttttac ggaatcctgc ccaactacgc cagcaggacc accgtctcgt    1740
actacacaaa cttcctgtac aacctggacc ccaacgaggg catcaaggtc cagcactggc    1800
ccaagtggat ggagaaccag gagctgctga acatgaatgc caacgatgcc aagttgatcc    1860
cggacaactt tagaaacgag agttacaact acctgctggc caacttcctc agcttttaca    1920
tttaa                                                                1925
```

<210> SEQ ID NO 6
<211> LENGTH: 598
<212> TYPE: PRT
<213> ORGANISM: Magnaporthe grisea

<400> SEQUENCE: 6

```
Met Lys Ala Ser Ile Leu Ser Ala Phe Ser Ala Val Phe Leu Thr Val
1               5                   10                  15

Ala Gly Ser Gln Val Ile Arg Gln Gln Leu Pro Pro Val Asp Pro Arg
            20                  25                  30
```

```
Leu Pro Gln Leu Asp Leu Ser Arg Phe Glu Val Pro Ile Asp Leu Arg
            35                  40                  45

Glu Pro Glu Asp Gly Leu Lys Leu Glu Ala Arg Lys Asp Ala Pro Thr
    50                  55                  60

Val Lys Leu Glu Asp Gly Ser Ile Ile Thr Gly Ser Val Leu Ala Asp
 65                  70                  75                  80

Val Glu Ser Phe Lys Gly Ile Pro Phe Ala Glu Pro Pro Leu Gly Asp
                85                  90                  95

Leu Arg Met Arg Pro Pro Val Arg Leu Glu Lys Pro Leu Gly Lys Phe
            100                 105                 110

Asp Ala Ser Met Arg Ile Ser Pro Gln Cys Pro Gln Met Phe Phe Ser
            115                 120                 125

Ser Ser Thr Gly Arg Met Leu Thr Gln Val Ile Gly Asn Leu Leu Asn
            130                 135                 140

Lys Gly Leu Phe Gln Lys Ile Leu Asp Ser Thr Glu Asp Cys Leu Asn
145                 150                 155                 160

Ile Asn Val Gln Arg Pro Lys Gly Val Lys Ala Gly Asp Lys Leu Pro
                165                 170                 175

Val Leu Phe Trp Ile Phe Gly Gly Phe Glu Leu Gly Ser Asn Ala
            180                 185                 190

Met Tyr Ser Gly Thr Pro Ile Leu Thr Arg Ala Met Glu Gln Gly Gln
        195                 200                 205

Pro Phe Ile Phe Val Gly Val Asn Tyr Arg Val Gly Gly Phe Gly Phe
        210                 215                 220

Met Pro Gly Glu Glu Ile Gln Ala Glu Gly Ser Gly Asn Ala Gly Leu
225                 230                 235                 240

Leu Asp Gln Arg Met Gly Met Glu Trp Val Ala Asp Asn Ile Glu Ala
                245                 250                 255

Phe Gly Gly Asp Pro Asp Lys Val Thr Ile Trp Gly Glu Ser Ala Gly
            260                 265                 270

Ala Ile Ser Val Phe Asp Gln Met Ala Leu Tyr Asp Gly Asn Ala Thr
        275                 280                 285

Tyr Lys Gly Lys Pro Leu Phe Arg Ala Ala Ile Met Asn Ser Gly Ser
    290                 295                 300

Ile Ile Pro Ala Asp Pro Val Asp Cys Pro Lys Gly Arg Glu Val Tyr
305                 310                 315                 320

Asn Gln Val Val Lys Ala Gly Gly Cys Ser Gly Arg Ser Asp Thr Leu
                325                 330                 335

Lys Cys Leu Arg Glu Leu Pro Tyr Glu Lys Phe Leu Lys Ala Ala Asn
            340                 345                 350

Ala Pro Pro Gly Leu Leu Ser Tyr Asn Ser Val Ala Leu Ser Tyr Leu
        355                 360                 365

Pro Arg Pro Asp Gly Lys Val Leu Arg Ala Ser Pro Asp Val Leu Leu
    370                 375                 380

Leu Gly Gln Arg Tyr Tyr Pro Val Pro Met Ile Ile Gly Asp Gln Glu
385                 390                 395                 400

Asp Glu Gly Ser Ile Phe Ala Leu Phe Gln His Asn Leu Thr Asn Thr
                405                 410                 415

Glu Met Leu Val Gly Tyr Leu Lys Glu Ile Phe Phe Pro Ala Thr Asp
            420                 425                 430

Ile Gln Lys Ile Lys Asp Leu Val Lys Ser Tyr Pro Asp Asp Pro Arg
        435                 440                 445

Glu Gly Ser Pro Phe Arg Thr Gly Lys Leu Asn Gln Val Tyr Pro Gln
```

```
                450                 455                 460
Phe Lys Arg Leu Ala Ala Ile Leu Gly Asp Ile Thr Phe Thr Leu Thr
465                 470                 475                 480

Arg Arg Leu Phe Leu Phe Ala Ser Ala Thr Leu His Pro Asp Val Pro
                485                 490                 495

Ser Trp Ser Tyr Leu Ser Ser Tyr Asp Tyr Gly Thr Pro Ile Ala Gly
                500                 505                 510

Thr Phe His Gly Ser Asp Leu Leu Gln Val Phe Tyr Gly Ile Leu Pro
            515                 520                 525

Asn Tyr Ala Ser Arg Thr Thr Val Ser Tyr Tyr Thr Asn Phe Leu Tyr
530                 535                 540

Asn Leu Asp Pro Asn Glu Gly Ile Lys Val Gln His Trp Pro Lys Trp
545                 550                 555                 560

Met Glu Asn Gln Glu Leu Leu Asn Met Asn Ala Asn Asp Ala Lys Leu
                565                 570                 575

Ile Pro Asp Asn Phe Arg Asn Glu Ser Tyr Asn Tyr Leu Leu Ala Asn
                580                 585                 590

Phe Leu Ser Phe Tyr Ile
            595
```

<210> SEQ ID NO 7
<211> LENGTH: 1605
<212> TYPE: DNA
<213> ORGANISM: Magnaporthe grisea

<400> SEQUENCE: 7

```
atgcgtcaat ccatcttcca gtcactgatg ctggccgccg cgcctcggc ggccgtcctg      60
ccccgggcca gccaaggccc gaccgtgcag gtcgccaacg gctcctacta tggcgtgcac     120
aactcttttt acgaccaaga cctgttcctc ggcatgccct acgcccagcc gcccgtcggc     180
aacctccgct ccgcgttccc ggagcccctg aactcgacct gggacggcgt gcggaacgcg     240
accgagtacg gctacgcgtg tatcggctac ggttcggacc agtgggtgct gggcaactat     300
gtcaacgagg actgcttgac tgtcaacgtc gtccgtcccg cgggcgtccc ggctaatgcc     360
aagctccccg ttgccgtctg gattcatggc ggtggttact tcatgggcag cggcagtgat     420
cccaggtaca cacctcgtt cctcgtcaag gagtccgtgg agatgggcac cccgatggtg     480
gccgtgaccc tcaactaccg cctgtccgcc tggggcttca tcttcggcaa ggaggtgcag     540
gcggccggcc agaccaacat cggcatgcgc gaccagcgcc tggccctgca ctggatccag     600
gagaacatcg acgcctttgg cggcgacaag agcaaggtga ccatctttgg cgagtcggcg     660
ggcggcaact cggtcggcac gcagctcatc gcttacggcg acgcgacga cggactcttc     720
cgcgccgcca tctcccagtc cggcgcgccc tcggggctgg ccgcatgac cacgcccgag     780
tcgtggcagc ccgcctacga cgccctggtc agcaaggccg ggtgcgccga cgccgccgac     840
tcgctcgact gcctgcgcgg cgtccccgcc gacgccctca cgcctttat caactcgacc     900
gacgtgctcg ccggccccgc gcgccccgtc atcgacggcg acttgctgac cgaggtcggc     960
accacctcgc tccgcgccgg ccgcttcgtc acgtcccct acctgatcgg cgccaacgcc    1020
gacgagggcg tgtcctttgg cgtccgcggc atcaacaccg aggacgagtt cgtcgccatg    1080
gtgcagcgca gcaacgccgg gctcacgcgc gacgacgccc tcgccatcgc ggccctctac    1140
cccgacgacc cggaccaggg catcccctcc acgctcaagg gcgtcctgg accggacctg    1200
cagcccctgc tgggctcgat gtggaagcgc agcgcggcct acggcggaga ccccatcatg    1260
cacgccccc gccgcatcgc gaacgaggag tgggccaggc acggcgtgcc gtcttacagc    1320
```

-continued

```
taccactttg acgttctgac aaacggcatt ccggactatg ctgggtcgac ccacttccag   1380
gaggttgcct tcatgttcaa caacaccggc ggtctgggct acggcaacgc cgtgtcggtg   1440
aacccgtttg gcggcatgcc cgagtccttg aagagcttgt cgcacatgat ggcgaggatg   1500
tggatcagct tcgtggtcaa cctggacccg aaccacattg gtattggtag gtggatccct   1560
tccgtcatga gaatgatgtt gttgttatgg atttgcgggt actaa                   1605

<210> SEQ ID NO 8
<211> LENGTH: 534
<212> TYPE: PRT
<213> ORGANISM: Magnaporthe grisea

<400> SEQUENCE: 8

Met Arg Gln Ser Ile Phe Gln Ser Leu Met Leu Ala Ala Gly Ala Ser
1               5                   10                  15

Ala Ala Val Leu Pro Arg Ala Ser Gln Gly Pro Thr Val Gln Val Ala
            20                  25                  30

Asn Gly Ser Tyr Tyr Gly Val His Asn Ser Phe Tyr Asp Gln Asp Leu
        35                  40                  45

Phe Leu Gly Met Pro Tyr Ala Gln Pro Pro Val Gly Asn Leu Arg Phe
    50                  55                  60

Arg Val Pro Glu Pro Leu Asn Ser Thr Trp Asp Gly Val Arg Asn Ala
65                  70                  75                  80

Thr Glu Tyr Gly Tyr Ala Cys Ile Gly Tyr Gly Ser Asp Gln Trp Val
                85                  90                  95

Leu Gly Asn Tyr Val Asn Glu Asp Cys Leu Thr Val Asn Val Val Arg
            100                 105                 110

Pro Ala Gly Val Pro Ala Asn Ala Lys Leu Pro Val Ala Val Trp Ile
        115                 120                 125

His Gly Gly Gly Tyr Phe Met Gly Ser Gly Ser Asp Pro Arg Tyr Asn
    130                 135                 140

Thr Ser Phe Leu Val Lys Glu Ser Val Glu Met Gly Thr Pro Met Val
145                 150                 155                 160

Ala Val Thr Leu Asn Tyr Arg Leu Ser Ala Trp Gly Phe Ile Phe Gly
                165                 170                 175

Lys Glu Val Gln Ala Ala Gly Gln Thr Asn Ile Gly Met Arg Asp Gln
            180                 185                 190

Arg Leu Ala Leu His Trp Ile Gln Glu Asn Ile Asp Ala Phe Gly Gly
        195                 200                 205

Asp Lys Ser Lys Val Thr Ile Phe Gly Glu Ser Ala Gly Gly Asn Ser
    210                 215                 220

Val Gly Thr Gln Leu Ile Ala Tyr Gly Gly Arg Asp Asp Gly Leu Phe
225                 230                 235                 240

Arg Ala Ala Ile Ser Gln Ser Gly Ala Pro Ser Gly Leu Gly Arg Met
                245                 250                 255

Thr Thr Pro Glu Ser Trp Gln Pro Ala Tyr Asp Ala Leu Val Ser Lys
            260                 265                 270

Ala Gly Cys Ala Asp Ala Ala Asp Ser Leu Asp Cys Leu Arg Gly Val
        275                 280                 285

Pro Ala Asp Ala Leu Asn Ala Phe Ile Asn Ser Thr Asp Val Leu Ala
    290                 295                 300

Gly Pro Ala Arg Pro Val Ile Asp Gly Asp Leu Leu Thr Glu Val Gly
305                 310                 315                 320

Thr Thr Ser Leu Arg Ala Gly Arg Phe Val His Val Pro Tyr Leu Ile
```

```
                    325                 330                 335
Gly Ala Asn Ala Asp Glu Gly Val Ser Phe Gly Val Arg Gly Ile Asn
            340                 345                 350
Thr Glu Asp Glu Phe Val Ala Met Val Gln Arg Ser Asn Ala Gly Leu
        355                 360                 365
Thr Arg Asp Asp Ala Leu Ala Ile Ala Ala Leu Tyr Pro Asp Asp Pro
    370                 375                 380
Asp Gln Gly Ile Pro Ser Thr Leu Lys Gly Arg Pro Gly Pro Asp Leu
385                 390                 395                 400
Gln Pro Leu Leu Gly Ser Met Trp Lys Arg Ser Ala Ala Tyr Gly Gly
            405                 410                 415
Asp Pro Ile Met His Ala Pro Arg Arg Ile Ala Asn Glu Glu Trp Ala
        420                 425                 430
Arg His Gly Val Pro Ser Tyr Ser Tyr His Phe Asp Val Leu Thr Asn
    435                 440                 445
Gly Ile Pro Asp Tyr Ala Gly Ser Thr His Phe Gln Glu Val Ala Phe
    450                 455                 460
Met Phe Asn Asn Thr Gly Gly Leu Gly Tyr Gly Asn Ala Val Ser Val
465                 470                 475                 480
Asn Pro Phe Gly Gly Met Pro Glu Ser Leu Lys Ser Leu Ser His Met
            485                 490                 495
Met Ala Arg Met Trp Ile Ser Phe Val Val Asn Leu Asp Pro Asn His
        500                 505                 510
Ile Gly Ile Gly Arg Trp Ile Pro Ser Val Met Arg Met Leu Leu
    515                 520                 525
Leu Trp Ile Cys Gly Tyr
    530

<210> SEQ ID NO 9
<211> LENGTH: 1792
<212> TYPE: DNA
<213> ORGANISM: Neurospora crassa

<400> SEQUENCE: 9
atgaagggct tttccaacgc tctcctcgct acctccctgg ccctccttgg ccgggtctct      60
gctgccccag ctgagccccc tacccaggtg ttgcacaagc gagccgcccc gactgtcacc     120
atttccaccg gtacgattgt gggtgctaac ggcatcctca ctgaggcctt caacggaatc     180
ccctacgccc ttcctccgac cggcaacctt cgcctcaagc ctcccgtgag acttaagtcg     240
tctctgggtg tctttgatgc gtctggcatc ggccctgctt gccccagtt ccttgctgac      300 acctcgtcga cgagtttct gcctcaggtt atcgataaga tcgttaacac gcagcttttc     360
aagactatac tcaacgtcaa ggaggactgc ttgaccatct cggtcactcg tcccaagggc     420
accaaggctg tgataagct ccccgtcctt ttctggatct tggtggtgg tttcgaagtg      480 agaaatccag cttatatacg cgatgtaatg aacaagtgct aaaacttcac agctcggatc     540
ggcgtccatg tacgatggcg ctcccctagt caccaacgct atcaacatgg gtaagccgta     600
cgtctacgtt gccgtcaact accgtgtcgg tggctttggt ttcatgcccg aaaggagat      660 ccttaaggac ggctcttcca acttgggtca ccttgaccag cgcatgggcc tccagtgggt     720
tgccgacaac attgctgcct cggcggtga cccagacaag gtcactatct ggggcgagtc      780
cgccggtgcc atgtccgttt tcaaccagat gtctctctat gacggtgaca cacgtacaa      840 cggcaagccc ttttccgtg cgccatcat gaactctggt tccatcgtcc ccgcggccc      900 cgtcgactgc cccaagggcc agaaagtcta cgacaccgtc gtcaagaacg ccggctgctc     960
```

```
tggtgctgct gacacccttg cttgcctgcg cgctcttccc tacgagactt ttctcaaggc    1020
cgctaactcc gtgcctggga ttctgtcgta caactccgtt gctctttctt acctcccgcg    1080
acccgatggc aaggctttga ctcagagcgc cgataagctc atgctcgcta agaagtacgc    1140
cgccgtcccc atgatcatcg gcgatcaaga ggatgagggc actctcttct ccctcttcca    1200
gagcaacatc accaccacca gcaagctggt cagctacctc aacgatatct tcttcaacga    1260
cgccaccgag tcgcagatta agtctctcgt ctcgacctac agtacccctta tctccgccgg    1320 ctcgcccttt ggcaccggcc tcttcaacga gatttacccc ggcttcaagc gcctggccgc    1380
cattcttggc gatctcatct tcaccctcag ccgccgcatc tttctcgacg ccgccaccac    1440
tctcaacccc tcggtgcccg cctggtcgta tcttgcgtct acaactttg gcacacccat    1500 ccttggaacc tttcacgcct ccgatatcct gcaggtgttc tacggcatcc tgcccaacta    1560
cgccagcaaa agcatccagt cttactacgc caactttgtt tacaaccttg accccaacga    1620
cgcctccggt ggcacttcct ctaagagcaa ggtcagccag gattggccgc aatggcagaa    1680
ggagagaaag ctggtccagt tcttttcgga ctatgccgga tatcttgcgg atgatttccg    1740
ctctgattcg tgtaactgga ttaaggctaa tcttgatgct cttcacatct aa            1792
```

<210> SEQ ID NO 10
<211> LENGTH: 578
<212> TYPE: PRT
<213> ORGANISM: Neurospora crassa

<400> SEQUENCE: 10

```
Met Lys Gly Phe Ser Asn Ala Leu Leu Ala Thr Ser Leu Ala Leu Leu
1               5                   10                  15

Gly Arg Val Ser Ala Ala Pro Ala Glu Pro Pro Thr Gln Val Leu His
            20                  25                  30

Lys Arg Ala Ala Pro Thr Val Thr Ile Ser Thr Gly Thr Ile Val Gly
        35                  40                  45

Ala Asn Gly Ile Leu Thr Glu Ala Phe Asn Gly Ile Pro Tyr Ala Leu
    50                  55                  60

Pro Pro Thr Gly Asn Leu Arg Leu Lys Pro Pro Val Arg Leu Lys Ser
65                  70                  75                  80

Ser Leu Gly Val Phe Asp Ala Ser Gly Ile Gly Pro Ala Cys Pro Gln
                85                  90                  95

Phe Leu Ala Asp Thr Ser Ser Asn Glu Phe Leu Pro Gln Val Ile Asp
            100                 105                 110

Lys Ile Val Asn Thr Gln Leu Phe Lys Thr Ile Leu Asn Val Lys Glu
        115                 120                 125

Asp Cys Leu Thr Ile Ser Val Thr Arg Pro Lys Gly Thr Lys Ala Gly
    130                 135                 140

Asp Lys Leu Pro Val Leu Phe Trp Ile Phe Gly Gly Gly Phe Glu Leu
145                 150                 155                 160

Gly Ser Ala Ser Met Tyr Asp Gly Ala Pro Leu Val Thr Asn Ala Ile
                165                 170                 175

Asn Met Gly Lys Pro Tyr Val Tyr Val Ala Val Asn Tyr Arg Val Gly
            180                 185                 190

Gly Phe Gly Phe Met Pro Gly Lys Glu Ile Leu Lys Asp Gly Ser Ser
        195                 200                 205

Asn Leu Gly His Leu Asp Gln Arg Met Gly Leu Gln Trp Val Ala Asp
    210                 215                 220

Asn Ile Ala Ala Phe Gly Gly Asp Pro Asp Lys Val Thr Ile Trp Gly
```

```
                225                 230                 235                 240
Glu Ser Ala Gly Ala Met Ser Val Phe Asn Gln Met Ser Leu Tyr Asp
                    245                 250                 255
Gly Asp Asn Thr Tyr Asn Gly Lys Pro Leu Phe Arg Gly Ala Ile Met
            260                 265                 270
Asn Ser Gly Ser Ile Val Pro Ala Gly Pro Val Asp Cys Pro Lys Gly
        275                 280                 285
Gln Lys Val Tyr Asp Thr Val Val Lys Asn Ala Gly Cys Ser Gly Ala
    290                 295                 300
Ala Asp Thr Leu Ala Cys Leu Arg Ala Leu Pro Tyr Glu Thr Phe Leu
305                 310                 315                 320
Lys Ala Ala Asn Ser Val Pro Gly Ile Leu Ser Tyr Asn Ser Val Ala
                325                 330                 335
Leu Ser Tyr Leu Pro Arg Pro Asp Gly Lys Ala Leu Thr Gln Ser Ala
                    340                 345                 350
Asp Lys Leu Met Leu Ala Lys Lys Tyr Ala Ala Val Pro Met Ile Ile
            355                 360                 365
Gly Asp Gln Glu Asp Glu Gly Thr Leu Phe Ser Leu Phe Gln Ser Asn
        370                 375                 380
Ile Thr Thr Thr Ser Lys Leu Val Ser Tyr Leu Asn Asp Ile Phe Phe
385                 390                 395                 400
Asn Asp Ala Thr Glu Ser Gln Ile Lys Ser Leu Val Ser Thr Tyr Ser
                405                 410                 415
Thr Leu Ile Ser Ala Gly Ser Pro Phe Gly Thr Gly Leu Phe Asn Glu
                    420                 425                 430
Ile Tyr Pro Gly Phe Lys Arg Leu Ala Ala Ile Leu Gly Asp Leu Ile
            435                 440                 445
Phe Thr Leu Ser Arg Arg Ile Phe Leu Asp Ala Ala Thr Thr Leu Asn
        450                 455                 460
Pro Ser Val Pro Ala Trp Ser Tyr Leu Ala Ser Tyr Asn Phe Gly Thr
465                 470                 475                 480
Pro Ile Leu Gly Thr Phe His Ala Ser Asp Ile Leu Gln Val Phe Tyr
                485                 490                 495
Gly Ile Leu Pro Asn Tyr Ala Ser Lys Ser Ile Gln Ser Tyr Tyr Ala
                    500                 505                 510
Asn Phe Val Tyr Asn Leu Asp Pro Asn Asp Ala Ser Gly Gly Thr Ser
            515                 520                 525
Ser Lys Ser Lys Val Ser Gln Asp Trp Pro Gln Trp Gln Lys Glu Arg
        530                 535                 540
Lys Leu Val Gln Phe Phe Ser Asp Tyr Ala Gly Tyr Leu Ala Asp Asp
545                 550                 555                 560
Phe Arg Ser Asp Ser Cys Asn Trp Ile Lys Ala Asn Leu Asp Ala Leu
                565                 570                 575
His Ile

<210> SEQ ID NO 11
<211> LENGTH: 36
<212> TYPE: DNA
<213> ORGANISM: Aspergillus fumigatus

<400> SEQUENCE: 11
acacaactgg ccatgcatct cctccgggtt gttctg                              36

<210> SEQ ID NO 12
<211> LENGTH: 40
```

```
<212> TYPE: DNA
<213> ORGANISM: Aspergillus fumigatus

<400> SEQUENCE: 12
agtcacctct agttaattaa ctagatatgg aacgaatcca                      40

<210> SEQ ID NO 13
<211> LENGTH: 22
<212> TYPE: DNA
<213> ORGANISM: Aspergillus nidulens

<400> SEQUENCE: 13
gtgccccatg atacgcctcc gg                                         22

<210> SEQ ID NO 14
<211> LENGTH: 26
<212> TYPE: DNA
<213> ORGANISM: Aspergillus nidulens

<400> SEQUENCE: 14
gagtcgtatt tccaaggctc ctgacc                                     26

<210> SEQ ID NO 15
<211> LENGTH: 24
<212> TYPE: DNA
<213> ORGANISM: Aspergillus nidulens

<400> SEQUENCE: 15
ggaggccatg aagtggacca acgg                                       24

<210> SEQ ID NO 16
<211> LENGTH: 45
<212> TYPE: DNA
<213> ORGANISM: Aspergillus niger

<400> SEQUENCE: 16
caccgtgaaa gccatgctct ttccttcgtg tagaagacca gacag                45

<210> SEQ ID NO 17
<211> LENGTH: 45
<212> TYPE: DNA
<213> ORGANISM: Aspergillus niger

<400> SEQUENCE: 17
ctggtcttct acacgaagga aagagcatgg ctttcacggt gtctg                45

<210> SEQ ID NO 18
<211> LENGTH: 44
<212> TYPE: DNA
<213> ORGANISM: Aspergillus niger

<400> SEQUENCE: 18
ctatatacac aactggattt accatgggcc gcggccgca gatc                  44

<210> SEQ ID NO 19
<211> LENGTH: 44
<212> TYPE: DNA
<213> ORGANISM: Aspergillus niger

<400> SEQUENCE: 19
gatctgcggc cgcgggccca tggtaaatcc agttgtgtat atag                 44

<210> SEQ ID NO 20
<211> LENGTH: 26
```

```
<212> TYPE: DNA
<213> ORGANISM: Aspergillus nidulens

<400> SEQUENCE: 20
gtcgacatgg tgttttgatc atttta                                              26

<210> SEQ ID NO 21
<211> LENGTH: 26
<212> TYPE: DNA
<213> ORGANISM: Aspergillus nidulens

<400> SEQUENCE: 21
ccatggccag ttgtgtatat agagga                                              26

<210> SEQ ID NO 22
<211> LENGTH: 30
<212> TYPE: DNA
<213> ORGANISM: Fusarium graminearum

<400> SEQUENCE: 22
cactgctatc accaacatga gattctctgg                                          30

<210> SEQ ID NO 23
<211> LENGTH: 35
<212> TYPE: DNA
<213> ORGANISM: Fusarium graminearum

<400> SEQUENCE: 23
ccaacaaggt atttaattaa tcataccacc aaagc                                    35

<210> SEQ ID NO 24
<211> LENGTH: 27
<212> TYPE: DNA
<213> ORGANISM: Fusarium venenatum

<400> SEQUENCE: 24
gcaggaaaga acaagtgagc aaaaggc                                             27

<210> SEQ ID NO 25
<211> LENGTH: 27
<212> TYPE: DNA
<213> ORGANISM: Fusarium venenatum

<400> SEQUENCE: 25 gcctttgct cacttgttct ttcctgc                                              27

<210> SEQ ID NO 26
<211> LENGTH: 15
<212> TYPE: DNA
<213> ORGANISM: Fusarium venenatum

<400> SEQUENCE: 26
dcctacatgt ttaat                                                          15

<210> SEQ ID NO 27
<211> LENGTH: 13
<212> TYPE: DNA
<213> ORGANISM: Fusarium venenatum

<400> SEQUENCE: 27
dtaaacatgt agg                                                            13

<210> SEQ ID NO 28
<211> LENGTH: 21
```

<212> TYPE: DNA
<213> ORGANISM: Fusarium venenatum

<400> SEQUENCE: 28
aggcctcacc catctcaaca c                                             21

<210> SEQ ID NO 29
<211> LENGTH: 21
<212> TYPE: DNA
<213> ORGANISM: Fusarium venenatum

<400> SEQUENCE: 29
acatgttggt gatagcagtg a                                             21

<210> SEQ ID NO 30
<211> LENGTH: 36
<212> TYPE: DNA
<213> ORGANISM: Magnaporthe grisea

<400> SEQUENCE: 30
acacaactgg ccatgaaagc ctccattctt tcggct                             36

<210> SEQ ID NO 31
<211> LENGTH: 40
<212> TYPE: DNA
<213> ORGANISM: Magnaporthe grisea

<400> SEQUENCE: 31
agtcacctct agttaattaa ttaaatgtaa aagctgagga                         40

<210> SEQ ID NO 32
<211> LENGTH: 24
<212> TYPE: DNA
<213> ORGANISM: Magnaporthe grisea

<400> SEQUENCE: 32
attttcccgg ctcgacgctt ctgt                                          24

<210> SEQ ID NO 33
<211> LENGTH: 27
<212> TYPE: DNA
<213> ORGANISM: Magnaporthe grisea

<400> SEQUENCE: 33
tcatgatgcg tcaatccatc ttccagt                                       27

<210> SEQ ID NO 34
<211> LENGTH: 26
<212> TYPE: DNA
<213> ORGANISM: Magnaporthe grisea

<400> SEQUENCE: 34
ggacgagttc gtcgccatgg tgcagc                                        26

<210> SEQ ID NO 35
<211> LENGTH: 26
<212> TYPE: DNA
<213> ORGANISM: Magnaporthe grisea

<400> SEQUENCE: 35
gctgcaccat ggcgacgaac tcgtcc                                        26

<210> SEQ ID NO 36
<211> LENGTH: 37

```
<212> TYPE: DNA
<213> ORGANISM: Magnaporthe grisea

<400> SEQUENCE: 36
tttaattaat tagtacccgc aaatccataa caacaac                               37

<210> SEQ ID NO 37
<211> LENGTH: 40
<212> TYPE: DNA
<213> ORGANISM: Neurospora crassa

<400> SEQUENCE: 37
acacaactgg ccatgaaggg cttttccaac gctctcctcg                            40

<210> SEQ ID NO 38
<211> LENGTH: 46
<212> TYPE: DNA
<213> ORGANISM: Neurospora crassa

<400> SEQUENCE: 38
agtcacctct agttaattaa ttagatgtga agagcatcaa gattag                     46
```

POLYPEPTIDES HAVING LIPASE ACTIVITY AND POLYNUCLEOTIDES ENCODING SAME

CROSS-REFERENCE TO RELATED APPLICATIONS

This application is a divisional application of U.S. application Ser. No. 13/440,642, filed Apr. 5, 2012, now U.S. Pat. No. 8,268,589, which is a divisional application of U.S. application Ser. No. 13/294,047, filed Nov. 10, 2011, now U.S. Pat. No. 8,158,400, which is a divisional of U.S. application Ser. No. 13/114,258, filed May 24, 2011, now U.S. Pat. No. 8,067, 218, which is a divisional application of U.S. application Ser. No. 12/944,557, filed Nov. 11, 2010, now U.S. Pat. No. 7,955, 830, which is a divisional application of U.S. application Ser. No. 12/687,696, filed Jan. 14, 2010, now U.S. Pat. No. 7,855, 172, which is a divisional application of U.S. application Ser. No. 11/255,553, filed Oct. 21, 2005, now U.S. Pat. No. 7,662, 602, which claims the benefit of U.S. Provisional Application No. 60/643,338, filed Jan. 12, 2005, which applications are incorporated herein by reference.

BACKGROUND OF THE INVENTION

1. Field of the Invention

The present invention relates to isolated polypeptides having lipase activity and isolated polynucleotides encoding the polypeptides. The invention also relates to nucleic acid constructs, vectors, and host cells comprising the polynucleotides as well as methods for producing and using the polypeptides.

2. Description of the Related Art

Triacylglycerol hydrolyzing enzymes are enzymes that catalyze the hydrolysis or formation of triglycerides. Triacylglycerol hydrolyzing enzymes are a versatile group of enzymes and often have more than one activity such as lipase, phospholipase, lysophospholipase, cholesterol esterase, cutinase, amidase, galactolipase, and other esterase type of activities. Which activity is the predominant activity will depend on the application of the enzyme and the conditions.

Triacylglycerol hydrolyzing enzymes belong to the IUBMB Enzyme Nomenclature 3.1.1. EC 3 refers to hydrolases, EC 3.1 refers to acting on ester bonds, and EC 3.1.1 refers to carboxylic ester hydrolases. Related enzymes are classified in EC 3.1.4, which refers to phosphoric diester hydrolases.

Lipases (EC 3.1.1.3) are enzymes that catalyze the hydrolysis of a wide range of carboxy esters, e.g., triglycerides to release fatty acid. Esterases (EC 3.1.1.1) are enzymes that catalyze the hydrolysis of water-soluble carboxylic esters, including short-chain fatty acid triglycerides, to produce an alcohol and a carboxylic acid anion.

Some lipases also have phospholipase activity and/or galactolipase activity (see, for example, U.S. Pat. No. 6,103, 505 and U.S. Pat. No. 6,852,346), and can also have sterol esterase activity. (3.1.1.13).

Phospholipases are enzymes that catalyze the hydrolysis of phospholipids which consist of a glycerol backbone with two fatty acids in the sn1 and sn2 positions, which is esterified with a phosphoric acid in the sn3 position. The phosphoric acid may, in turn, be esterified to an amino alcohol.

There are several types of phospholipases which catalyze the hydrolysis of the fatty acyl moieties. These phospholipases include phospholipase $A_1$ (EC 3.1.1.32), phospholipase $A_2$ (EC 3.1.1.4), and lysophospholipase (EC 3.1.1.5). Phospholipase C (EC 3.1.4.3) and phospholipase D (EC 3.1.4.4) hydrolyze the phosphoric acid group from a phospholipid, but do not hydrolyze fatty acids like phospholipase $A_1$, phospholipase $A_2$ and phospholipase B.

Phospholipase $A_1$ (EC 3.1.1.32) catalyzes the deacylation of one fatty acyl group in the sn1 position from a diacylglycerophospholipid to produce lysophospholipid and fatty acid. Phospholipase $A_2$ (EC 3.1.1.4) catalyzes the deacylation of one fatty acyl group in the sn2 position from a diacylglycerophospholipid to produce lysophospholipid and fatty acid. Lysophospholipase (EC 3.1.1.5), also known as phospholipase B, catalyzes the hydrolysis of the fatty acyl group in a lysophospholipid. Phospholipase C (EC 3.1.4.3) catalyzes the hydrolysis of phosphatidylcholine to 1,2-diacylglycerol and choline phosphate. Phospholipase D (EC 3.1.4.4) catalyzes the hydrolysis of the terminal phosphate diester bond of phosphatidylcholine to produce choline and phosphatidic acid.

Galactolipases (EC 3.1.1.26) catalyze the hydrolysis of galactolipids by removing one or two fatty acids.

Sterol esterases (3.1.1.13) catalyze the hydrolysis of sterol esters to sterol and fatty acid.

Detergents formulated with lipolytic enzymes are known to have improved properties for removing fatty stains. For example, LIPOLASE™ (Novozymes A/S, Bagsvrd, Denmark), a microbial lipase obtained from the fungus *Thermomyces lanuginosus* (also called *Humicola lanuginosa*), has been introduced into many commercial brands of detergent. Lipases have also been used in degumming processes and baking.

El-Shahed et al., 1988, *Egypt. J. Microbiol.* 23: 537-547 and Mohawed et al., 1988, *Egypt. J. Microbiol.* 23: 357-372 disclose two *Aspergillus fumigatus* lipases. WO 03/12071 discloses a gene encoding a lipase from *Aspergillus fumigatus*.

Mayordomo et al., 2000, *J. Agric. Chem.* 48: 105-109 disclose the isolation, purification, and characterization of a cold-active lipase from *Aspergillus nidulans*.

Kundu et al., 1987, *Journal of General Microbiology* 133: 149-154, disclose the isolation and characterization of an extracellular lipase from the conidia of *Neurospora crassa*.

Lipases have many commercial uses but very few lipases that work under application conditions and can be produced with high yields by microbial fermentation have been identified. There is a need in the art for alternative lipases with improved properties.

It is an object of the present invention to provide polypeptides having lipase activity and polynucleotides encoding the polypeptides.

SUMMARY OF THE INVENTION

The present invention relates to isolated polypeptides having lipase activity selected from the group consisting of:

(a) a polypeptide having an amino acid sequence which has at least 60% identity with the mature polypeptide of SEQ ID NO: 2, SEQ ID NO: 4, SEQ ID NO: 6, SEQ ID NO: 8, or SEQ ID NO: 10;

(b) a polypeptide which is encoded by a nucleotide sequence which hybridizes under at least medium stringency conditions with (i) the mature polypeptide coding sequence of SEQ ID NO: 1, SEQ ID NO: 3, SEQ ID NO: 5, SEQ ID NO: 7, or SEQ ID NO: 9, (ii) the cDNA sequence contained in the mature polypeptide coding sequence of SEQ ID NO: 1, SEQ ID NO: 3, SEQ ID NO: 5, SEQ ID NO: 7, or SEQ ID NO: 9, or (iii) a complementary strand of (i) or (ii); and (c) a variant comprising a conservative substitution, deletion, and/or insertion of one or more amino acids of the mature polypeptide of SEQ ID NO: 2, SEQ ID NO: 4, SEQ ID NO: 6, SEQ ID NO: 8, or SEQ ID NO: 10.

The present invention also relates to isolated polynucleotides encoding polypeptides having lipase activity, selected from the group consisting of:

(a) a polynucleotide encoding a polypeptide having an amino acid sequence which has at least 60% identity with the mature polypeptide of SEQ ID NO: 2, SEQ ID NO: 4, SEQ ID NO: 6, SEQ ID NO: 8, or SEQ ID NO: 10;

(b) a polynucleotide having at least 60% identity with the mature polypeptide coding sequence of SEQ ID NO: 1, SEQ ID NO: 3, SEQ ID NO: 5, SEQ ID NO: 7, or SEQ ID NO: 9; and (c) a polynucleotide which hybridizes under at least medium stringency conditions with (i) the mature polypeptide coding sequence of SEQ ID NO: 1, SEQ ID NO: 3, SEQ ID NO: 5, SEQ ID NO: 7, or SEQ ID NO: 9, (ii) the cDNA sequence contained in the mature polypeptide coding sequence of SEQ ID NO: 1, SEQ ID NO: 3, SEQ ID NO: 5, SEQ ID NO: 7, or SEQ ID NO: 9, or (iii) a complementary strand of (i) or (ii).

In a preferred aspect, the mature polypeptide is amino acids 21 to 562 of SEQ ID NO: 2, amino acids 25 to 588 of SEQ ID NO: 4, amino acids 21 to 598 of SEQ ID NO: 6, amino acids 19 to 534 of SEQ ID NO: 8, or amino acids 22 to 578 of SEQ ID NO: 10. In another preferred aspect, the mature polypeptide coding sequence is nucleotides 61 to 1686 of SEQ ID NO: 1, nucleotides 73 to 1764 of SEQ ID NO: 3, nucleotides 61 to 1922 of SEQ ID NO: 5, nucleotides 55 to 1602 of SEQ ID NO: 7, or nucleotides 64 to 1789 of SEQ ID NO: 9.

The present invention also relates to nucleic acid constructs, recombinant expression vectors, and recombinant host cells comprising the polynucleotides.

The present invention also relates to methods for producing such a polypeptide having lipase activity comprising: (a) cultivating a recombinant host cell comprising a nucleic acid construct comprising a polynucleotide encoding the polypeptide under conditions conducive for production of the polypeptide; and (b) recovering the polypeptide.

The present invention also relates to methods of using the polypeptides having lipase activity in detergents, degumming, and baking.

The present invention further relates to nucleic acid constructs comprising a gene encoding a protein, wherein the gene is operably linked to a nucleotide sequence encoding a signal peptide comprising or consisting of nucleotides 1 to 60 of SEQ ID NO: 1, nucleotides 1 to 72 of SEQ ID NO: 3, nucleotides 1 to 60 of SEQ ID NO: 5, nucleotides 1 to 54 of SEQ ID NO: 7, or nucleotides 1 to 63 of SEQ ID NO: 9, wherein the gene is foreign to the nucleotide sequence.

BRIEF DESCRIPTION OF THE FIGURES

FIGS. 2A and 2B show the genomic DNA sequence and the deduced amino acid sequence of an *Aspergillus fumigatus* lipase (lip1, SEQ ID NOs: 1 and 2, respectively).

FIG. 5 shows a restriction map of pBM120a.

FIGS. 8A and 8B shows the genomic DNA sequence and the deduced amino acid sequence of a *Fusarium graminearum* NRRL 31084 lipase (SEQ ID NOs: 3 and 4, respectively).

FIGS. 12A and 12B show the genomic DNA sequence and the deduced amino acid sequence of a *Magnaporthe grisea* lipase (SEQ ID NOs: 5 and 6, respectively).

FIGS. 14A and 14B show the genomic DNA sequence and the deduced amino acid sequence of a *Magnaporthe grisea* lipase (SEQ ID NOs: 7 and 8, respectively).

FIGS. 16A and 16B shows the genomic DNA sequence and the deduced amino acid sequence of a *Neurospora crassa* FGSC 2489 lipase (SEQ ID NOs: 9 and 10, respectively).

DEFINITIONS

Figure 1:
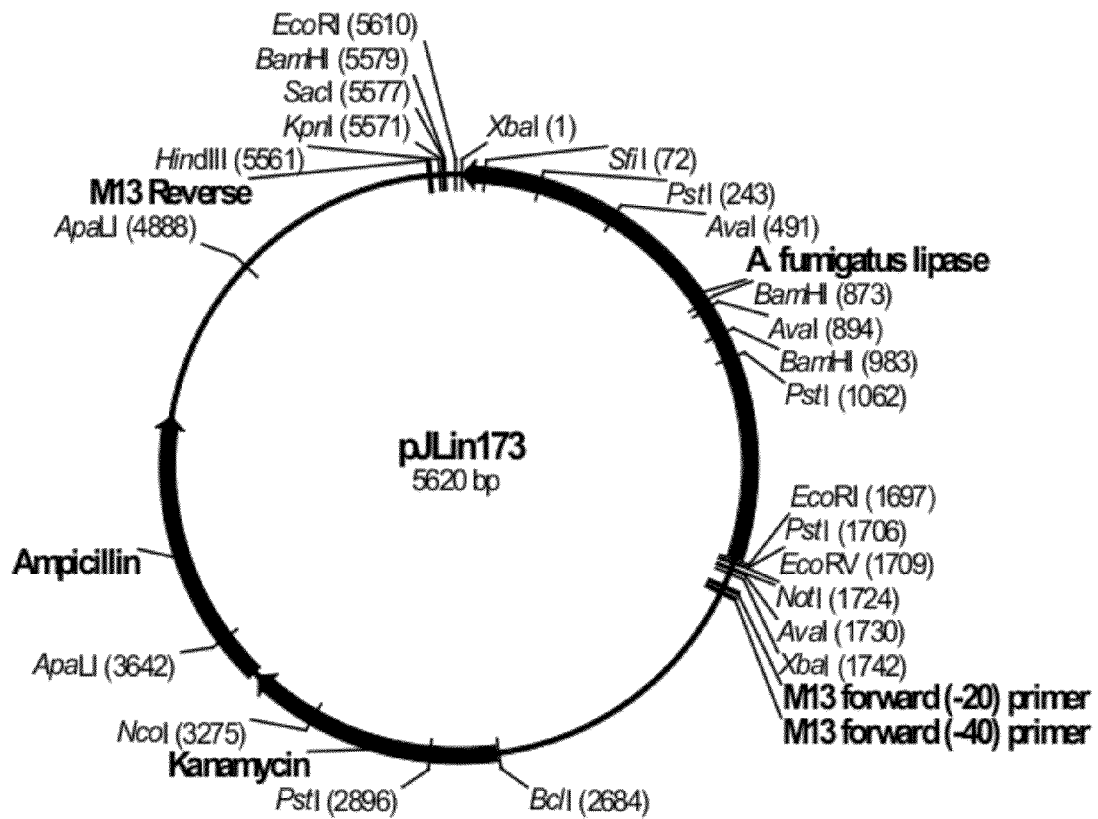
FIG. 1 shows a restriction map of pJLin173.

Lipase activity: The term "lipase activity" is defined herein as a triacylglycerol acylhydrolase activity (E.C. 3.1.1.3) which catalyzes the hydrolysis of a triacylglycerol to fatty acid(s). The substrate spectrum of lipases includes triglycerides, diglycerides, and monoglycerides, but for the purpose of the present invention, lipase activity is determined using p-nitrophenyl butyrate as substrate. One unit of lipase activity equals the amount of enzyme capable of releasing 1 μmole of butyric acid per minute at pH 7.5, 25° C. Encompassed within the term "lipase activity" are polypeptides that also have phopholipase activity, sterol ester esterase activity, and/or galactolipase activity, as defined herein.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the lipase activity of the mature polypeptide of SEQ ID NO: 2, SEQ ID NO: 4, SEQ ID NO: 6, SEQ ID NO: 8, or SEQ ID NO: 10.

Phospholipase activity: The term "phospholipase activity" is defined herein as a phosphatidyl acylhydrolase (EC 3.1.1.4, EC 3.1.1.5, and EC 3.1.1.32) which catalyzes the hydrolysis of a fatty acid from a phospholipid. Phospholipids consist of a glycerol backbone with two fatty acids in the sn1 and sn2 positions, which is esterified with a phosphoric acid in the sn3 position. The phosphoric acid may, in turn, be esterified with an amino alcohol.

Phospholipase $A_1$ (EC 3.1.1.32) catalyzes the deacylation of one fatty acyl group in the sn1 position from a diacylglycerophospholipid to produce lysophospholipid and fatty acid.

Phospholipase $A_2$ (EC 3.1.1.4) catalyzes the deacylation of one fatty acyl group in the sn2 position from a diacylglycerophospholipid to produce lysophospholipid and fatty acid.

Lysophospholipase (EC 3.1.1.5), also known as phospholipase B, catalyzes the hydrolysis of the fatty acyl group in a lysophospholipid.

For purposes of the present invention, phospholipase $A_1$, phospholipase $A_2$, and lysophospholipase activity is determined according to WO 2005/040410 using phosphatidylcholines derived from soy (Avanti Polar Lipids Inc., AL, USA) or alkylated phosphatidylethanolamines as substrates.

Galactolipase activity: The term "galactolipase activity" is defined herein as a 1,2-diacyl-3-beta-D-galactosyl-sn-glycerol acylhydrolase (EC 3.1.1.26) which catalyzes the hydrolysis of galactolipids by removing one or two fatty acids. Galactolipase activity is determined according to WO 2005/040410 using digalactosyldiglyceride (DGDG) or monogalactosyldiglyceride (MGDG) extracted from wheat flour as substrate. DGDG is a galactolipid that consists of two fatty acids and a digalactose. MGDG is a galactolipid that consists of two fatty acids and a galactose.

Sterol esterase activity: The term "sterol esterase activity" is defined herein as sterol ester acylhydrolase (3.1.1.13) which catalyzes the hydrolysis of sterol esters to sterol and fatty acid, e.g., cholesterol ester to cholesterol and fatty acid. Sterol esterase activity is determined according to WO 05/040410 using cholesterol linoleate as a substrate.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Mature polypeptide: The term "mature polypeptide" is defined herein as a polypeptide having lipase activity that is in its final form following translation and any post-translational modifications, such as N-terminal processing, C-terminal truncation, glycosylation, etc.

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Homologous sequence: The term "homologous sequence" is defined herein as a predicted protein which gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Thermomyces lanuginosus* lipase (Accession No. 059952).

Polypeptide fragment: The term "polypeptide fragment" is defined herein as a polypeptide having one or more amino acids deleted from the amino and/or carboxyl terminus of the mature polypeptide of SEQ ID NO: 2, SEQ ID NO: 4, SEQ ID NO: 6, SEQ ID NO: 8, or SEQ ID NO: 10; or a homologous sequence thereof; wherein the fragment has lipase activity. In a preferred aspect, a fragment contains at least 467 amino acid residues, more preferably at least 492 amino acid residues, and most preferably at least 517 amino acid residues of the mature polypeptide of SEQ ID NO: 2 or a homologous sequence thereof. In another preferred aspect, a fragment contains at least 485 amino acid residues, more preferably at least 510 amino acid residues, and most preferably at least 535 amino acid residues of SEQ ID NO: 4 of the mature polypeptide of SEQ ID NO: 4 or a homologous sequence thereof. In another preferred aspect, a fragment contains at least 500 amino acid residues, more preferably at least 525 amino acid residues, and most preferably at least 550 amino acid residues of the mature polypeptide of SEQ ID NO: 6 or a homologous sequence thereof. In another preferred aspect, a fragment contains at least 440 amino acid residues, more preferably at least 465 amino acid residues, and most preferably at least 490 amino acid residues of the mature polypeptide of SEQ ID NO: 8 or a homologous sequence thereof. In another preferred aspect, a fragment contains at least at least 460 amino acid residues, more preferably at least 485 amino acid residues, and most preferably at least 530 amino acid residues of SEQ ID NO: 10 or a homologous sequence thereof.

Subsequence: The term "subsequence" is defined herein as a nucleotide sequence having one or more nucleotides deleted from the 5' and/or 3' end of the mature polypeptide coding sequence of SEQ ID NO: 1, SEQ ID NO: 3, SEQ ID NO: 5, SEQ ID NO: 7, or SEQ ID NO: 9; or a homologous sequence thereof; wherein the subsequence encodes a polypeptide fragment having lipase activity. In a preferred aspect, a subsequence contains at least 1401 nucleotides, more preferably at least 1476 nucleotides, and most preferably at least 1551 nucleotides of the mature polypeptide coding sequence of SEQ ID NO: 1 or a homologous sequence thereof. In another preferred aspect, a subsequence contains at least 1455 nucleotides, more preferably at least 1530 nucleotides, and most preferably at least 1605 nucleotides of the mature polypeptide coding sequence of SEQ ID NO: 3 or a homologous sequence thereof. In a preferred aspect, a subsequence contains at least 1500 nucleotides, more preferably at least 1575 nucleotides, and most preferably at least 1650 nucleotides of the mature polypeptide coding sequence of SEQ ID NO: 5 or a homologous sequence thereof. In another preferred aspect, a subsequence contains at least 1320 nucleotides, more preferably at least 1395 nucleotides, and most preferably at least 1470 nucleotides of the mature polypeptide coding sequence of SEQ ID NO: 7 or a homologous sequence thereof. In another preferred aspect, a subsequence contains at least 1380 nucleotides, more preferably at least 1455 nucleotides, and most preferably at least 1590 nucleotides of the mature polypeptide coding sequence of SEQ ID NO: 9 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Mature polypeptide coding sequence: The term "mature polypeptide coding sequence" is defined herein as a nucleotide sequence that encodes a mature polypeptide having lipase activity.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2, SEQ ID NO: 4, SEQ ID NO: 6, SEQ ID NO: 8, or SEQ ID NO: 10; or a homologous sequence thereof; as well as genetic manipulation of the DNA encoding such a polypeptide. The modification can be substitutions, deletions and/or insertions of one or more amino acids as well as replacements of one or more amino acid side chains.

Artificial variant: When used herein, the term "artificial variant" means a polypeptide having lipase activity produced by an organism expressing a modified nucleotide sequence of the mature polypeptide coding sequence of SEQ ID NO: 1, SEQ ID NO: 3, SEQ ID NO: 5, SEQ ID NO: 7, or SEQ ID NO: 9; or a homologous sequence thereof. The modified nucleotide sequence is obtained through human intervention by modification of the nucleotide sequence disclosed in SEQ ID NO: 1, SEQ ID NO: 3, SEQ ID NO: 5, SEQ ID NO: 7, or SEQ ID NO: 9; or a homologous sequence thereof.

DETAILED DESCRIPTION OF THE INVENTION

Polypeptides Having Lipase Activity

In a first aspect, the present invention relates to isolated polypeptides having an amino acid sequence which has a degree of identity to the mature polypeptide of SEQ ID NO: 2, SEQ ID NO: 4, SEQ ID NO: 6, SEQ ID NO: 8, or SEQ ID NO: 10, of at least 60%, preferably at least 65%, more preferably at least 70%, more preferably at least 75%, more preferably at least 80%, more preferably at least 85%, even more preferably at least 90%, most preferably at least 95%, and even most preferably at least 97%, 98%, or 99%, which have lipase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from the mature polypeptide of SEQ ID NO: 2, SEQ ID NO: 4, SEQ ID NO: 6, SEQ ID NO: 8, or SEQ ID NO: 10.

A polypeptide of the present invention preferably comprises the amino acid sequence of SEQ ID NO: 2 or an allelic variant thereof; or a fragment thereof that has lipase activity. In a preferred aspect, a polypeptide comprises the amino acid sequence of SEQ ID NO: 2. In another preferred aspect, a polypeptide comprises the mature polypeptide of SEQ ID NO: 2. In another preferred aspect, a polypeptide comprises amino acids 21 to 562 of SEQ ID NO: 2, or an allelic variant thereof; or a fragment thereof that has lipase activity. In another preferred aspect, a polypeptide comprises amino acids 21 to 562 of SEQ ID NO: 2. In another preferred aspect, a polypeptide consists of the amino acid sequence of SEQ ID NO: 2 or an allelic variant thereof; or a fragment thereof that has lipase activity. In another preferred aspect, a polypeptide consists of the amino acid sequence of SEQ ID NO: 2. In another preferred aspect, a polypeptide consists of the mature polypeptide of SEQ ID NO: 2. In another preferred aspect, a polypeptide consists of amino acids 21 to 562 of SEQ ID NO: 2 or an allelic variant thereof; or a fragment thereof that has lipase activity. In another preferred aspect, a polypeptide consists of amino acids 21 to 562 of SEQ ID NO: 2.

A polypeptide of the present invention preferably comprises the amino acid sequence of SEQ ID NO: 4, or an allelic variant thereof; or a fragment thereof that has lipase activity. In a preferred aspect, a polypeptide comprises the amino acid sequence of SEQ ID NO: 4. In another preferred aspect, a polypeptide comprises the mature polypeptide of SEQ ID NO: 4. In another preferred aspect, a polypeptide comprises amino acids 25 to 588 of SEQ ID NO: 4, or an allelic variant thereof; or a fragment thereof that has lipase activity. In another preferred aspect, a polypeptide comprises amino acids 25 to 588 of SEQ ID NO: 4. In another preferred aspect, a polypeptide consists of the amino acid sequence of SEQ ID NO: 4 or an allelic variant thereof; or a fragment thereof that has lipase activity. In another preferred aspect, a polypeptide consists of the amino acid sequence of SEQ ID NO: 4. In another preferred aspect, a polypeptide consists of amino acids 25 to 588 of SEQ ID NO: 4 or an allelic variant thereof; or a fragment thereof that has lipase activity. In another preferred aspect, a polypeptide consists of amino acids 25 to 588 of SEQ ID NO: 4.

A polypeptide of the present invention preferably comprises the amino acid sequence of SEQ ID NO: 6, or an allelic variant thereof; or a fragment thereof that has lipase activity. In a preferred aspect, a polypeptide comprises the amino acid sequence of SEQ ID NO: 6. In another preferred aspect, a polypeptide comprises the mature polypeptide of SEQ ID NO: 6. In another preferred aspect, a polypeptide comprises amino acids 21 to 598 of SEQ ID NO: 6, or an allelic variant thereof; or a fragment thereof that has lipase activity. In another preferred aspect, a polypeptide comprises amino acids 21 to 598 of SEQ ID NO: 6. In another preferred aspect, a polypeptide consists of the amino acid sequence of SEQ ID NO: 6 or an allelic variant thereof; or a fragment thereof that has lipase activity. In another preferred aspect, a polypeptide consists of the amino acid sequence of SEQ ID NO: 6. In another preferred aspect, a polypeptide consists of amino acids 21 to 598 of SEQ ID NO: 6 or an allelic variant thereof; or a fragment thereof that has lipase activity. In another preferred aspect, a polypeptide consists of amino acids 21 to 598 of SEQ ID NO: 6.

A polypeptide of the present invention preferably comprises the amino acid sequence of SEQ ID NO: 8, or an allelic variant thereof; or a fragment thereof that has lipase activity. In a preferred aspect, a polypeptide comprises the amino acid sequence of SEQ ID NO: 8. In another preferred aspect, a polypeptide comprises the mature polypeptide of SEQ ID NO: 8. In another preferred aspect, a polypeptide comprises amino acids 19 to 534 of SEQ ID NO: 8, or an allelic variant thereof; or a fragment thereof that has lipase activity. In another preferred aspect, a polypeptide comprises amino acids 19 to 534 of SEQ ID NO: 8. In another preferred aspect, a polypeptide consists of the amino acid sequence of SEQ ID NO: 8 or an allelic variant thereof; or a fragment thereof that has lipase activity. In another preferred aspect, a polypeptide consists of the amino acid sequence of SEQ ID NO: 8. In another preferred aspect, a polypeptide consists of amino acids 19 to 534 of SEQ ID NO: 8 or an allelic variant thereof; or a fragment thereof that has lipase activity. In another preferred aspect, a polypeptide consists of amino acids 19 to 534 of SEQ ID NO: 8.

A polypeptide of the present invention preferably comprises the amino acid sequence of SEQ ID NO: 10, or an allelic variant thereof; or a fragment thereof that has lipase activity. In a preferred aspect, a polypeptide comprises the amino acid sequence of SEQ ID NO: 10. In another preferred aspect, a polypeptide comprises the mature polypeptide of SEQ ID NO: 10. In another preferred aspect, a polypeptide comprises amino acids 22 to 578 of SEQ ID NO: 10, or an allelic variant thereof; or a fragment thereof that has lipase activity. In another preferred aspect, a polypeptide comprises amino acids 22 to 578 of SEQ ID NO: 10. In another preferred aspect, a polypeptide consists of the amino acid sequence of SEQ ID NO: 10 or an allelic variant thereof; or a fragment thereof that has lipase activity. In another preferred aspect, a polypeptide consists of the amino acid sequence of SEQ ID NO: 10. In another preferred aspect, a polypeptide consists of amino acids 22 to 578 of SEQ ID NO: 10 or an allelic variant thereof; or a fragment thereof that has lipase activity. In another preferred aspect, a polypeptide consists of amino acids 22 to 578 of SEQ ID NO: 10.

In a second aspect, the present invention relates to isolated polypeptides having lipase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, SEQ ID NO: 5, SEQ ID NO: 7, or SEQ ID NO: 9, (ii) the cDNA sequence contained in the mature polypeptide coding sequence of SEQ ID NO: 1, SEQ ID NO: 3, SEQ ID NO: 5, SEQ ID NO: 7, or SEQ ID NO: 9, (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual,* 2d edition, Cold Spring Harbor, N.Y.). A subsequence of the mature polypeptide coding sequence of SEQ ID NO: 1, SEQ ID NO: 3, SEQ ID NO: 5, SEQ ID NO: 7, or SEQ ID NO: 9 contains at least 100 contiguous nucleotides or preferably at least 200 contiguous nucleotides. Moreover, the subsequence may encode a polypeptide fragment which has lipase activity. In a preferred aspect, the mature polypeptide coding sequence is nucleotides 61 to 1686 of SEQ ID NO: 1, nucleotides 73 to 1764 of SEQ ID NO: 3, nucleotides 61 to 1922 of SEQ ID NO: 5, nucleotides 55 to 1602 of SEQ ID NO: 7, or nucleotides 64 to 1789 of SEQ ID NO: 9.

The nucleotide sequence of SEQ ID NO: 1, SEQ ID NO: 3, SEQ ID NO: 5, SEQ ID NO: 7, or SEQ ID NO: 9; or a subsequence thereof; as well as the amino acid sequence of SEQ ID NO: 2, SEQ ID NO: 4, SEQ ID NO: 6, SEQ ID NO: 8, or SEQ ID NO: 10; or a fragment thereof; may be used to design a nucleic acid probe to identify and clone DNA encoding polypeptides having lipase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other organisms may, therefore, be screened for DNA which hybridizes with the probes described above and which encodes a polypeptide having lipase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, SEQ ID NO: 3, SEQ ID NO: 5, SEQ ID NO: 7, or SEQ ID NO: 9; or a subsequence thereof; the carrier material is used in a Southern blot.

For purposes of the present invention, hybridization indicates that the nucleotide sequence hybridizes to a labeled nucleic acid probe corresponding to the mature polypeptide coding sequence of SEQ ID NO: 1, SEQ ID NO: 3, SEQ ID NO: 5, SEQ ID NO: 7, or SEQ ID NO: 9, the cDNA sequence contained in the mature polypeptide coding sequence of SEQ ID NO: 1, SEQ ID NO: 3, SEQ ID NO: 5, SEQ ID NO: 7, or SEQ ID NO: 9; its complementary strand; or a subsequence thereof; under very low to very high stringency conditions. Molecules to which the nucleic acid probe hybridizes under these conditions can be detected using X-ray film.

In a preferred aspect, the nucleic acid probe is the mature polypeptide coding sequence of SEQ ID NO: 1. In another preferred aspect, the nucleic acid probe is nucleotides 61 to 1686 of SEQ ID NO: 1. In another preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pJLin173 which is contained in *E. coli* NRRL B-30782, wherein the polynucleotide sequence thereof encodes a polypeptide having lipase activity. In another preferred aspect, the nucleic acid probe is the mature polypeptide coding region contained in plasmid pJLin173 which is contained in *E. coli* NRRL B-30782.

In another preferred aspect, the nucleic acid probe is the mature polypeptide coding sequence of SEQ ID NO: 3. In another preferred aspect, the nucleic acid probe is nucleotides 73 to 1764 of SEQ ID NO: 3. In another preferred aspect, the nucleic acid probe is a polynucleotide sequence which encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pSMO230 which is contained in *E. coli* NRRL B-30803, wherein the polynucleotide sequence thereof encodes a polypeptide having lipase activity. In another preferred aspect, the nucleic acid probe is the mature polypeptide coding region contained in plasmid pSMO230 which is contained in *E. coli* NRRL B-30803.

In another preferred aspect, the nucleic acid probe is the mature polypeptide coding sequence of SEQ ID NO: 5. In another preferred aspect, the nucleic acid probe is nucleotides 61 to 1922 of SEQ ID NO: 5. In another preferred aspect, the nucleic acid probe is a polynucleotide sequence which encodes the polypeptide of SEQ ID NO: 6, or a subsequence thereof. In another preferred aspect, the nucleic acid probe is SEQ ID NO: 5. In another preferred aspect, the nucleic acid probe is the polynucleotide sequence contained in plasmid pJLin175 which is contained in *E. coli* NRRL B-30783, wherein the polynucleotide sequence thereof encodes a polypeptide having lipase activity. In another preferred aspect, the nucleic acid probe is the mature polypeptide coding region contained in plasmid pJLin175 which is contained in *E. coli* NRRL B-30783.

In another preferred aspect, the nucleic acid probe is the mature polypeptide coding sequence of SEQ ID NO: 7. In another preferred aspect, the nucleic acid probe is nucleotides 55 to 1602 of SEQ ID NO: 7. In another preferred aspect, the nucleic acid probe is a polynucleotide sequence which encodes the polypeptide of SEQ ID NO: 8, or a subsequence thereof. In another preferred aspect, the nucleic acid probe is SEQ ID NO: 7. In another preferred aspect, the nucleic acid probe is the polynucleotide sequence contained in plasmid pCrAm140 which is contained in *E. coli* NRRL B-30788, wherein the polynucleotide sequence thereof encodes a polypeptide having lipase activity. In another preferred aspect, the nucleic acid probe is the mature polypeptide coding region contained in plasmid pCrAm140 which is contained in *E. coli* NRRL B-30788.

In another preferred aspect, the nucleic acid probe is the mature polypeptide coding sequence of SEQ ID NO: 9. In another preferred aspect, the nucleic acid probe is nucleotides 64 to 1789 of SEQ ID NO: 9. In another preferred aspect, the nucleic acid probe is a polynucleotide sequence which encodes the polypeptide of SEQ ID NO: 10, or a subsequence thereof. In another preferred aspect, the nucleic acid probe is SEQ ID NO: 9. In another preferred aspect, the nucleic acid probe is the polynucleotide sequence contained in plasmid pBM134b which is contained in E. coli NRRL B-30786, wherein the polynucleotide sequence thereof encodes a polypeptide having lipase activity. In another preferred aspect, the nucleic acid probe is the mature polypeptide coding region contained in plasmid pBM134b which is contained in E. coli NRRL B-30786.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to artificial variants comprising a conservative substitution, deletion, and/or insertion of one or more amino acids of the mature polypeptide of SEQ ID NO: 2, SEQ ID NO: 4, SEQ ID NO: 6, SEQ ID NO: 8, or SEQ ID NO: 10; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., lipase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 21 to 562 of SEQ ID NO: 2, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 4, such as amino acids 25 to 588 of SEQ ID NO: 4, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 6, such as amino acids 21 to 598 of SEQ ID NO: 6, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 8, such as amino acids 19 to 534 of SEQ ID NO: 8, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 10, such as amino acids 22 to 578 of SEQ ID NO: 8, is 10, preferably 9, more preferably 8, more preferably 7, more preferably at most 6, more preferably 5, more preferably 4, even more preferably 3, most preferably 2, and even most preferably 1.

Sources of Polypeptides Having Lipase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide having lipase activity, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide having lipase activity; or a *Streptomyces* polypeptide having lipase activity, e.g., a *Streptomyces lividans* or *Streptomyces murinus* polypeptide having lipase activity; or a gram negative bacterial polypeptide having lipase activity, e.g., an *E. coli* or a *Pseudomonas* sp. polypeptide having lipase activity.

A polypeptide of the present invention may also be a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide having lipase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having lipase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide having lipase activity.

In another preferred aspect, the polypeptide is a *Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Thielavia terricola, Thielavia thermophila, Thielavia variospora,* or *Thielavia wareingii* polypeptide having lipase activity.

In a more preferred aspect, the polypeptide is an *Aspergillus fumigatus* polypeptide, e.g., the polypeptide of SEQ ID NO: 2, or the mature polypeptide thereof.

In another more preferred aspect, the polypeptide is a *Fusarium graminearum* polypeptide, and most preferably *Fusarium graminearum* NRRL 31084, e.g., the polypeptide of SEQ ID NO: 4, or the mature polypeptide thereof.

In another more preferred aspect, the polypeptide is a *Magnaporthe grisea* polypeptide, and most preferably *Magnaporthe grisea* FGSC 8958 (Fungal Genetics Stock Center, Kansas City, Mo.) polypeptide, e.g., the polypeptide of SEQ ID NO: 6 or SEQ ID NO: 8; or the mature polypeptide thereof.

In another more preferred aspect, the polypeptide is an *Aspergillus nidulans* polypeptide, and most preferably *Aspergillus nidulans* FGSC 2489 (Fungal Genetics Stock Center, Kansas City, Mo.) polypeptide, e.g., the polypeptide of SEQ ID NO: 10; or the mature polypeptide thereof.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention.

In a preferred aspect, the nucleotide sequence is set forth in SEQ ID NO: 1. In another more preferred aspect, the nucleotide sequence is the sequence contained in plasmid pJLin173 which is contained in *E. coli* NRRL B-30782. In another preferred aspect, the nucleotide sequence is the mature polypeptide coding region of SEQ ID NO: 1. In another preferred aspect, the nucleotide sequence is nucleotides 61 to 1686 of SEQ ID NO: 1. In another more preferred aspect, the nucleotide sequence is the mature polypeptide coding region contained in plasmid pJLin173 which is contained in *E. coli* NRRL B-30782. The present invention also encompasses nucleotide sequences which encode a polypeptide having the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 which encode fragments of SEQ ID NO: 2 that have lipase activity.

In another preferred aspect, the nucleotide sequence is set forth in SEQ ID NO: 3. In another more preferred aspect, the nucleotide sequence is the sequence contained in plasmid pSMO230 which is contained in *E. coli* NRRL B-30803. In another preferred aspect, the nucleotide sequence is the mature polypeptide coding region of SEQ ID NO: 3. In another preferred aspect, the nucleotide sequence is nucleotides 73 to 1764 of SEQ ID NO: 3. In another more preferred aspect, the nucleotide sequence is the mature polypeptide coding region contained in plasmid pSMO230 which is contained in *E. coli* NRRL B-30803. The present invention also encompasses nucleotide sequences which encode a polypeptide having the amino acid sequence of SEQ ID NO: 4 or the mature polypeptide thereof, which differ from SEQ ID NO: 3 or the mature polypeptide coding sequence thereof by virtue of the degeneracy of the genetic code. The present invention also relates to subsequences of SEQ ID NO: 3 which encode fragments of SEQ ID NO: 4 that have lipase activity.

In another preferred aspect, the nucleotide sequence is set forth in SEQ ID NO: 5. In another more preferred aspect, the nucleotide sequence is the sequence contained in plasmid pJLin175 which is contained in *E. coli* NRRL B-30783. In another preferred aspect, the nucleotide sequence is the mature polypeptide coding region of SEQ ID NO: 5. In another preferred aspect, the nucleotide sequence is nucleotides 61 to 1922 of SEQ ID NO: 5. In another more preferred aspect, the nucleotide sequence is the mature polypeptide coding region contained in plasmid pJLin175 which is contained in *E. coli* NRRL B-30783. The present invention also encompasses nucleotide sequences which encode a polypeptide having the amino acid sequence of SEQ ID NO: 6 or the mature polypeptide thereof, which differ from SEQ ID NO: 5 or the mature polypeptide coding sequence thereof by virtue of the degeneracy of the genetic code. The present invention also relates to subsequences of SEQ ID NO: 5 which encode fragments of SEQ ID NO: 6 that have lipase activity.

In another preferred aspect, the nucleotide sequence is set forth in SEQ ID NO: 7. In another more preferred aspect, the nucleotide sequence is the sequence contained in plasmid pCrAm140 which is contained in *E. coli* NRRL B-30788. In another preferred aspect, the nucleotide sequence is the mature polypeptide coding region of SEQ ID NO: 7. In another preferred aspect, the nucleotide sequence is nucleotides 55 to 1602 of SEQ ID NO: 7. In another more preferred aspect, the nucleotide sequence is the mature polypeptide coding region contained in plasmid pCrAm140 which is contained in *E. coli* NRRL B-30788. The present invention also encompasses nucleotide sequences which encode a polypeptide having the amino acid sequence of SEQ ID NO: 8 or the mature polypeptide thereof, which differ from SEQ ID NO: 7 or the mature polypeptide coding sequence thereof by virtue of the degeneracy of the genetic code. The present invention also relates to subsequences of SEQ ID NO: 7 which encode fragments of SEQ ID NO: 8 that have lipase activity.

In another preferred aspect, the nucleotide sequence is set forth in SEQ ID NO: 9. In another more preferred aspect, the nucleotide sequence is the sequence contained in plasmid pBM134b which is contained in *E. coli* NRRL B-30786. In another preferred aspect, the nucleotide sequence is the mature polypeptide coding region of SEQ ID NO: 9. In another preferred aspect, the nucleotide sequence is nucleotides 64 to 1789 of SEQ ID NO: 9. In another more preferred aspect, the nucleotide sequence is the mature polypeptide coding region contained in plasmid pBM134b which is contained in *E. coli* NRRL B-30786. The present invention also encompasses nucleotide sequences which encode a polypeptide having the amino acid sequence of SEQ ID NO: 10 or the mature polypeptide thereof, which differ from SEQ ID NO: 9 or the mature polypeptide coding sequence thereof by virtue of the degeneracy of the genetic code. The present invention also relates to subsequences of SEQ ID NO: 9 which encode fragments of SEQ ID NO: 10 that have lipase activity.

The present invention also relates to mutant polunucleotides comprising at least one mutation in the mature polypeptide coding sequence of SEQ ID NO: 1, in which the mutant nucleotide sequence encodes the mature polypeptide of SEQ ID NO: 2. In a preferred aspect, the mature polypeptide is amino acids 21 to 562 of SEQ ID NO: 2.

The present invention also relates to mutant polunucleotides comprising at least one mutation in the mature polypeptide coding sequence of SEQ ID NO: 3, in which the mutant nucleotide sequence encodes the mature polypeptide of SEQ ID NO: 4. In a preferred aspect, the mature polypeptide is amino acids 25 to 588 of SEQ ID NO: 4.

The present invention also relates to mutant polynucleotides comprising at least one mutation in the mature polypeptide coding sequence of SEQ ID NO: 5, in which the mutant nucleotide sequence encodes the mature polypeptide of SEQ ID NO: 6. In a preferred aspect, the mature polypeptide is amino acids 21 to 598 of SEQ ID NO: 6.

The present invention also relates to mutant polynucleotides comprising at least one mutation in the mature polypeptide coding sequence of SEQ ID NO: 7, in which the mutant nucleotide sequence encodes the mature polypeptide of SEQ ID NO: 8. In a preferred aspect, the mature polypeptide is amino acids 19 to 534 of SEQ ID NO: 8.

The present invention also relates to mutant polynucleotides comprising at least one mutation in the mature polypeptide coding sequence of SEQ ID NO: 9, in which the mutant nucleotide sequence encodes the mature polypeptide of SEQ ID NO: 10. In a preferred aspect, the mature polypeptide is amino acids 22 to 578 of SEQ ID NO: 10.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thielavia*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1 of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 61 to 1686 of SEQ ID NO: 1.

The present invention also relates to polynucleotides having nucleotide sequences which have a degree of identity to the mature polypeptide coding sequence of SEQ ID NO: 3 of at least 70%, preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 73 to 1764 of SEQ ID NO: 3.

The present invention also relates to polynucleotides having nucleotide sequences which have a degree of identity to the mature polypeptide coding sequence of SEQ ID NO: 5 of at least 70%, preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 61 to 1922 of SEQ ID NO: 5.

The present invention also relates to polynucleotides having nucleotide sequences which have a degree of identity to the mature polypeptide coding sequence of SEQ ID NO: 7 of at least 70%, preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 55 to 1602 of SEQ ID NO: 7.

The present invention also relates to polynucleotides having nucleotide sequences which have a degree of identity to the mature polypeptide coding sequence of SEQ ID NO: 9 of at least 70%, preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 64 to 1789 of SEQ ID NO: 9.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, SEQ ID NO: 3, SEQ ID NO: 5, SEQ ID NO: 7, or SEQ ID NO: 9, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for lipase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, SEQ ID NO: 5, SEQ ID NO: 7, or SEQ ID NO: 9, (ii) the cDNA sequence contained in the mature polypeptide coding sequence of SEQ ID NO: 1, SEQ ID NO: 3, SEQ ID NO: 5, SEQ ID NO: 7, or SEQ ID NO: 9, or (iii) a complementary strand of (i) or (ii); or allelic variants and subsequences thereof (Sambrook et al., 1989, supra), as defined herein. In a preferred aspect, the mature polypeptide coding sequence of SEQ ID NO: 1 is nucleotides 61 to 1686. In another preferred aspect, the mature polypeptide coding sequence of SEQ ID NO: 3 is nucleotides 73 to 1764. In another preferred aspect, the mature polypeptide coding sequence of SEQ ID NO: 5 is nucleotides 61 to 1922. In another preferred aspect, the mature polypeptide coding sequence of SEQ ID NO: 7 is nucleotides 55 to 1602. In another preferred aspect, the mature polypeptide coding sequence of SEQ ID NO: 9 is nucleotides 64 to 1789.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, SEQ ID NO: 3, SEQ ID NO: 5, SEQ ID NO: 7, or SEQ ID NO: 9, (ii) the cDNA sequence contained in the mature polypeptide coding sequence of SEQ ID NO: 1, SEQ ID NO: 3, SEQ ID NO: 5, SEQ ID NO: 7, or SEQ ID NO: 9, or (iii) a complementary strand of (i) or (ii); and (b) isolating the hybridizing polynucleotide, which encodes a polypeptide having lipase activity. In a preferred aspect, the mature polypeptide coding sequence of SEQ ID NO: 1 is nucleotides 61 to 1686. In another preferred aspect, the mature polypeptide coding sequence of SEQ ID NO: 3 is nucleotides 73 to 1764. In another preferred aspect, the mature polypeptide coding sequence of SEQ ID NO: 5 is nucleotides 61 to 1922. In another preferred aspect, the mature polypeptide coding sequence of SEQ ID NO: 7 is nucleotides 55 to 1602. In another preferred aspect, the mature polypeptide coding sequence of SEQ ID NO: 9 is nucleotides 64 to 1789.

Nucleic Acid Constructs

The present invention also relates to nucleic acid constructs comprising an isolated polynucleotide of the present invention operably linked to one or more control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

In a preferred aspect, the signal peptide coding region is nucleotides 1 to 60 of SEQ ID NO: 1 which encode amino acids 1 to 20 of SEQ ID NO: 2.

In another preferred aspect, the signal peptide coding region is nucleotides 1 to 72 of SEQ ID NO: 3 which encode amino acids 1 to 24 of SEQ ID NO: 4.

In another preferred aspect, the signal peptide coding region is nucleotides 1 to 60 of SEQ ID NO: 5 which encode amino acids 1 to 20 of SEQ ID NO: 6.

In another preferred aspect, the signal peptide coding region is nucleotides 1 to 54 of SEQ ID NO: 7 which encode amino acids 1 to 18 of SEQ ID NO: 8.

In another preferred aspect, the signal peptide coding region is nucleotides 1 to 63 of SEQ ID NO: 9 which encode amino acids 1 to 21 of SEQ ID NO: 10.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizen, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a Candida, Hansenula, Kluyveromyces, Pichia, Saccharomyces, Schizosaccharomyces, or Yarrowia cell.

In a most preferred aspect, the yeast host cell is a Saccharomyces carlsbergensis, Saccharomyces cerevisiae, Saccharomyces diastaticus, Saccharomyces douglasii, Saccharomyces kluyveri, Saccharomyces norbensis, or Saccharomyces oviformis cell. In another most preferred aspect, the yeast host cell is a Kluyveromyces lactis cell. In another most preferred aspect, the yeast host cell is a Yarrowia lipolytica cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

In an even more preferred aspect, the filamentous fungal host cell is an Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

In a most preferred aspect, the filamentous fungal host cell is an Aspergillus awamori, Aspergillus fumigatus, Aspergillus foetidus, Aspergillus japonicus, Aspergillus nidulans, Aspergillus niger or Aspergillus oryzae cell. In another most preferred aspect, the filamentous fungal host cell is a Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, or Fusarium venenatum cell. In another most preferred aspect, the filamentous fungal host cell is a Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238 023 and Yelton et al., 1984, Proceedings of the National Academy of Sciences USA 81: 1470-1474. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention, comprising: (a) cultivating a cell, which in its wild-type form is capable of producing the polypeptide, under conditions conducive for production of the polypeptide; and (b) recovering the polypeptide. In a preferred aspect, the cell is of the genus Aspergillus. In a more preferred aspect, the cell is Aspergillus fumigatus. In another more preferred aspect, the cell is Aspergillus nidulans. In another preferred aspect, the cell is of the genus Magnaporthe. In another more preferred aspect, the cell is Magnaporthe grisea.

The present invention also relates to methods for producing a polypeptide of the present invention, comprising: (a) cultivating a host cell under conditions conducive for production of the polypeptide; and (b) recovering the polypeptide.

The present invention also relates to methods for producing a polypeptide of the present invention, comprising: (a) cultivating a host cell under conditions conducive for production of the polypeptide, wherein the host cell comprises a mutant nucleotide sequence having at least one mutation in the mature polypeptide coding sequence of SEQ ID NO: 1, SEQ ID NO: 3, SEQ ID NO: 5, SEQ ID NO: 7, or SEQ ID NO: 9, wherein the mutant nucleotide sequence encodes a polypeptide which comprises or consists of the mature polypeptide of SEQ ID NO: 2, SEQ ID NO: 4, SEQ ID NO: 6, SEQ ID NO: 8, or SEQ ID NO: 10, and (b) recovering the polypeptide.

In a preferred aspect, the mature polypeptide of SEQ ID NO: 2 is amino acids 21 to 562. In another preferred aspect, the mature polypeptide of SEQ ID NO: 4 is amino acids 25 to 588. In another preferred aspect, the mature polypeptide of SEQ ID NO: 6 is amino acids 21 to 598. In another preferred aspect, the mature polypeptide of SEQ ID NO: 8 is amino acids 19 to 534. In another preferred aspect, the mature polypeptide of SEQ ID NO: 10 is amino acids 22 to 578.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to a transgenic plant, plant part, or plant cell which has been transformed with a nucleotide sequence encoding a polypeptide having lipase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, Cell 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising: (a) cultivating a transgenic plant or a plant cell comprising a polynucleotide encoding a polypeptide having lipase activity of the present invention under conditions conducive for production of the polypeptide; and (b) recovering the polypeptide.

Removal or Reduction of Lipase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising: (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of lipase activity by fermentation of a cell which produces both a polypeptide of the present invention as well as the protein product of interest by adding an effective amount of an agent capable of inhibiting lipase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of lipase activity by cultivating the cell under conditions permitting the expression of the product, subjecting the resultant culture broth to a combined pH and temperature treatment so as to reduce the lipase activity substantially, and recovering the product from the culture broth. Alternatively, the combined pH and temperature treatment may be performed on an enzyme preparation recovered from the culture broth. The combined pH and temperature treatment may optionally be used in combination with a treatment with an lipase inhibitor.

In accordance with this aspect of the invention, it is possible to remove at least 60%, preferably at least 75%, more preferably at least 85%, still more preferably at least 95%, and most preferably at least 99% of the lipase activity. Complete removal of lipase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially lipase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The lipase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from lipase activity which is produced by a method of the present invention.

Compositions

The present invention also relates to compositions comprising a polypeptide of the present invention. Preferably, the compositions are enriched in such a polypeptide. The term "enriched" indicates that the lipase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having lipase activity, or compositions thereof.

Use in Degumming.

A polypeptide of the present invention may be used for degumming an aqueous carbohydrate solution or slurry to improve its filterability, particularly, a starch hydrolysate, especially a wheat starch hydrolysate which is difficult to filter and yields cloudy filtrates. The treatment may be performed using methods well known in the art. See, for example, EP 219,269, EP 808,903, and U.S. Pat. No. 6,103,505.

Use in Baking.

A polypeptide of the present invention may be used in baking according to U.S. Pat. No. 6,558,715.

Use in Detergents.

The polypeptides of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein. The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254 WO 95/24471, WO 98/12307 and PCT/DK98/00299.

Commercially available cellulases include Celluzyme™, and Carezyme™ (Novozymes NS), Clazinase™, and Puradax HA™ (Genencor International Inc.), and KAC-500 (B)™ (Kao Corporation).

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™ Primase™, Duralase™, Esperase™, and Kannase™ (Novozymes A/S), Maxatase™ Maxacal™, Maxapem™, Properase™, Purafect™, Purafect OxP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas lipase*, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™, and Lipex™ (Novozymes A/S).

Amylases:

Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide of the present invention may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the present invention may also be incorporated in the detergent formulations disclosed in WO 97/07202, which is hereby incorporated by reference.

Signal Peptide

The present invention also relates to nucleic acid constructs comprising a gene encoding a protein operably linked to a nucleotide sequence comprising or consisting of nucleotides 1 to 60 of SEQ ID NO: 1, nucleotides 1 to 72 of SEQ ID NO: 3, nucleotides 1 to 60 of SEQ ID NO: 5, nucleotides 1 to 54 of SEQ ID NO: 7, or nucleotides 1 to 63 of SEQ ID NO: 9, encoding a signal peptide comprising or consisting of amino acids 1 to 20 of SEQ ID NO: 2, amino acids 1 to 24 of SEQ ID NO: 4, amino acids 1 to 20 of SEQ ID NO: 6, amino acids 1 to 18 of SEQ ID NO: 8, or amino acids 1 to 21 of SEQ ID NO: 10, respectively, wherein the gene is foreign to the nucleotide sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.

Strains

*Aspergillus fumigatus* PaHa34, *Fusarium graminearum* NRRL 31084, *Magnaporthe grisea* FGSC 8958 (Fungal Genetics Stock Center), and *Aspergillus nidulans* FGSC 2489 (Fungal Genetics Stock Center) were used as the sources of the lipase genes.

Media

SOC medium was composed per liter of 20 g of tryptone, 5 g of yeast extract, 2 ml of 5 M NaCl, and 2.5 ml of 1 M KCl.

$NZY^+$ medium was composed per liter of 10 g of NZ amine, 5 g of yeast extract, 5 g of NaCl, 12.5 mM $MgCl_2$, 12.5 mM $MgSO_4$, and 10 ml of 2 M glucose.

LB medium was composed per liter of 10 g of tryptone, 5 g of yeast extract, and 5 g of NaCl.

MY25 medium was composed per liter of 25 g of maltodextrin, 2 g of $MgSO_4.7H_2O$, 10 g of $KH_2PO_4$, 2 g of citric acid, 2 g of $K_2SO_4$, 2 g of urea, 10 g of yeast extract, and 1.5 ml of AMG trace metals solution, adjusted to pH 6.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

COVE selection plates were composed per liter of 342.3 g of sucrose, 20 ml of COVE salt solution, 10 mM acetamide, 15 mM $CsCl_2$, and 25 g of Noble agar.

COVE salt solution was composed per liter of 26 g of KCl, 26 g of $MgSO_4.7H_2O$, 76 g of $KH_2PO_4$, and 50 ml of COVE trace metals solution.

COVE trace metals solution was composed per liter of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

2xYT plates were composed per liter of 16 g of tryptone, 10 g of yeast extract, 5 g of NaCl, and 15 g of Bacto agar.

M400 medium was composed per liter of 50 g of maltodextrin, 2 g of $MgSO_4.7H_2O$, 2 g of $KH_2PO_4$, 4 g of citric acid, 8 g of yeast extract, 2 g of urea, 0.5 g of $CaCl_2$, and 0.5 ml of AMG trace metals solution.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

$NZY^+$ medium was composed per liter of 10 g of NZ amine, 5 g of yeast extract, 5 g of NaCl, 12.5 mM $MgCl_2$, 12.5 mM $MgSO_4$, and 10 ml of 2 M glucose.

RA sporulation medium was composed per liter of 1 g of glucose, 50 g of succinic acid, 12.1 g of $NaNO_3$, and 20 ml of 50x Vogel's salts (no C, no N).

50x Vogel's salts (no C, no N) was composed per liter of 250 g of $KH_2PO_4$, 10 g of $MgSO_4.7H_2O$, 5 g of $CaCl_2.2H_2O$, 2.5 ml of biotin solution, and 5 ml of Vogel's trace elements.

50xVogel's trace elements solution was composed per liter of 50 g of citric acid, 50 g of $ZnSO_4.7H_2O$, 10 g of $Fe(NH_4)_2(SO_4)_2.6H_2O$, 2.5 g of $CuSO_4.5H_2O$, 0.5 g of $MnSO_4.H_2O$, 0.5 g of $H_3BO_3$, and 0.5 g of $Na_2MoO_4.2H_2O$.

YPG medium was composed per liter of 1% yeast extract, 2% bactopeptone, and 5% glucose.

Vogel's $NO_3$ regeneration low-melt medium was composed per liter of 20 ml of 50x Vogels solution with 25 mM $NaNO_3$ stock, 0.8 M sucrose and 1.5% low melting agarose (Sigma Chemical Company, St. Louis, Mo.). Where BASTA™ was added to the medium, BASTA™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use.

50x Vogels solution with 25 mM $NaNO_3$ stock was composed of per liter of 125 g of sodium citrate, 250 g of $KH_2PO_4$, 106.25 g of $NaNO_3$, 10 g of $MgSO_4.7H_2O$, 5 g of $CaCl_2.2H_2O$, 2.5 g of biotin solution, and 5 ml of 50x Vogels trace element solution.

Biotin stock solution was composed of 5 mg of biotin in 100 ml of 50% ethanol. 200x AMG trace metals solution was composed per liter of 3 g of citric acid, 14.3 g of $ZnSO_4.7H_2O$, 2.5 g of $CuSO_4.5H_2O$, 13.8 g of $FeSO_4.7H_2O$, and 8.5 g of $MnSO_4.H_2O$.

STC was composed of 0.8 M sorbitol, 50 mM $CaCl_2$, and 25 mM Tris-Cl, pH 8.

SPTC was composed of 0.8 M sorbitol, 25 mM Tris-HCl, pH 8, 50 mM $CaCl_2$, and 40% PEG 4000.

CM medium was composed per liter of 6 g yeast extract, 6 g casein acid hydrolysate, and 10 g sucrose.

Example 1

Identification of Lipase Genes in the Partial Genomic Sequence of *Aspergillus fumigatus*

A tfasty search (Pearson, W. R., 1999, in *Bioinformatics Methods and Protocols*, S. Misener and S. A. Krawetz, ed., pp. 185-219) of the *Aspergillus fumigatus* partial genome sequence (The Institute for Genomic Research, Rockville, Md.) was carried out using as query a lipase sequence from *Geotrichum candidum* (SWALL P17577). Several genes were identified as putative lipases based upon a high degree of similarity to the query sequence at the amino acid level. A genomic region of approximately 1562 bp with greater than 39% identity to the query sequence at the amino acid level was chosen for further study. Gene models for the putative lipase genes were predicted based on homology to the *Geotrichum candidum* lipase as well as conserved sequences present at the 5' and 3' ends of fungal introns.

Example 2

*Aspergillus fumigatus* Genomic DNA Extraction

*Aspergillus fumigatus* was grown in 250 ml of potato dextrose medium in a baffled shake flask at 37° C. and 240 rpm. Mycelia were harvested by filtration, washed twice in 10 mM Tris-1 mM EDTA (TE), and frozen under liquid nitrogen. Frozen mycelia were ground, by mortar and pestle, to a fine powder, which was resuspended in pH 8.0 buffer containing 10 mM Tris, 100 mM EDTA, 1% Triton X-100, 0.5 M guanidine-HCl, and 200 mM NaCl. DNase-free RNase A was added at a concentration of 20 mg/liter and the lysate was incubated at 37° C. for 30 minutes. Cellular debris was removed by centrifugation, and DNA was isolated using a QIAGEN Maxi 500 column (QIAGEN Inc., Valencia, Calif.). The columns were equilibrated in 10 ml of QBT, washed with 30 ml of QC, and eluted with 15 ml of QF (all buffers from QIAGEN Inc., Valencia, Calif.). DNA was precipitated in isopropanol, washed in 70% ethanol, and recovered by centrifugation. The DNA was resuspended in TE buffer.

Example 3

Cloning of the *Aspergillus fumigatus* Lipase Gene

Two synthetic oligonucleotide primers shown below were designed based on the predicted start and stop codons of the open reading frame to PCR amplify an *Aspergillus fumigatus* gene encoding a lipase from the genomic DNA prepared in Example 2.

```
Forward primer:
                                         (SEQ ID NO: 11)
5'-ACACAACTGGCCATGCATCTCCTCCGGGTTGTTCTG-3'

Reverse primer:
                                         (SEQ ID NO: 12)
5'-AGTCACCTCTAGTTAATTAACTAGATATGGAACGAATCCA-3'
```

Bold letters represent coding sequence. The remaining sequence is homologous to the insertion sites of pBM120a (see Example 6).

The fragment of interest was amplified by PCR using the Expand High Fidelity PCR System (Roche Diagnostics, Mannheim, Germany). One μM of each of the primers above were used in a PCR reaction containing 200 ng of *Aspergillus fumigatus* genomic DNA, 1×PCR buffer (Roche Diagnostics, Mannheim, Germany) with 1.5 mM MgCl$_2$, 1 μl of dNTP mix (10 mM each), and 0.75 μl of DNA polymerase mix (3.5 U/μl; Roche Diagnostics, Mannheim, Germany) in a final volume of 50 μl. To amplify the fragment, an Eppendorf Mastercycler thermocycler (Hamburg, Germany) was programmed for 1 cycle at 94° C. for 2 minutes; 10 cycles each at 94° C. for 15 seconds, 61° C. for 30 seconds, and 72° C. for 1.25 minutes; 15 cycles each at 94° C. for 15 seconds, 61° C. for 30 seconds, and 72° C. for 1.25 minutes plus a 5 second elongation at each successive cycle; 1 cycle at 72° C. for 7 minutes; and a 10° C. hold.

The reaction product was visualized on a 0.7% agarose gel using 44 mM Tris Base, 44 mM boric acid, 0.5 mM EDTA (TBE) buffer and the 1.7 kb product band was purified using a QIAquick PCR Purification Kit (QIAGEN Inc., Valencia, Calif.) according to the manufacturer's instructions. The PCR fragment and pCR2.1-TOPO (Invitrogen, Carlsbad, Calif.) were ligated using conditions specified by the manufacturer resulting in plasmid pJLin173 (FIG. 1).

Two μl of the reaction was used to transform *E. coli* TOP10 One Shot competent cells (Invitrogen, Carlsbad, Calif.) according to the manufacturer's instructions. A 2 μl volume of the ligation mixture was added to the *E. coli* cells and incubated on ice for 5 minutes. Subsequently, the cells were heat shocked for 30 seconds at 42° C., and then placed on ice for 2 minutes. A 250 μl volume of SOC medium was added to the cells and the mixture was incubated for 1 hour at 37° C. and 250 rpm. After the incubation the colonies were spread on 2×YT plates supplemented with 100 μg of ampicillin per ml and incubated at 37° C. overnight for selection of the plasmid. Twelve colonies that grew on the plates were picked with a sterile toothpick and grown overnight at 37° C., 250 rpm in a 15 ml Falcon tube containing 3 ml of LB medium supplemented with 100 μg of ampicillin per ml. An *E. coli* transformant containing the pJLin173 was detected by restriction digestion and plasmid DNA was prepared using a BioRobot 9600 (QIAGEN Inc., Valencia, Calif.).

*E. coli* TOP 10 One Shot cells containing pJLin173 were deposited with the Agricultural Research Service Patent Culture Collection, Northern Regional Research Center, 1815 University Street, Peoria, Ill., 61604, as NRRL B-30782, with a deposit date of Oct. 12, 2004.

Example 4

Characterization of the *Aspergillus fumigatus* Genomic Sequence Encoding Lipase DNA sequencing of the *Aspergillus fumigatus* lipase gene from pJLin173 was performed with an Applied Biosystems Model 377 XL DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

Gene models for the lipase gene were predicted based on homology to the *Geotrichum candidum* lipase as well as conserved sequences present at the 5' and 3' ends of fungal introns. A comparative alignment of amino acid sequences was made using the MAFFT method with iterative refinement and default parameters (Katoh et al., 2002, *Nucleic Acids Research* 30: 3059). The nucleotide sequence (SEQ ID NO: 1) and deduced amino acid sequence (SEQ ID NO: 2) are shown in FIGS. 2A and 2B. The genomic fragment encodes a polypeptide of 562 amino acids. The % G+C content of the gene is 59.7% and of the mature protein coding region (nucleotides 61 to 1686 of SEQ ID NO: 1) is 59.6%. Using the SignalP software program (Nielsen et al., 1997, *Protein Engineering* 10:1-6), a signal peptide of 20 residues was predicted. The predicted mature protein contains 542 amino acids with a molecular mass of 58.7 kDa.

A comparative alignment of lipase sequences was made employing the Clustal W method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* lipase gene shared 35% identity to the deduced amino acid sequence of a *Geotrichum candidum* lipase gene (SWALL P17573).

Example 5

Construction of pAILo1 Expression Vector

Expression vector pAILo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor Site-Directed Mutagenesis Kit (Promega, Madison, Wis.) according to the manufacturer's instructions using the following primers

```
AMDS3NcoMut (2050):
                                         (SEQ ID NO: 13)
5'-GTGCCCCATGATACGCCTCCGG-3'

AMDS2NcoMut (2721):
                                         (SEQ ID NO: 14)
5'-GAGTCGTATTTCCAAGGCTCCTGACC-3'

AMDS1NcoMut (3396):
                                         (SEQ ID NO: 15)
5'-GGAGGCCATGAAGTGGACCAACGG-3'
```

A plasmid comprising all three expected sequence changes was then submitted to site-directed mutagenesis, using a QuickChange Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

Upper Primer to mutagenize the AMG
terminator sequence:
                                            (SEQ ID NO: 16)
5'-CACCGTGAAAGCCATGCTCTTTCCTTCGTGTAGAAGACCAGACAG-3'

Lower Primer to mutagenize the AMG
terminator sequence:
                                            (SEQ ID NO: 17)
5'-CTGGTCTTCTACACGAAGGAAAGAGCATGGCTTTCACGGTGTCTG-3'

Figure 3:
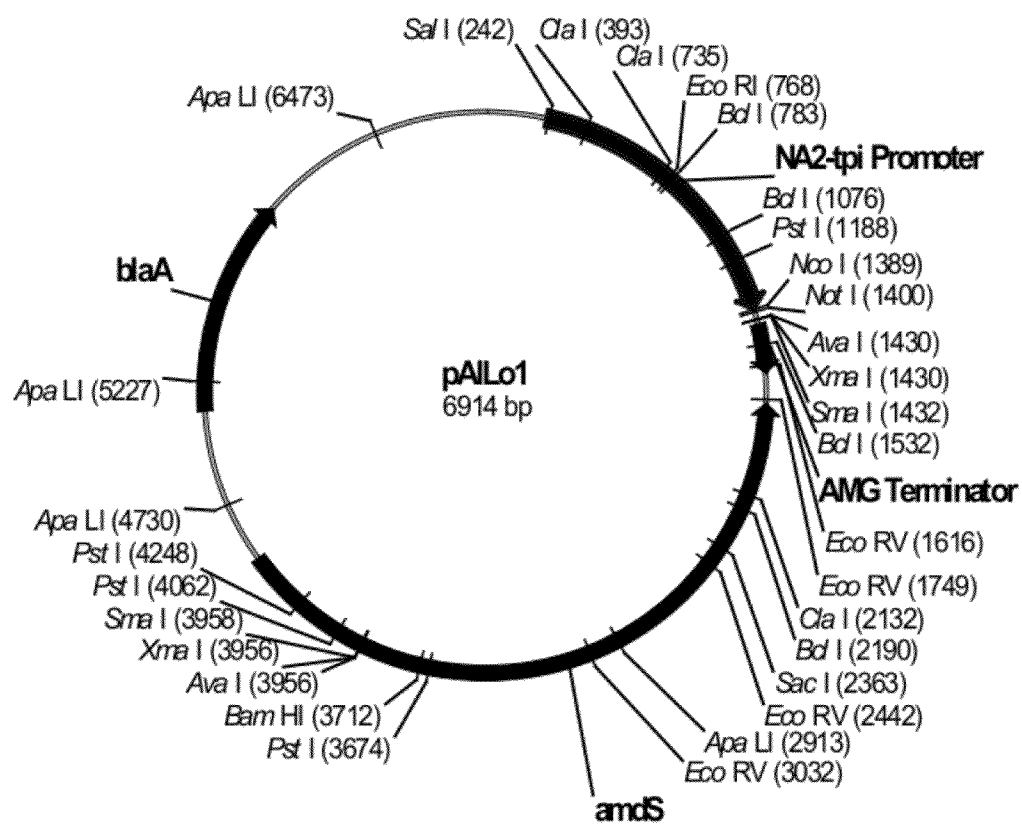
FIG. 3 shows a restriction map of pAILo1.

The last step in the modification of pBANe6 was the addition of a new Nco I restriction site at the beginning of the polylinker using a QuickChange Mutagenesis Kit and the following primers (underlined nucleotides represent the changed bases) to yield pAILo1 (FIG. 3).

Upper Primer to mutagenize the NA2-tpi promoter:
                                            (SEQ ID NO: 18)
5'-CTATATACACAACTGGATTTACCATGGGCCCGCGGCCGCAGATC-3'

Lower Primer to mutagenize the NA2-tpi promoter:
                                            (SEQ ID NO: 19)
5'-GATCTGCGGCCGCGGGCCCATGGTAAATCCAGTTGTGTATATAG-3'

Example 6

Construction of pBM120a Expression Vector

Plasmid pBM120a was constructed to obtain a plasmid containing the double NA2 promoter (NA2-NA2-tpi) for driving gene expression in *Aspergillus* species, and containing the ampicillin resistance gene for selection in *E. coli*.

Primers were designed to PCR amplify the double NA2 promoter from pJaL721 (WO 03/008575). Restriction enzyme sites Sal I and Nco I (underlined) were added for cloning the double promoter into the *Aspergillus* expression plasmid pAILo1.

(SEQ ID NO: 20)
5'-GTCGACATGGTGTTTTGATCATTTTA-3'

(SEQ ID NO: 21)
5'-CCATGGCCAGTTGTGTATATAGAGGA-3'

The fragment of interest was amplified by PCR using the Expand High Fidelity PCR System. The PCR amplification reaction mixture contained 1 µl of 0.09 µg of pJaL721 per µl, 1 µl of each of the primers (50 µmol/µl), 5 µl of 10×PCR buffer with 15 mM $MgCl_2$, 1 µl of a dATP, dTTP, dGTP, and dCTP mix (10 mM each), 37.25 µl of water, and 0.75 µl of DNA polymerase mix (3.5 U/µl). To amplify the fragment, an Eppendorf Mastercycler thermocycler was programmed for 1 cycle at 94° C. for 2 minutes; 10 cycles each at 94° C. for 15 seconds, 55° C. for 30 seconds, and 72° C. for 1.25 minutes; 15 cycles each at 94° C. for 15 seconds, 55° C. for 30 seconds, and 72° C. for 1.25 minutes plus a 5 second elongation at each successive cycle; 1 cycle at 72° C. for 7 minutes; and a 10° C. hold. Ten microliters of this PCR reaction was mixed with 1 µl of 10×DNA loading dye (25% glycerol, 10 mM Tris pH 7.0, 10 mM EDTA, 0.025% bromophenol blue, 0.025% xylene cyanol) and run on a 1.0% (w/v) agarose gel using TBE buffer. The 1128 bp PCR product was observed with UV light on a Nucleotech gel visualization system (Nucleotech, San Mateo, Calif.). The PCR product was directly ligated into pPC2.1-TOPO according to the manufacturer's instructions. A 1 µl volume of fresh PCR product, 3 µl of double-distilled water, and 1 µl of the TOPO cloning vector were mixed with a pipette and incubated at room temperature for 5 minutes.

After the incubation, 2 µl of the mixture was used to transform OneShot competent *E. coli* cells. A 2 µl volume of the ligation mixture was added to the *E. coli* cells and incubated on ice for 5 minutes. Subsequently, the cells were heat shocked for 30 seconds at 42° C., and then placed on ice for 2 minutes. A 250 µl volume of SOC medium was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Eight colonies that grew on the plates were picked with a sterile toothpick and grown overnight at 37° C., 250 rpm in a 15 ml Falcon tube containing 3 ml of LB medium supplemented with 100 µg of ampicillin per ml. The plasmids were isolated using a QIAGEN BioRobot 9600.

Figure 4:
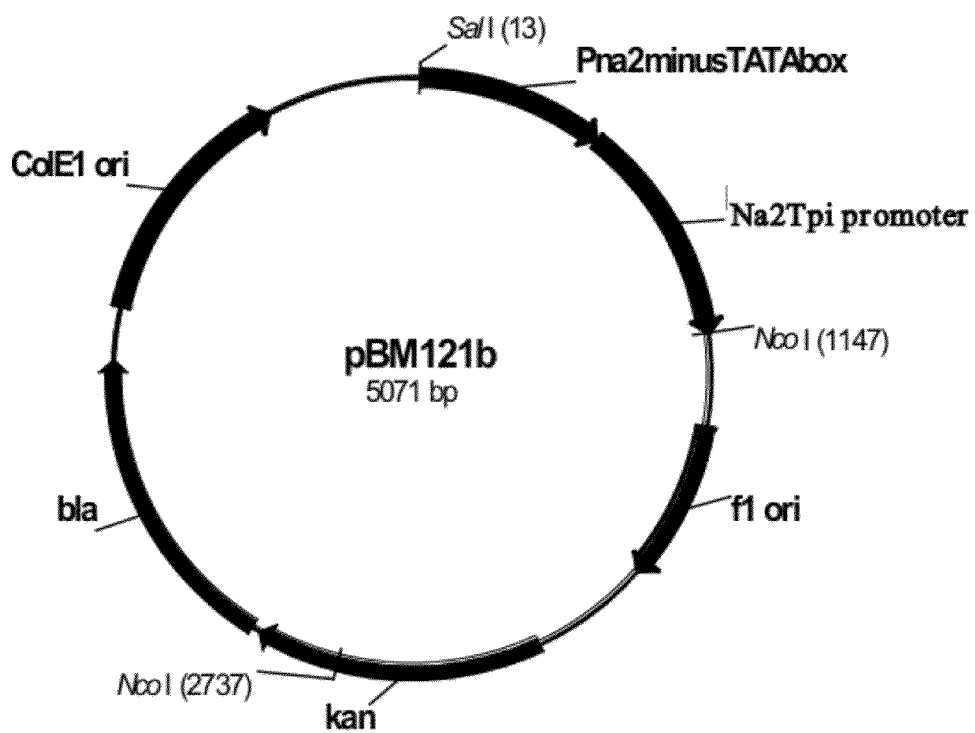
FIG. 4 shows a restriction map of pBM121b.

Four µl volumes of the resulting plasmid minipreps were digested with Eco RI. The digestion reactions were analyzed by agarose gel chromatography and UV analysis as previously described for the PCR reaction. Isolated plasmids containing an insert were sequenced using 1 µl of plasmid template, 1.6 ng of M13 primer (forward or reverse) (MWG Biotech; High Point; NC), and water to 6 µl. DNA sequencing was performed with an Applied Biosystems Model 377 Sequencer XL (Applied Biosystems, Inc., Foster City, Calif.) using dye-terminator chemistry. The resulting plasmid was designated pBM121b (FIG. 4).

Figure 5:
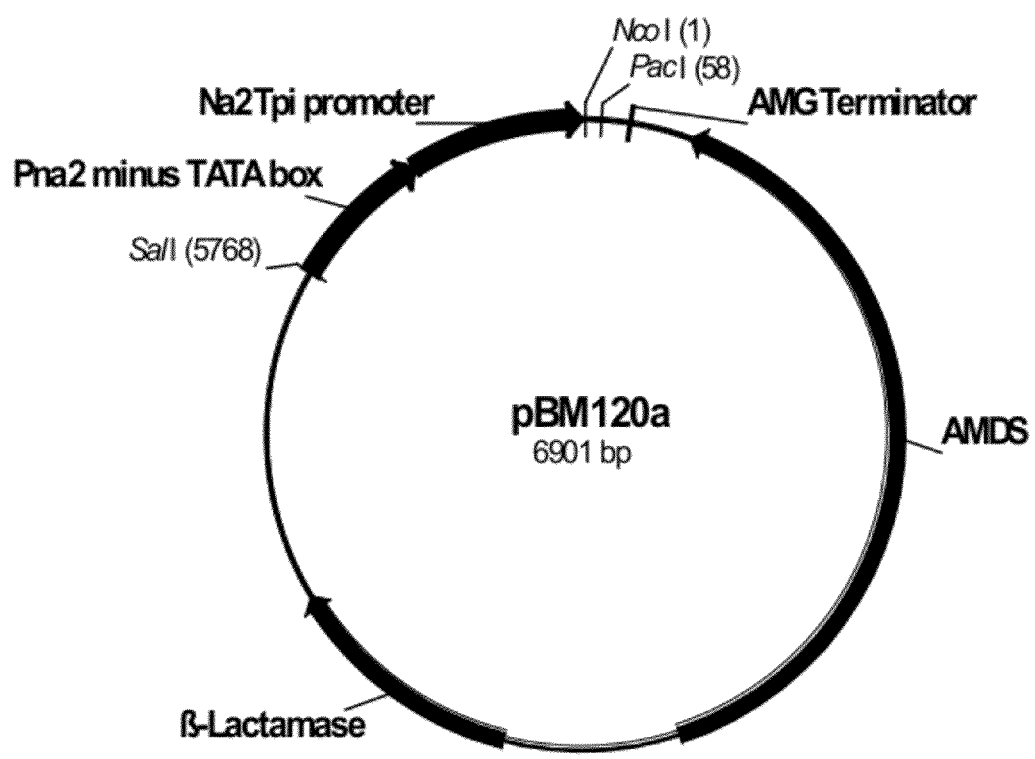

A 5 µl volume of pBM121b was digested with Sal I and Nco I. The digestion reactions were analyzed by agarose gel electrophoresis as described above, and ligated to the vector pAILo1, which had been previously digested with Sal I and Nco I. The resulting expression plasmid was designated pBM120a (FIG. 5).

Example 7

Figure 6:
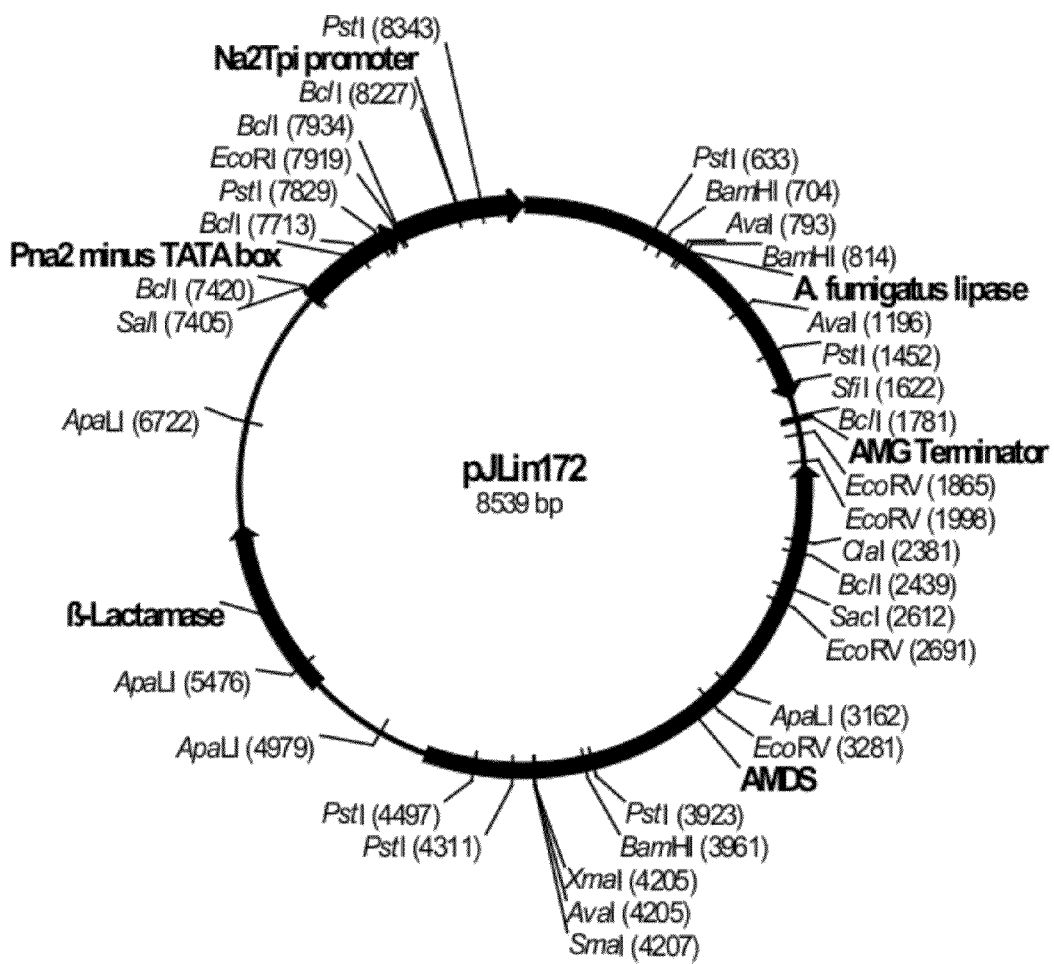
FIG. 6 shows a restriction map of pJLin172.
Figure 7:
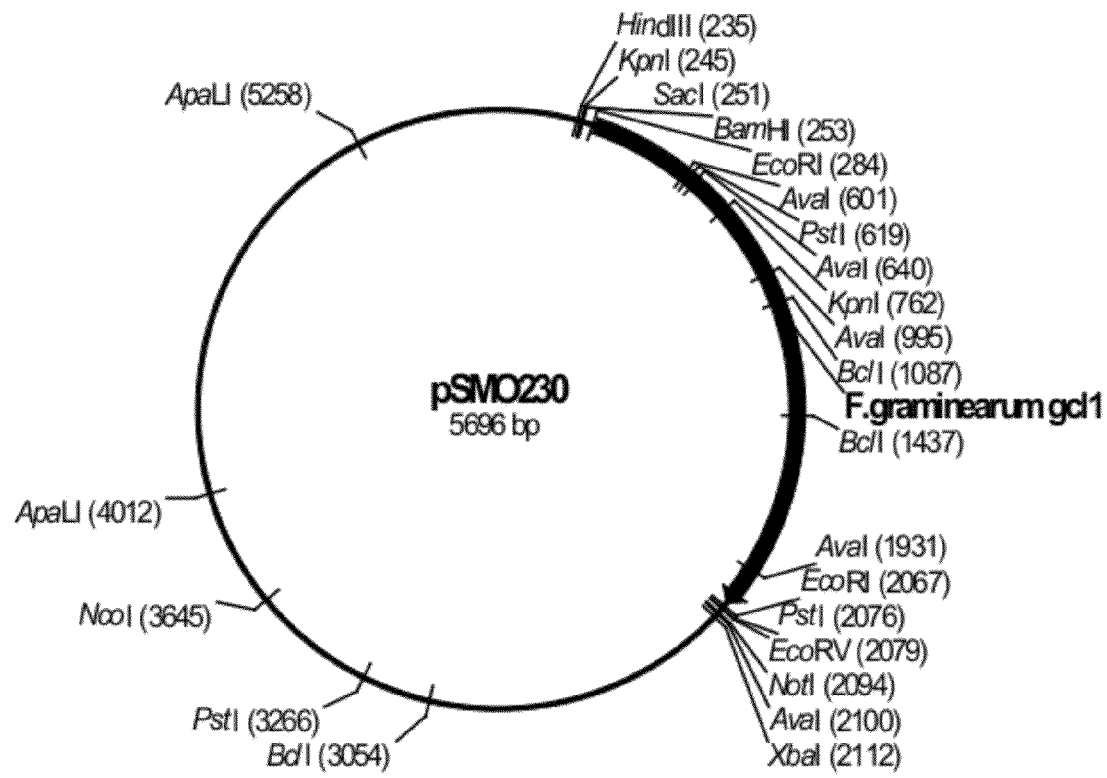
FIG. 7 shows a restriction map of pSMO230.

Construction of an *Aspergillus oryzae* Expression Vector Expressing *Aspergillus fumigatus* Lipase Gene The 1.7 kb PCR fragment (Example 3) containing the *Aspergillus fumigatus* lipase gene was cloned into pBM120a using an InFusion Cloning Kit (BD Biosciences, Palo Alto, Calif.) where the vector was digested with Nco I and Pac I. The digested vector was purified by gel electrophoresis using a 0.7% agarose gel with TBE buffer, and the PCR fragment was extracted using a QIAquick Gel Extraction Kit (QIAGEN Inc., Valencia, Calif.) and purified using a QIAquick PCR Purification Kit. The gene fragment and the digested vector were ligated together in a reaction resulting in the expression plasmid pJLin172 (FIG. 6). The ligation reaction (50 µl) was composed of 1× InFusion Buffer (BD Biosciences, Palo Alto, Calif.), 1×BSA (BD Biosciences, Palo Alto, Calif.), 1 µl of Infusion enzyme (diluted 1:10) (BD Biosciences, Palo Alto, Calif.), 100 ng of pBM120a digested with Nco I and Pac I, and 50 ng of the *Aspergillus fumigatus* lipase gene purified PCR product. The reaction was incubated at room temperature for 30 minutes. Two µl of the reaction was used to transform E. coli SoloPack Gold supercompetent cells (Stratagene, La Jolla, Calif.) according to the manufacturer's instructions. One µl of β-mercaptoethanol was added to competent cells, and incubated on ice for 10 minutes. A 2 µl volume of the ligation mixture was then added to the E. coli cells and incubated on ice for 30 minutes. Subsequently, the cells were heat shocked for 60 seconds at 54° C., and then placed on ice for 2 minutes. A 150 µl volume of NZY+ medium at 42° C. was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Twelve colonies that grew on the plates were picked with a sterile toothpick and grown overnight at 37° C., 250 rpm in a 15 ml Falcon tube containing 3 ml of LB medium supplemented with 100 µg of ampicillin per ml. An E. coli transformant containing the pJLin172 plasmid was detected by restriction digestion and plasmid DNA was prepared using a QIAGEN BioRobot 9600.

Example 8

Expression of the *Aspergillus fumigatus* Lipase Gene in *Aspergillus oryzae* BECh2

*Aspergillus oryzae* BECh2 (Δalp, Δamy, CPA-, KA-, Δnp1) protoplasts were prepared according to the method of Christensen et al., 1988, *Bio/Technology* 6: 1419-1422. Five µg of pJLin172 was used to transform *Aspergillus oryzae* BECh2.

The transformation of *Aspergillus oryzae* BECh2 with pJLin172 yielded 49 transformants. The transformants were isolated to individual Cove plates. Confluent Cove plates of 35 transformants were washed with 4 ml of 0.01% Tween 20. Two hundred µl of spore suspension was inoculated separately into 25 ml of MY25 medium in 125 ml plastic shake flasks and incubated at 34° C., 250 rpm. Three and five days after incubation, culture supernatants were removed for lipase assay and SDS-PAGE analysis.

Lipase activity was determined as follows: 100 µl of substrate (3.92 ml of 100 mM MOPS pH 7.5, 4 mM CaCl$_2$, 990 µl of DMSO, 80 µl of 1% AOS, and 20 µl of p-nitrophenyl butyrate) was added to 100 µl of diluted sample. The samples were diluted accordingly in 100 mM MOPS pH 7.5, 4 mM CaCl$_2$. The absorbance at 405 nm was monitored for 3 minutes at room temperature (25° C.) in a 96-well microtiter plate using a Spectra MAX plate reader (Molecular Devices, Sunnyvale, Calif.).

The lipase assay results indicated that at both 3 and 5 days, 34 of the 35 transformants produced lipase activity well above that of the untransformed control.

SDS-PAGE (BioRad Criterion 10-20% SDS-PAGE) analysis of 10 µl of the supernatants showed a major band at approximately 59 kDa.

Example 9

Determination of Substrate Specificity of Recombinant *Aspergillus fumigatus* Lipase The substrate specificity of *Aspergillus fumigatus* lipase was determined using a panel screen composed of 4-nitrophenol (PNP) lipase substrates.

A panel screen composed of a set of 12 assays utilizing various 4-nitrophenol (PNP) lipase substrates was prepared as described in the Table 1.

TABLE 1

Panel screen of PNP substrates and buffer conditions

| | 1 mM PNP-tagged substrate | Shorthand designation | 50 mM MOPS pH 7.0 | 50 mM CHES pH 9.5 | 50 mM MOPS pH 7.5 | 10 mM CaCl$_2$ | Triton X-100 | PNP Conversion Factors |
|---|---|---|---|---|---|---|---|---|
| 1 | Palmitate | 16:0 | x | | | x | 1.2% | 4.466 |
| 2 | Palmitate | 16:0 | | x | | x | 1.2% | 1.1 |
| 3 | Palmitate | 16:0 | | | x | x | 1.2% | 2.037 |
| 4 | Palmitate | 16:0 | | x | | x | 0.2% | 1.0 |
| 5 | Palmitate | 16:0 | | | x | x | 0.2% | 1.495 |
| 6 | Decanoate | 10:0 | x | | | x | 1.2% | 4.466 |
| 7 | Decanoate | 10:0 | | x | | x | 1.2% | 1.1 |
| 8 | Decanoate | 10:0 | | | x | x | 1.2% | 2.037 |
| 9 | Decanoate | 10:0 | | x | | x | 0.2% | 1.0 |
| 10 | Valerate | 5:0 | | | x | x | 0.40% | 1.630 |
| 11 | Valerate | 5:0 | | | x | x | 0% | 1.370 |
| 12 | Butyrate | 4:0 | | | x | x | 0.40% | 1.630 |

These assays were run in 384-well plates using 8 different dilutions of each sample (7 µl) to be evaluated and 80 µl of the substrates. The assays were incubated for up to 24 hours at ambient temperature. Assays were read at 405 nm at time points of approximately 1, 2, 3, 5, and 24 hours. The results were calculated as OD/hour for each individual assay. In order to make an accurate evaluation of the amount of PNP released, it was necessary to mathematically normalize raw OD values by using a conversion factor. The conversion factors were values, determined experimentally, that were necessary to compensate for the fact that PNP has lower OD readings at low pH and in the presences of detergent (Triton X100) than at pH 9.5. The factor normalizes the data to the OD reading that would have been obtained were it possible to quench the reactions to yield maximal OD for each condition while also stopping the reaction at that time point; i.e., PNP-fatty acid substrates are not stable at high pH, the tag comes off without lipase present at high pH, and the tagged substrate is particularly unstable above pH 9 and for shorter chain length fatty acid substrates.

In Table 1 the top two rows (1 and 2) were the assays used for the pH ratio (9.5/7.0). Rows 3 and 10 were used for the "long chain (Slu)/short chain (Lu); comparisons.

In Table 1 the top two rows (1 and 2) were the assays used for the pH ratio (9.5/7.0). Rows 3 and 10 were used for the "long chain (Slu)/short chain (Lu); comparisons.

LIPEX™, a *Thermomyces lanuginosus* lipase obtained from Novozymes A/S, Bagsvrd, Denmark was used for comparison purposes.

The results for the panel screen are shown in Table 2.

TABLE 2

| | Long chain/Short chain at pH 7.5 | | | |
|---|---|---|---|---|
| | P/V | D/V | P/B | D/B |
| A. fumigatus lipase | 0.04 | 0.15 | 0.05 | 0.16 |
| LIPEX ™ | 0.997 | 1.944 | 2.122 | 4.080 |
| | pH Ratios; (−) = 0.2% Triton data | | | |
| | 9.5P/7.0P | 9.5D/7.0D | 9.5P−/7.5P− | |
| A. fumigatus lipase | 0.36 | 0.22 | Not Tested | |
| LIPEX ™ | 2.072 | 2.574 | 2.251 | |
| | No or Low Triton (−) compared to maximum Triton (+) | | | |
| | V7.5 −/+ | D9.5 +/− | P7.5 +/− | P9.5 +/− |
| A. fumigatus lipase | Not Tested | Not Tested | Not Tested | Not Tested |
| LIPEX ™ | 7.108 | 5.110 | 9.331 | 8.166 |

The data for the *Aspergillus fumigatus* lipase was generated in 96-well plate format using approximately 3 times the sample and substrate volumes as described in Table 1. *Aspergillus fumigatus* lipase test data consists of the average of 2 assay results; and LIPEX ™ data consists of the average of a minimum of 80 assay results.
Ratio of PNP-substrates according to Table 1, Example 9, where: P = Palmitate, D = Decanoate, V = Valerate and B = Butyrate In comparing the panel screen results of LIPEX™ and the *Aspergillus fumigatus* lipase the following observations were made:

1. The ratio of activities on PNP-palmitate at pH 9.5 versus pH 7 is 6-fold lower for the *Aspergillus fumigatus* lipase versus LIPEX™ suggesting that the *Aspergillus fumigatus* lipase has lower activity at pH 9.5 versus LIPEX™ or it has a higher activity at pH 7.0 than LIPEX™ or a combination of these two.

2. The ratios of P/V, D/V, and D/B are also quite different for the *Aspergillus fumigatus* lipase versus LIPEX™ suggesting there is some acyl change length specificity differences between the two lipases.

Example 10

Purification and Characterization of Recombinant *Aspergillus fumigatus* Lipase

One of the *Aspergillus oryzae* transformants producing the highest yield of *Aspergillus fumigatus* lipase (Example 8) was grown in 500 ml of MY25 medium for 4 days at 30° C., 250 rpm for purification. Supernatant was sterile filtered under pressure using SEITZ-EKS filters (PALL Corporation, Waldstetten, Germany). The sterile filtered supernatant was diluted with distilled water so the conductivity was under 4 mSi abd then the pH was adjusted to 7.

Source Q™ (Pharmacia Amersham, Uppsala, Sweden) was packed into a 50 ml column and then washed and equilibrated with 50 mM borate pH 7 buffer. Filtered fermentation supernatant was then applied to the column using an Akta Explorer System (Pharmacia Amersham, Uppsala, Sweden). Unbound material was washed with 50 mM borate pH 9 buffer. The bound proteins were eluted with 50 mM borate pH 9 buffer containing 0.5 M sodium chloride as an eluent. The total length of the gradient was approximately 20 column volumes.

Fractions of 10 ml were collected and analyzed for lipase activity according to the assay described by Svendsen et al., in *Methods in Enzymology*, Lipases Part a Biotechnology Vol. 284 pages 317-340 Edited by Byron Rubin and Edward A. Dennis, Academic Press, 1997, New York. Aliquots of fractions were analyzed for purity by standard SDS-PAGE procedure using Novex 4-20% Tris-glycine gels (Invitrogen Life Technologies, Carlsbad Calif.). The most pure fractions were pooled on the basis of LU activity and purity assessed by SDS-PAGE. The purity of the pooled fractions by SDS-PAGE was determined to be more than 95% with a molecular of approximately 68 kDa.

Substrate specificity of the *Aspergillus fumigatus* lipase was evaluated at pH 7 according to WO 2005/040410. The results showed that the *Aspergillus fumigatus* lipase efficiently degrades trilinolein and cholesterol linoleate whereas activity toward phospholipids such as lecithin (and alkylated phosphatidylethanolamines) is much lower.

Example 11

Determination of Thermostability of Recombinant *Aspergillus fumigatus* Lipase

The thermostability of the purified recombinant *Aspergillus fumigatus* lipase (Example 10) was determined by Differential Scanning Calorimetry (DSC). The thermal denaturation temperature, Td, was taken as the top of the denaturation peak (major endothermic peak) in thermograms (Cp vs. T) obtained after heating of enzyme solutions at a constant programmed heating rate. Cp refers to heat capacity (at constant pressure). T refers to temperature.

A VP-DSC Differential Scanning Calorimeter (MicroCal Inc., Northampton, Mass.) was used for the thermostability determination according to the manufacturer's instructions. Sample enzyme and reference solutions were carefully degassed immediately prior to loading of samples into the calorimeter (reference: buffer without enzyme). Sample enzyme (approximately 1 mg/ml) and reference solutions (approximately 0.5 ml) were thermally pre-equillibrated for 20 minutes at 5° C. The DSC scan was performed from 5° C. to 95° C. at a scan rate of approximately 90 K/hr. Denaturation temperatures were determined at an accuracy of approx. +/−1° C.

The results as shown in Table 3 indicated that the *Aspergillus fumigatus* lipase had thermal denaturation temperatures of 60° C. in 50 mM acetate pH 5.0 buffer, 54° C. in 50 mM HEPES pH 7.0 buffer, and 44° C. in 50 mM glycine pH 10.0 buffer.

TABLE 3

| Thermostability Determination | | |
|---|---|---|
| Buffer | pH | Td (° C.) |
| 50 mM Acetate | 5.0 | 60 |
| 50 mM HEPES | 7.0 | 54 |
| 50 mM Glycine | 10.0 | 44 |

Example 12

Identification of Lipase Genes in the Partial Genomic Sequence of *Fusarium graminearum*

The assembly 1 protein sequences deduced from the *Fusarium graminearum* partial genome sequence (Broad Institute, MIT) were downloaded into a Microsoft Word document. A search was done for sequences containing the GESAG motif, which is the conserved sequence around the active site serine residue in *Geotrichum candidum* lipases (EMBL Accession Nos. U02622 and U02541) and homologs thereof. Several sequences were found to contain the GESAG motif and those with a suitable size and additional conserved residues close to the GESAG motif were aligned in full length with the *Geotrichum candidum* lipases and homologs. The hypothetical protein FG01603.01 with a length of 591 amino acids was found to be clearly the best match. However, when the corresponding DNA was translated, it was found that the C-terminal sequence was more likely to be GALVV rather than GALVDTNG as in FG01603.01.

Example 13

*Fusarium graminearum* Genomic DNA Extraction

*Fusarium graminearum* was grown in 100 ml of M400 medium in a baffled shake flask at 24° C. and 200 rpm. Mycelia were harvested by filtration, washed twice in TE, and frozen under liquid nitrogen. Frozen mycelia were ground, by mortar and pestle, to a fine powder, which was resuspended in pH 8.0 buffer containing 10 mM Tris, 100 mM EDTA, 1% Triton X-100, 0.5 M guanidine-HCl, and 200 mM NaCl. DNase free RNase A was added at a concentration of 20 mg/liter and the lysate was incubated at 37° C. for 30 minutes. Cellular debris was removed by centrifugation, and DNA was isolated using a QIAGEN Maxi 500 column. The columns were equilibrated in 10 ml of QBT, washed with 30 ml of QC, and eluted with 15 ml of QF. DNA was precipitated in isopropanol, washed in 70% ethanol, and recovered by centrifugation. The DNA was resuspended in TE buffer.

Example 14

Cloning of a *Fusarium graminearum* Lipase Gene

Two synthetic oligonucleotide primers shown below were designed based on the predicted start and stop codons of the open reading frame to PCR amplify a *Fusarium graminearum* lipase gene from the genomic DNA prepared in Example 13.

```
Forward primer:
                                         (SEQ ID NO: 22)
5'-CACTGCTATCACCAACATGAGATTCTCTGG-3'

Reverse primer:
                                         (SEQ ID NO: 23)
5'-CCAACAAGGTATTTAATTAATCATACCACCAAAGC-3'
```

Bold letters represent coding sequence.

The fragment of interest was amplified by PCR using the Expand High Fidelity PCR System. One μM of each of the primers above were used in a PCR reaction containing 200 ng of pSMO232 (Example 6), 1×PCR buffer with 1.5 mM $MgCl_2$, 1 μl of dNTP mix (10 mM each), and 0.75 μl of DNA polymerase mix (3.5 U/μl) in a final volume of 50 μl. To amplify the fragment, an Eppendorf Mastercycler Thermocycler was programmed for 1 cycle at 94° C. for 2 minutes; 10 cycles each at 94° C. for 15 seconds, 60° C. for 30 seconds, and 72° C. for 1.25 minutes; 15 cycles each at 94° C. for 15 seconds, 60° C. for 30 seconds, and 72° C. for 1.25 minutes plus a 5 second elongation at each successive cycle; 1 cycle at 72° C. for 7 minutes; and a 10° C. hold.

The reaction product was visualized on a 0.8% agarose gel using TBE buffer and a 1.8 kb product band was purified using a QIAquick PCR Purification Kit according to the manufacturer's instructions.

The PCR fragment and pCR2.1-TOPO vector were ligated using conditions specified by the manufacturer to produce pSMO230 (FIG. 7). Two μl of the reaction was used to transform *E. coli* TOP10 One Shot competent cells according to the manufacturer's instructions. A 2 μl volume of the ligation mixture was added to the *E. coli* cells and incubated on ice for 20 minutes. Subsequently, the cells were heat shocked for 30 seconds at 42° C., and then placed on ice for 2 minutes. A 250 μl volume of SOC medium was added to the cells and the mixture was incubated for 1 hour at 37° C. and 250 rpm. After the incubation the colonies were spread on 2×YT plates supplemented with 100 μg of ampicillin per ml and incubated at 37° C. overnight for selection of the plasmid. Sixteen colonies that grew on the plates were picked with a sterile toothpick and grown overnight at 37° C., 250 rpm in a 15 ml Falcon tube containing 3 ml of LB medium supplemented with 100 μg of ampicillin per ml. An *E. coli* transformant containing a plasmid designated pSMO230 was detected by restriction digestion and plasmid DNA was prepared using a BioRobot 9600.

*E. coli* TOP10 One Shot cells containing pSMO23O were deposited with the Agricultural Research Service Patent Culture Collection, Northern Regional Research Center, 1815 University Street, Peoria, Ill., 61604, as NRRL B-30803, with a deposit date of Dec. 17, 2004.

Example 15

Characterization of the *Fusarium graminearum* Genomic Sequence Encoding Lipase DNA sequencing of the *Fusarium graminearum* lipase gene from pSMO230 was performed with an Applied Biosystems Model 377 XL DNA Sequencer (Perkin-Elmer/Applied Biosystems, Inc., Foster City, Calif.) using dye-terminator chemistry (Giesecke et al., 1992, supra) and primer walking strategy. Nucleotide sequence data were scrutinized for quality and all sequences were compared to each other with assistance of PHRED/PHRAP software (University of Washington, Seattle, Wash.).

Gene models for the sequence were constructed based on the tfasty output and alignment with a homologous lipase gene from *Geotrichum candidum* (SWALL P17577). A comparative alignment of amino acid sequences was made using the MAFFT method with iterative refinement and default parameters (Katoh et al., 2002, supra). The nucleotide sequence (SEQ ID NO: 3) and deduced amino acid sequence (SEQ ID NO: 4) are shown in FIGS. 8A and 8B. The genomic fragment encodes a polypeptide of 588 amino acids. The % G+C content of the gene is 52.5% and the mature protein coding region (nucleotides 73 to 1764) is 52.4%. Using the SignalP software program (Nielsen et al., 1997, supra), a signal peptide of 24 residues was predicted. The predicted mature protein contains 564 amino acids with a molecular mass of 63 kDa.

A comparative alignment of lipase sequences was made employing the Clustal W method (Higgins, 1989, supra) using LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Fusarium graminearum* lipase gene shared 23% identity to the deduced amino acid sequence of a *Geotrichum candidum* lipase gene (SWALL P17577).

Example 16

Construction of pEJG61

The *Fusarium venenatum* expression vector pEJG61 was generated by modification of pSheB1 (U.S. Pat. No. 6,090,604). The modifications included (a) changing the single Bsp LU11I site in pSheB1 by site-directed mutagenesis (b) replacement of 930 bp of the *Fusarium oxysporum* trypsin promoter with 2.1 kilobases of the *Fusarium venenatum* glucoamylase promoter, and (c) introduction of a Bsp LU11I site after the *Fusarium venenatum* glucoamylase promoter.

Removal of the Bsp LU11I site within the pSheB1 sequence was accomplished using the QuikChange™ Site-Directed Mutagenesis Kit (Stratagene Cloning Systems, La Jolla, Calif.) according to the manufacturer's instruction with the following pairs of mutagenesis primers:

```
                                         (SEQ ID NO: 24)
5'-GCAGGAAAGAACAAGTGAGCAAAAGGC-3'

(SEQ ID NO: 25)
5'-GCCTTTTGCTCACTTGTTCTTTCCTGC-3'
```

This created pSheB1 intermediate 1.

Removal of 930 bp of the *Fusarium oxysporum* trypsin promoter was accomplished by digesting pSheB1 intermediate 1 (6,971 bp) with Stu I and Pac I, subjecting the digest to electrophoresis on a 1% agarose gel, at 100 volts for one hour using TBE buffer, excising the 6,040 bp vector fragment, and purifying the excised fragment with a Qiaquick Gel Purification Kit (QIAGEN Inc., Valencia, Calif.). To introduce a new Bsp LU11I site, a linker was created using

```
5'-dCCTACATGTTTAAT-3'        (SEQ ID NO: 26)
       Bsp Lu11I
5'-dTAAACATGTAGG-3'           (SEQ ID NO: 27)
```

Each primer (2 μg each) was heated to 70° C. for 10 minutes and then cooled to room temperature over an hour. This linker was ligated into the Stu I-Pac I digested pSheB1 intermediate 1 vector fragment, creating pSheBI intermediate 2.

A 2.1 kilobase fragment of *Fusarium venenatum* genomic DNA 5 prime of the glucoamylase coding region (glucoamylase promotor) was isolated by PCR of plasmid pFAMG (WO 00/56900) containing *Fusarium venenatum* genomic DNA encoding the entire coding region for *Fusarium venenatum* glucoamylase and 3,950 bp of upstream sequence. The

```
                                         (SEQ ID NO: 28)
5'-AGGCCTCACCCATCTCAACAC-3'

(SEQ ID NO: 29)
5'-ACATGTTGGTGATAGCAGTGA-3'
```

The PCR reaction (50 μl) was composed of 200 ng of pFAMG, 200 μM dNTPs, 1 μM of the above primers, 1× reaction buffer, and 2.6 units of Expand High Fidelity enzyme mix. The reactions were incubated using a MJ Research Thermocycler (MJ Research, Inc., Boston, Mass.) programmed for 1 cycle 1 at 94° C. for 2 minutes; 10 cycles each at 94° C. for 15 seconds, 60° C. for 30 sec, and 72 C for 2 minutes and 15 seconds; 15 cycles each at 94° C. for 15 seconds, 60° C. for 30 seconds, and 72° C. for 2 minutes and 15 seconds with 5 seconds cycle elongation for each successive cycle; and 1 cycle at 72° C. for 7 minutes.

Figure 9:
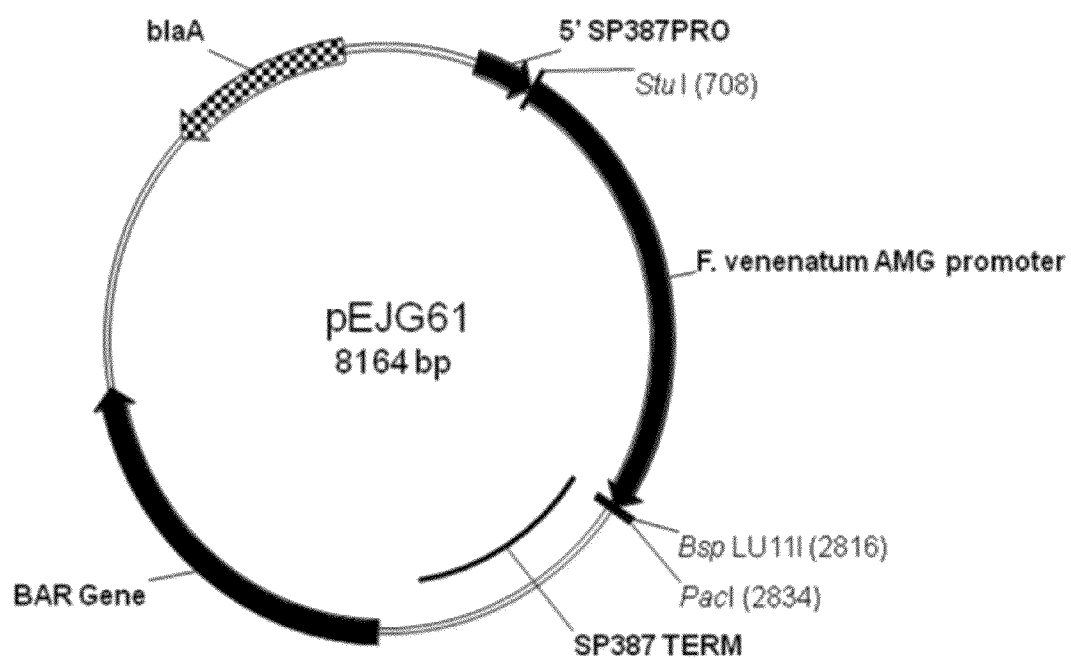
FIG. 9 shows a restriction map of pEJG61.

The PCR product was subjected to electrophoresis on a 1% agarose gel at 100 volts for one hour using TBE buffer generating an expected band of 2,108 bp. The 2,108 bp PCR product was excised from the agarose gel and purified with a Qiaquick Gel Purification Kit. This fragment was digested with Stu I and Bsp LU11I, purified with a Qiaquick Purification Kit (QIAGEN Inc., Valencia, Calif.), and ligated into Stu I-Bsp LU11I digested pSheBI intermediate 2 creating pEJG61 (FIG. 9).

Example 17

Construction of a *Fusarium venenatum* Expression Vector Expressing *Fusarium graminearum* Lipase Gene The two synthetic oligonucleotide primers described in Example 14 were designed to PCR amplify the *Fusarium graminearum* lipase gene from the genomic DNA prepared in Example 13.

The fragment of interest was amplified by PCR using the Herculase™ Hotstart PCR System (Stratagene, La Jolla, Calif.). One μM of each of the primers above were used in a PCR reaction containing 20 ng of *Fusarium graminerum* genomic DNA, 1×PCR buffer (Stratagene, La Jolla, Calif.), 1 μl of dNTP mix (10 mM each), and 1.0 μl of DNA polymerase mix (5 U/μl; Stratagene, La Jolla, Calif.) in a final volume of 50 μl. To amplify the fragment, an Eppendorf Mastercycler thermocycler was programmed for 1 cycle at 94° C. for 2 minutes; 10 cycles each at 94° C. for 15 seconds, 60° C. for 30 seconds, and 72° C. for 1.25 minutes; 15 cycles each at 94° C. for 15 seconds, 60° C. for 30 seconds, and 72° C. for 1.25 minutes plus a 5 second elongation at each successive cycle; 1 cycle at 72° C. for 7 minutes; and a 10° C. hold.

The reaction product was visualized on a 0.8% agarose gel using TBE buffer and the 1.8 kb product band was purified using a QIAquick PCR Purification Kit according to the manufacturer's instructions.

Figure 10:
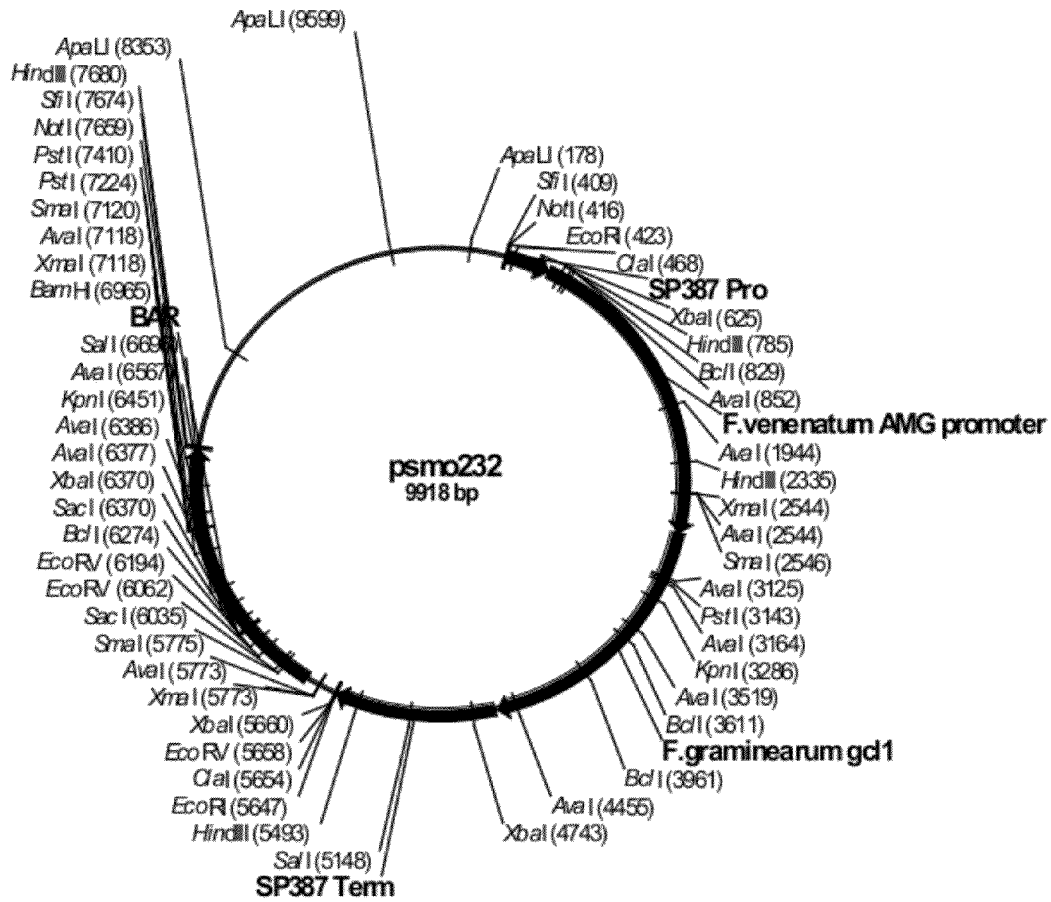
FIG. 10 shows a restriction map of pSMO232.
Figure 11:
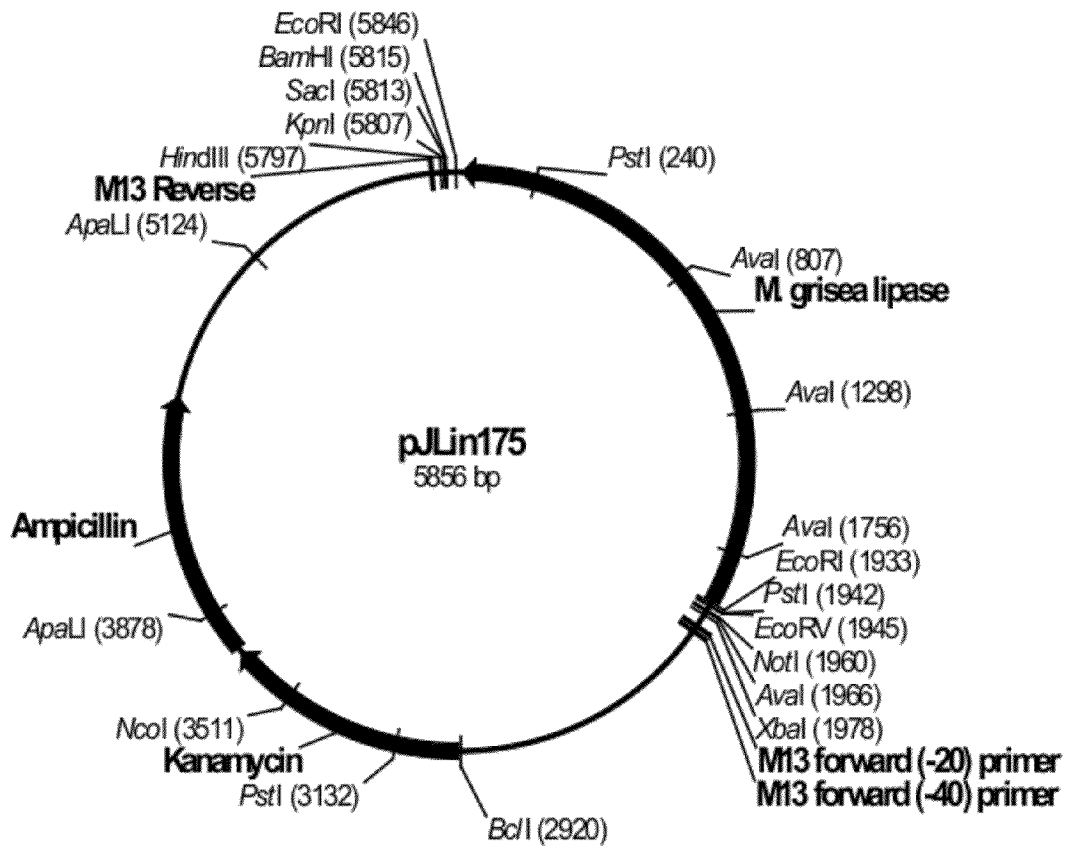
FIG. 11 shows a restriction map of pJLin175.

The 1.8 kb PCR fragment containing the *Fusarium graminearum* lipase gene was cloned into pEJG61 using an InFusion Cloning Kit where the vector was digested with Bsp LU11I and Pac I. The digested vector was purified by gel electrophoresis using a 0.7% agarose gel with TBE buffer, and the PCR fragment was extracted using a QIAquick Gel Extraction Kit and purified using a QIAquick PCR Purification Kit. The gene fragment and the digested vector were ligated together in a reaction resulting in the expression plasmid pSMO232 (FIG. 10). The ligation reaction (50 μl) was composed of 1× InFusion Buffer, 1×BSA, 1 μl of Infusion enzyme (diluted 1:10), 100 ng of pEJG61 digested with Bsp LU11I and Pac I, and 50 ng of the *Fusarium graminearum* lipase gene purified PCR product. The reaction was incubated at room temperature for 30 minutes. Two μl of the reaction was used to transform *E. coli* SoloPack Gold supercompetent cells according to the manufacturer's instructions. One μl of 3-mercaptoethanol was added to the competent cells, and incubated on ice for 10 minutes. A 2 μl volume of the ligation mixture was then added to the *E. coli* cells and incubated on ice for 30 minutes. Subsequently, the cells were heat shocked for 60 seconds at 54° C., and then placed on ice for 2 minutes. A 150 μl volume of NZY+ medium at 42° C. was added to the cells and the mixture was incubated for 1 hour at 37° C. and 250 rpm. After the incubation the colonies were spread on 2×YT plates supplemented with 100 μg of ampicillin per ml and incubated at 37° C. overnight for selection of the plasmid. Nine colonies that grew on the plates were picked with a sterile toothpick and grown overnight at 37° C., 250 rpm in a 15 ml Falcon tube containing 3 ml of LB medium supplemented with 100 μg of ampicillin per ml. An *E. coli* transformant containing pSMO232 was detected by restriction digestion and plasmid DNA was prepared using a QIAGEN BioRobot 9600.

Example 18

Expression of the *Fusarium graminearum* Lipase Gene in *Fusarium venenatum* WTY842-1-11

Spores of *Fusarium venenatum* strain WTY842-1-11 (Δtrichodiene synthase gene, amdS+) a mutant of *Fusarium* strain A3/5 (NRRL 30747 or ATCC 20334) (Wiebe et al., 1992, *Mycological Research* 96: 555-562; Wiebe et al., 1991, *Mycological Research* 95: 1284-1288; Wiebe et al., 1991, *Mycological Research* 96: 555-562), were generated by inoculating a flask containing 100 ml of RA sporulation medium with 8 plugs from an agar plate and incubated at 27° C., 150 rpm for 24 hours, then 24 hours, 150 rpm at 22° C. Spores were harvested by filtering culture through MIRACLOTH™ (Calbiochem, La Jolla, Calif.) onto a Nalgene 0.2 μm filter. Wash spores twice with sterile distilled water, resuspended in a small volume of water, and then counted using a hemocytometer.

Protoplasts were prepared by inoculating 100 ml of YPG medium with 2×10$^8$ spores of *Fusarium venenatum* WTY842-1-11 and incubating for 15 hours at 18° C. and 150 rpm. The culture was filtered through MIRACLOTH™, washed once with sterile distilled water and once with 1 M MgSO$_4$ and resuspended in 40 ml of 5 mg/ml of NOVOZYME 234™ (Novozymes A/S, Bagsærd, Denmark) in 1 M MgSO$_4$. Cultures were incubated at 29° C. and 90 rpm until protoplasts formed. A volume of 30 ml of 1 M sorbitol was added to the protoplast digest and the mixture was centrifuged at 1500 rpm for 10 minutes. The pellet was resuspended, washed twice with 1 M sorbitol, and centrifuged at 1500 rpm for 10 minutes to pellet the protoplasts. Protoplasts were counted with a hemocytometer and resuspended in an 8:2:0.1 solution of STC:SPTC:DMSO to a final concentration of 5×10$^7$ protoplasts/ml. The protoplasts were stored at −80° C., after controlled-rate freezing in a Nalgene Cryo 1° C. Freezing Container.

Two ml of protoplast suspension were added to 20 μg of pSMO232 and 250 μg of heparin in a 50 ml Falcon tube, mixed and incubated on ice for 30 minutes. Two hundred μl of SPTC was mixed gently into the protoplast suspension and incubation was continued at room temperature for 10 minutes. Twenty ml of SPTC was mixed gently into the protoplast suspension and incubation was continued at room temperature for 10 minutes. A 350 ml volume of molten Vogel's NO$_3$ regeneration low-melt medium (cooled to 50° C.) was mixed with the protoplasts and then 35 ml were plated onto 100 mm Petri plate containing 35 ml of the identical medium plus 12 mg of BASTA™ per ml. Incubation was continued at room temperature for 6 days. After 6 days, 29 transformants were apparent. A mycelial fragment from the edge of each transformant was transferred to plates containing Vogel's NO$_3$ regeneration low-melt medium plus BASTA™ (6 mg/ml) medium. The plate was sealed in a plastic bag to maintain moisture and incubated approximately one week at room temperature.

One cm$^2$ of spore growth was inoculated separately into 25 ml of MY400 medium in 125 ml plastic shake flasks and incubated at 28° C., 250 rpm. Three and five days after incubation, culture supernatants were removed for lipase assay and SDS-PAGE analysis.

Lipase activity was determined as described in Example 12. The lipase assay results indicated that at 3 days several of the transformants produced lipase activity above that of the untransformed control. SDS-PAGE analysis (BioRad Criterion 10-20% SDS-PAGE) of 10 μl of the supernatants showed a band at approximately 61 kDa.

Example 19

Determination of Substrate Specificity of Recombinant *Fusarium graminearum* Lipase The substrate specificity of the *Fusarium graminearum* lipase was determined using a panel screen composed of 4-nitrophenol (PNP) lipase substrates as described in Example 9.

The results for the panel screen are shown in Table 4.

TABLE 4

| | Long chain/Short chain at pH 7.5 | | | |
|---|---|---|---|---|
| | P/V | D/V | P/B | D/B |
| *F. graminearum* lipase | 0.769 | 0.772 | 0.398 | 0.399 |
| LIPEX ™ | 0.997 | 1.944 | 2.122 | 4.080 |

| | pH Ratios; (−) = 0.2% Triton data | | |
|---|---|---|---|
| | 9.5P/7.0P | 9.5D/7.0D | 9.5P−/7.5P− |
| *F. graminearum* lipase | 0.138 | 0.393 | Not Tested |
| LIPEX +198 | 2.072 | 2.574 | 2.251 |

| | No or Low Triton (−) compared to maximum Triton (+) | | | |
|---|---|---|---|---|
| | V7.5 −/+ | D9.5 +/− | P7.5 +/− | P9.5 +/− |
| *F. graminearum* lipase | Not Tested | Not Tested | Not Tested | Not Tested |
| LIPEX ™ | 7.108 | 5.110 | 9.331 | 8.166 |

*Fusarium graminearum* lipase (*Fusarium venenatum* WTY-842-1-11 expressing *Fusarium graminearum* lipase 1) test data consists of the average of 2 assay results; and LIPEX ™ data consists of the average a minimum of 8 of 80 assay results.
Ratio of PNP-substrates according to Table 1, Example 9, where: P = Palmitate, D = Decanoate, V = Valerate and B = Butyrate In comparing the panel screen results of LIPEX™ and the *Fusarium graminearum* lipase the following observations were made:

1. The ratio of activities on PNP-palmitate at pH 9.5 versus pH 7 is 16-fold lower for the *Fusarium graminearum* lipase versus LIPEX™ suggesting that the *Fusarium graminearum* lipase has much lower activity at pH 9.5 versus LIPEX™ or it has a much higher activity at pH 7.0 than LIPEX™ or a combination of these two.

2. The ratios of PN, DN, and D/B are also quite different for the *Fusarium graminearum* lipase versus LIPEX™ suggesting there is some acyl change length specificity differences between the two lipases.

Example 20

Identification of Lipase Genes in the Partial Genomic Sequence of *Magnaporthe grisea*

A tfasty search (Pearson, W. R., 1999, supra) of the *Magnaporthe grisea* partial genome sequence (The Institute for Genomic Research, Rockville, Md.) was carried out using as query a lipase sequence from *Geotrichum candidum* (SWALL P17573). Several genes were identified as putative lipases based upon a high degree of similarity to the query sequence at the amino acid level. Two genomic regions of approximately 1400 bp and 110 bp with greater than 33% identity to the query sequence at the amino acid level were chosen for further study. Gene models for the putative lipase genes were predicted based on homology to the *Geotrichum candidum* lipase as well as conserved sequences present at the 5' and 3' ends of fungal introns.

Example 21

*Magnaporthe grisea* Genomic DNA Extraction

Four hundred µl of *Magnaporthe grisea* (FGSC 8958, Fungal Genetics Stock Center) spores were grown in 50 ml of CM medium in a baffled shake flask at 25° C. and 250 rpm for 4 days. Genomic DNA was then extracted from the mycelia using a DNeasy Plant Mini Kit (QIAGEN Inc., Valencia, Calif.) according to manufacturer's instructions.

Example 22

Cloning of the *Magnaporthe grisea* Lipase 1 Gene

Two synthetic oligonucleotide primers shown below were designed based on the predicted start and stop codons of the open reading frame to PCR amplify a *Magnaporthe grisea* gene encoding a lipase 1 from the genomic DNA prepared in Example 21.

```
Forward primer:
                                        (SEQ ID NO: 30)
5'-ACACAACTGGCCATGAAAGCCTCCATTCTTTCGGCT-3'

Reverse primer:
                                        (SEQ ID NO: 31)
5'-AGTCACCTCTAGTTAATTAATTAAATGTAAAAGCTGAGGA-3'
```

Bold letters represent coding sequence. The remaining sequence is homologous to the insertion sites of pBM120a (see Example 6).

The fragment of interest was amplified by PCR using the Expand High Fidelity PCR System. One µM of each of the primers above were used in a PCR reaction containing 300 ng of *Magnaporthe grisea* genomic DNA, 1×PCR buffer with 1.5 mM $MgCl_2$, 1 µl of dNTP mix (10 mM each), and 0.75 µl of DNA polymerase mix (3.5 U/µl) in a final volume of 50 µl. To amplify the fragment, an Eppendorf Mastercycler thermocycler was programmed for 1 cycle at 94° C. for 2 minutes; 10 cycles each at 94° C. for 15 seconds, 59.2° C. for 30 seconds, and 72° C. for 1.25 minutes; 15 cycles each at 94° C. for 15 seconds, 59.2° C. for 30 seconds, and 72° C. for 1.25 minutes plus a 5 second elongation at each successive cycle; 1 cycle at 72° C. for 7 minutes; and a 10° C. hold.

The reaction product was visualized on a 0.7% agarose gel using TBE buffer and the 2 kb product band was purified using a QIAquick PCR Purification Kit according to the manufacturer's instructions. The PCR fragment and pCR2.1-TOPO were ligated using conditions specified by the manufacturer resulting in plasmid pJLin175 (FIG. 11).

Two µl of the reaction was used to transform *E. coli* TOP10 One Shot competent cells according to the manufacturer's instructions. A 2 µl volume of the ligation mixture was added to the *E. coli* cells and incubated on ice for 5 minutes. Subsequently, the cells were heat shocked for 30 seconds at 42° C., and then placed on ice for 2 minutes. A 250 µl volume of SOC medium was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Twelve colonies that grew on the plates were picked with a sterile toothpick and grown overnight at 37° C., 250 rpm in a 15 ml Falcon tube containing 3 ml of LB medium supplemented with 100 µg of ampicillin per ml. An *E. coli* transformant containing the pJLin175 was detected by restriction digestion and plasmid DNA was prepared using a BioRobot 9600.

*E. coli* TOP 10 One Shot cells containing pJLin175 were deposited with the Agricultural Research Service Patent Culture Collection, Northern Regional Research Center, 1815 University Street, Peoria, Ill., 61604, as NRRL B-30783, with a deposit date of Oct. 12, 2004.

Example 23

Characterization of the *Magnaporthe grisea* Genomic Sequence Encoding Lipase 1

DNA sequencing of the *Magnaporthe grisea* lipase 1 gene from pJLin175 was performed with an Applied Biosystems Model 377 XL DNA Sequencer (Perkin-Elmer/Applied Biosystems, Inc., Foster City, Calif.) using dye-terminator chemistry (Giesecke et al., 1992, supra) and primer walking strategy. Nucleotide sequence data were scrutinized for quality and all sequences were compared to each other with assistance of PHRED/PHRAP software (University of Washington, Seattle, Wash.).

Gene models for the lipase gene were predicted based on homology to the *Geotrichum candidum* lipase as well as conserved sequences present at the 5' and 3' ends of fungal introns. A comparative alignment of amino acid sequences was made using the MAFFT method with iterative refinement and default parameters (Katoh et al., 2002, supra). The nucleotide sequence (SEQ ID NO: 5) and deduced amino acid sequence (SEQ ID NO: 6) are shown in FIGS. 12A and 12B. The genomic fragment encodes a polypeptide of 598 amino acids. The % G+C content of the gene is 55.5% and of the mature protein coding region (nucleotides 61 to 1922 of SEQ ID NO: 5) is 55.5%. Using the SignalP software program (Nielsen et al., 1997, supra), a signal peptide of 20 residues was predicted. The predicted mature protein contains 578 amino acids with a molecular mass of 64.3 kDa.

A comparative alignment of lipase sequences was made employing the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Magnaporthe grisea* lipase 1 gene shared 33% identity to the deduced amino acid sequence of a *Geotrichum candidum* lipase gene (SWALL P17573).

Example 24

Cloning of a *Magnaporthe grisea* Lipase 2 Gene

Several synthetic oligonucleotide primers shown below were designed based on the predicted sequence to PCR amplify another *Magnaporthe grisea* gene encoding a lipase 2 from the genomic DNA.

Forward primers:

(SEQ ID NO: 32)
5'-ATTTTCCCGGCTCGACGCTTCTGT-3'

(SEQ ID NO: 33)
5'-TCATGATGCGTCAATCCATCTTCCAGT'-3

(SEQ ID NO: 34)
5'-GGACGAGTTCGTCGCCATGGTGCAGC'-3

Reverse primers:

(SEQ ID NO: 35)
5'-GCTGCACCATGGCGACGAACTCGTCC'-3

(SEQ ID NO: 36)
5'-TTTAATTAATTAGTACCCGCAAATCCATAACAACAAC-3'

Bold letters represent coding sequence. The remaining sequence was homologous to the enzyme restriction insertion sites of pBM120a.

The fragments of interest were amplified by PCR using the Herculase™ Hotstart DNA polymerase system. The First Fragment (Fragment 1) was generated using 50 ng of primer SEQ ID NO: 32 and 50 ng of primer SEQ ID NO: 36 in a PCR reaction (50 µl) containing 300 ng of *Magnaporthe grisea* genomic DNA, 1× Herculase PCR buffer (Stratagene, La Jolla, Calif.) with, 1 µl of dNTP mix (10 mM each), 2 µl DMSO, and 2.5 units of Herculase™ Hotstart DNA polymerase (Stratagene, La Jolla, Calif.). Fragment 2 was amplified using 5 µl of Fragment 1 (PCR reaction) as template with 50 ng of primer SEQ ID NO: 32 and 50 ng of primer SEQ ID NO: 35. Fragment 3 was amplified using 5 µl of Fragment 1 (PCR reaction) as template with 50 ng each primers SEQ ID NO: 34 and SEQ ID NO: 36. The Peltien thermal cycler (MJ Research Inc., Watertown, Mass.) was programmed for 1 cycle at 92° C. for 2 minutes; 30 cycles each at 92° C. for 1 minute, 51° C. for 1 minute, 72° C. for 1 minute; 1 cycle at 72° C. for 10 minutes; and a 4° C. hold.

Figure 13:
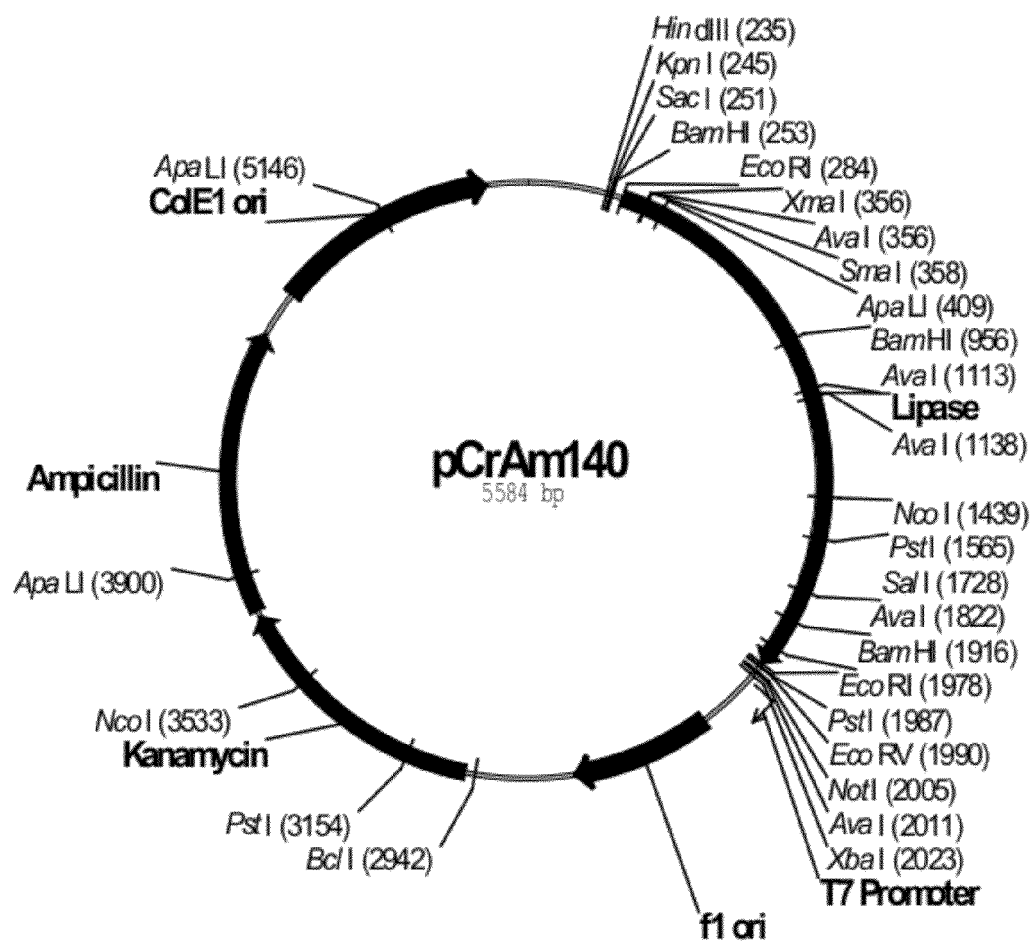
FIG. 13 shows a restriction map of pCrAm140.

The reaction products were visualized on a 1% agarose gel using TAE buffer and the product bands were purified using a QIAquick PCR Purification Kit according to the manufacturer's instructions. The PCR Fragment 1 and pCR2.1-TOPO were ligated using conditions specified by the manufacturer resulting in plasmid pCrAm140 (FIG. 13)

Two µl of the reaction was used to transform *E. coli* TOP10 One Shot competent cells according to the manufacturer's instructions. A 2 µl volume of the ligation mixture was added to the *E. coli* cells and incubated on ice for 5 minutes. Subsequently, the cells were heat shocked for 30 seconds at 42° C., and then placed on ice for 2 minutes. A 250 µl volume of SOC medium was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Twenty colonies that grew on the plates were picked with a sterile toothpick and grown overnight at 37° C., 250 rpm in a 15 ml Falcon tube containing 3 ml of LB medium supplemented with 100 µg of ampicillin per ml. An *E. coli* transformant containing the pCrAm140 was detected by restriction digestion and plasmid DNA was prepared using a BioRobot 9600.

*E. coli* TOP 10 One Shot cells containing pCrAm140 were deposited with the Agricultural Research Service Patent Culture Collection, Northern Regional Research Center, 1815 University Street, Peoria, Ill., 61604, as NRRL B-30788 on Dec. 1, 2004.

Example 25

Characterization of the *Magnaporthe grisea* Genomic Sequence ENCODING Lipase 2

DNA sequencing of the *Magnaporthe grisea* lipase 2 gene from pCrAm140 was performed with an Applied Biosystems Model 377 XL DNA Sequencer using dye-terminator chemistry (Giesecke et al., 1992, supra) and primer walking strategy. Nucleotide sequence data were scrutinized for quality and all sequences were compared to each other with assistance of PHRED/PHRAP software (University of Washington, Seattle, Wash.).

Gene models for the lipase gene were predicted based on homology to the *Geotrichum candidum* lipase as well as conserved sequences present at the 5' and 3' ends of fungal introns. A comparative alignment of amino acid sequences was made using the MAFFT method with iterative refinement and default parameters (Katoh et al., 2002, supra). The nucleotide sequence (SEQ ID NO: 7) and deduced amino acid sequence (SEQ ID NO: 8) are shown in FIGS. 14A and 14B. The genomic fragment encodes a polypeptide of 534 amino acids. The % G+C content of the gene is 66.1% and of the mature protein coding region (nucleotides 55 to 1602 of SEQ ID NO: 7) is 66.1%. Using the SignalP software program (Nielsen et al., 1997, supra, a signal peptide of 18 residues was predicted. The predicted mature protein contains 516 amino acids with a molecular mass of 55.5 kDa.

A comparative alignment of lipase sequences was made employing the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Magnaporthe grisea* lipase 2 gene shared 33% identity to the deduced amino acid sequence of a *Geotrichum candidum* lipase gene (SWALL P17573).

Example 26

Identification of Lipase Genes in the Partial Genomic Sequence of *Neurospora crassa*

A tfasty search (Pearson, W. R., 1999, supra) of the *Neurospora crassa* partial genome sequence (Broad Institute, MIT) was carried out using as query a lipase sequence from *Geotrichum candidum* (SWALL P17577). A gene was identified as putative lipases based upon a high degree of similarity to the query sequence at the amino acid level. One genomic region of approximately 1200 bp with greater than 38% identity to the query sequence at the amino acid level was chosen for further study. Gene models for the putative lipase genes were predicted based on homology to the *Geotrichim candidum* lipase 1 gene as well as conserved sequences present at the 5' and 3' ends of fungal introns.

Example 27

*Neurospora crassa* Genomic DNA Extraction

Four hundred µl of *Neurospora crassa* (FGSC 2489, Fungal Genetics Stock Center) spores were grown in 50 ml of CM medium in a baffled shake flask at 25° C. and 250 rpm for 4 days. Genomic DNA was then extracted from the mycelia using the following method. YEG medium (100 ml) supplemented with 1% additional glucose was inoculated from a plate of PDA plate and incubated for 2 days at 34° C. Mycelia were collected by filtration on a Whatmann #1 filter, frozen in liquid nitrogen, and ground to a powder in a mortar and pestle on dry ice. One-fourth of this material was incubated for 60 minutes at 60° C. with 20 ml of TE containing 20 mM CAPS-NaOH pH 11.0 buffer and 1% lithium dodecyl sulfate. This was extracted with an equal volume of phenol:chloroform:isoamyl alcohol (25:24:1) on a rotating wheel for 60 minutes at 37° C., centrifuged at 2500 rpm for 5 minutes, and the aqueous phase re-extracted in the same fashion. The aqueous phase was brought to 2.5 M ammonium acetate and frozen. It was thawed, the nucleic acids precipitated with 0.7 vol isopropanol, and the precipitate collected by centrifugation at 15,000×g for 20 minutes. The pellet was rinsed twice with 70% ethanol, air dried, and dissolved in 1.0 ml of 0.1×TE. RNase was added to 100 µg per ml and the tube incubated for 30 minutes at room temperature. The solution was brought to 2 M ammonium acetate and DNA precipitated by addition of 2 volumes of ethanol and collected by centrifugation at 13,000×g for 20 minutes at room temperature. The pellet was rinsed twice with 70% ethanol, air-dried, and dissolved in 0.75 ml of 0.1×TE.

Example 28

Cloning of a *Neurospora crassa* Lipase Gene

Two synthetic oligonucleotide primers shown below were designed based on the predicted start and stop codons of the open reading frame to PCR amplify a *Neurospora crassa* lipase gene from the genomic DNA prepared in Example 27.

```
Forward primer:
                                    (SEQ ID NO: 37)
5'-ACACAACTGGCCATGAAGGGCTTTTCCAACGCTCTCCTCG-3'

Reverse primer:
                                    (SEQ ID NO: 38)
5'-AGTCACCTCTAGTTAATTAATTAGATGTGAAGAGCATCAAGAT
TAG-3'
```

Bold letters represent coding sequence. The remaining sequence is homologous to the insertion sites of pBM120a.

The fragment of interest was amplified by PCR using the Expand High Fidelity PCR System (Roche Diagnostics, Mannheim, Germany). Fifty picomoles of each of the primers above were used in a PCR reaction containing 550 ng of *Neurospora Crassa* genomic DNA. The PCR amplification reaction mixture also contained 1×PCR buffer with 1.5 mM $MgCl_2$, 1 µl of dNTP mix (10 mM each), and 0.75 µl DNA polymerase mix (3.5 U/µl) in a final volume of 50 µl. An Eppendorf Mastercycler thermocycler was used to amplify the fragment programmed for 1 cycle at 94° C. for 2 minutes; 10 cycles each at 94° C. for 15 seconds, 62° C. for 30 seconds, and 72° C. for 2 minutes; 15 cycles each at 94° C. for 15 seconds, 62° C. for 30 seconds, and 72° C. for 2 minutes plus a 5 second elongation at each successive cycle; 1 cycle at 72° C. for 7 minutes; and a 10° C. hold.

The reaction product was visualized on a 1.0% agarose gel using TBE buffer and the 1.8 kb product band was purified using a QIAquick PCR Purification Kit according to the manufacturer's instructions.

Figure 15:
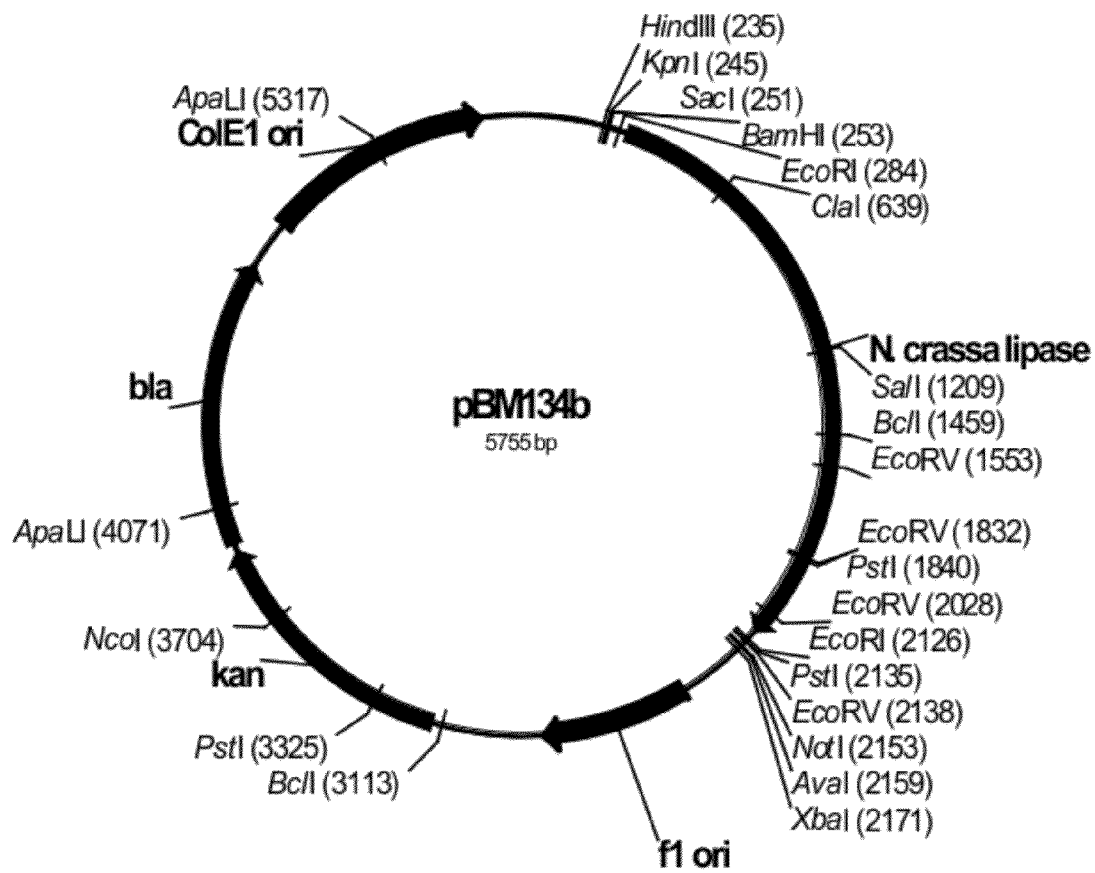
FIG. 15 shows a restriction map of pBM134b.

The 1.8 kb PCR product was then cloned into pCR2.1-TOPO (Invitrogen, Carlsbad, Calif.) according to manufacturer's instructions to produce pBM134b (FIG. 15). Two µl of the reaction was used to transform *E. coli* TOP10 One Shot competent cells. An *E. coli* transformant containing pBM134b was detected by restriction digestion and plasmid DNA was prepared using a QIAGEN BioRobot 9600.

*E. coli* TOP 10 One Shot cells containing pBM134b were deposited with the Agricultural Research Service Patent Culture Collection, Northern Regional Research Center, 1815 University Street, Peoria, Ill., 61604, as NRRL B-30786, with a deposit date of Nov. 17, 2004.

Example 29

Characterization of the *Neurospora crassa* Genomic Sequence Encoding Lipase

DNA sequencing of the *Neurospora crassa* lipase gene from pBM134b was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were analyzed with assistance of ContigExpress software (Informax, Inc., Bethesda, Md.).

Gene models for the lipase gene were predicted based on homology to the *Geotrichum candidum* lipase 1 as well as conserved sequences present at the 5' and 3' ends of fungal introns. A comparative alignment of amino acid sequences was made using the MAFFT method with iterative refinement and default parameters (Katoh et al., 2002, *Nucleic Acids Research* 30: 3059). The genomic coding sequence (SEQ ID NO: 9) and deduced amino acid sequence (SEQ ID NO: 10) are shown in FIGS. 16A and 16B. The genomic fragment encodes a polypeptide of 578 amino acids, interrupted by 1 intron of 55 bp. The % G+C content of the gene is 56.19% and of the mature protein coding region (nucleotides 64 to 1789 of SEQ ID NO: 9) is 56.88%. Using the SignalP software program (Nielsen et al., 1997, *Protein Engineering* 10:1-6), a signal peptide of 21 residues was predicted. The predicted mature protein contains 557 amino acids with a molecular mass of 59.97 kDa.

A comparative alignment of lipase sequences was determined using the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Neurospora crassa* lipase gene shared 31% identity to the deduced amino acid sequences of the *Geotrichum candidum* lipase 1 gene (SWALL P17577).

Deposit of Biological Material

The following biological materials have been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* pJLin173 | NRRL B-30782 | Oct. 12, 2004 |
| *E. coli* pSMO230 | NRRL B-30803 | Dec. 17, 2004 |
| *E. coli* pJLin175 | NRRL B-30783 | Sep. 13, 2004 |

| Deposit | Accession Number | Date of Deposit |
|---|---|---|
| E. coli pCrAm140 | NRRL B-30788 | Dec. 1, 2004 |
| E. coli pBM134b | NRRL B-30786 | Nov. 17, 2004 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polynucleotide encoding a polypeptide having lipase activity, selected from the group consisting of:
   (a) a polynucleotide encoding a polypeptide having lipase activity comprising an amino acid sequence having at least 90% identity with the mature polypeptide of SEQ ID NO: 4;
   (b) a polynucleotide encoding a polypeptide having lipase activity comprising a nucleotide sequence which hybridizes under at least high stringency conditions with the mature polypeptide coding sequence of SEQ ID NO: 3 or its full-length complementary strand, wherein high stringency conditions are defined as prehybridization and hybridization at 42° C. in 5×SSPE, 0.3% SDS, 200 µg/ml sheared and denatured salmon sperm DNA, and 50% formamide and a wash three times, each for 15 minutes using 2×SSC, 0.2% SDS at 65° C.; and
   (c) a polynucleotide encoding a polypeptide having lipase activity comprising a nucleotide sequence having at least 90% identity with the mature polypeptide coding sequence of SEQ ID NO: 3.

2. The isolated polynucleotide of claim 1, wherein the polypeptide comprises an amino acid sequence having at least 90% identity with the mature polypeptide of SEQ ID NO: 4.

3. The isolated polynucleotide of claim 2, wherein the polypeptide comprises an amino acid sequence having at least 95% identity with the mature polypeptide of SEQ ID NO: 4.

4. The isolated polynucleotide of claim 3, wherein the polypeptide comprises an amino acid sequence having at least 97% identity with the mature polypeptide of SEQ ID NO: 4.

5. The polynucleotide of claim 1, wherein the polypeptide comprises or consists of the amino acid sequence of SEQ ID NO: 4 or the mature polypeptide thereof.

6. The isolated polynucleotide of claim 1, which comprises a nucleotide sequence which hybridizes under at least high stringency conditions with the mature polypeptide coding sequence of SEQ ID NO: 3 or its full-length complementary strand, wherein high stringency conditions are defined as prehybridization and hybridization at 42° C. in 5×SSPE, 0.3% SDS, 200 µg/ml sheared and denatured salmon sperm DNA, and 50% formamide and a wash three times, each for 15 minutes using 2×SSC, 0.2% SDS at 65° C.

7. The isolated polynucleotide of claim 6, which comprises a nucleotide sequence which hybridizes under at least very high stringency conditions with the mature polypeptide coding sequence of SEQ ID NO: 3 or its full-length complementary strand, wherein very high stringency conditions are defined as prehybridization and hybridization at 42° C. in 5×SSPE, 0.3% SDS, 200 µg/ml sheared and denatured salmon sperm DNA, and 50% formamide and a wash three times, each for 15 minutes using 2×SSC, 0.2% SDS at 70° C.

8. The polynucleotide of claim 1, which comprises a nucleotide sequence having at least 90% identity with the mature polypeptide coding sequence of SEQ ID NO: 3.

9. The polynucleotide of claim 8, which comprises a nucleotide sequence having at least 95% identity with the mature polypeptide coding sequence of SEQ ID NO: 3.

10. The polynucleotide of claim 9, which comprises a nucleotide sequence having at least 97% identity with the mature polypeptide coding sequence of SEQ ID NO: 3.

11. The polynucleotide of claim 1, which comprises or consists of the nucleotide sequence of SEQ ID NO: 3 or the mature polypeptide coding sequence thereof.

12. The polynucleotide of claim 1, which is encoded by the polynucleotide contained in plasmid pSMO230 which is contained in E. coli NRRL B-30803.

13. The polynucleotide of claim 1, wherein the mature polypeptide is amino acids 25 to 588 of SEQ ID NO: 4.

14. The polynucleotide of claim 1, wherein the mature polypeptide coding sequence is nucleotides 73 to 1764 of SEQ ID NO: 3.

15. A nucleic acid construct or expression vector comprising the polynucleotide of claim 1 operably linked to one or more control sequences that direct the production of the polypeptide in an expression host.

16. A recombinant host cell comprising the polynucleotide of claim 1 operably linked to one or more control sequences that direct the production of the polypeptide.

17. A method for producing a polypeptide having lipase activity, comprising: (a) cultivating the host cell of claim 16 under conditions conducive for production of the polypeptide; and (b) recovering the polypeptide.

18. A method for producing a polypeptide having lipase activity, comprising: (a) cultivating a transgenic plant or a plant cell comprising the polynucleotide of claim 1 under conditions conducive for production of the polypeptide; and (b) recovering the polypeptide.

\* \* \* \* \*

UNITED STATES PATENT AND TRADEMARK OFFICE
CERTIFICATE OF CORRECTION

PATENT NO. : 8,383,383 B2
APPLICATION NO. : 13/599199
DATED : February 26, 2013
INVENTOR(S) : Yaver et al.

It is certified that error appears in the above-identified patent and that said Letters Patent is hereby corrected as shown below:

Title page, item (62) Related U.S. Application Data

On line 1 delete "13/440,642" and insert --13/440,626--

On line 2 delete "8,268,589" and insert --8,263,824--

Signed and Sealed this
Seventeenth Day of September, 2013

Teresa Stanek Rea
*Deputy Director of the United States Patent and Trademark Office*